US008658608B2

(12) United States Patent
Glazer et al.

(10) Patent No.: US 8,658,608 B2
(45) Date of Patent: Feb. 25, 2014

(54) MODIFIED TRIPLE-HELIX FORMING OLIGONUCLEOTIDES FOR TARGETED MUTAGENESIS

(75) Inventors: Peter M. Glazer, Guilford, CT (US); Michael M. Siedman, Washington, DC (US)

(73) Assignees: Yale University, New Haven, CT (US); Department of Health and Human Services, Washington, DC (US)

( * ) Notice: Subject to any disclaimer, the term of this patent is extended or adjusted under 35 U.S.C. 154(b) by 489 days.

(21) Appl. No.: 11/562,849

(22) Filed: Nov. 22, 2006

(65) Prior Publication Data

US 2007/0219122 A1 Sep. 20, 2007

Related U.S. Application Data

(60) Provisional application No. 60/739,740, filed on Nov. 23, 2005.

(51) Int. Cl.
C12N 15/11 (2006.01)
C07H 21/04 (2006.01)
C12N 5/00 (2006.01)

(52) U.S. Cl.
USPC .......... 514/44 A; 536/23.1; 435/325; 530/380

(58) Field of Classification Search
USPC .............................. 435/6, 440; 536/23.1, 24.3
See application file for complete search history.

(56) References Cited

U.S. PATENT DOCUMENTS

| | | | |
|---|---|---|---|
| 3,832,253 A | 8/1974 | Di Palma et al. | |
| 3,854,480 A | 12/1974 | Zaffaroni | |
| 4,452,775 A | 6/1984 | Kent | |
| 4,667,013 A | 5/1987 | Reichle | |
| 4,675,189 A | 6/1987 | Kent | |
| 4,748,034 A | 5/1988 | de Rham | |
| 5,075,109 A | 12/1991 | Tice et al. | |
| 5,133,974 A | 7/1992 | Paradissis et al. | |
| 5,239,660 A | 8/1993 | Ooi | |
| 5,354,670 A | 10/1994 | Nickoloff et al. | |
| 5,407,686 A | 4/1995 | Patel et al. | |
| 5,422,251 A | 6/1995 | Fresco | |
| 5,665,541 A * | 9/1997 | Miller et al. | 435/6 |
| 5,736,152 A | 4/1998 | Dunn | |
| 5,739,308 A * | 4/1998 | Kandimalla et al. | 536/24.5 |
| 5,776,744 A | 7/1998 | Glazer | |
| 5,932,711 A * | 8/1999 | Boles et al. | 536/22.1 |
| 5,962,426 A | 10/1999 | Glazer | |
| 6,303,376 B1 | 10/2001 | Glazer | |
| 6,331,617 B1 * | 12/2001 | Weeks et al. | 536/24.5 |
| 6,363,746 B1 | 4/2002 | Wei et al. | |
| 6,632,919 B1 * | 10/2003 | Nielsen et al. | 530/300 |
| 6,686,463 B2 * | 2/2004 | Beigelman et al. | 536/27.1 |
| 6,919,208 B2 | 7/2005 | Levy et al. | |
| 7,279,463 B2 * | 10/2007 | Glazer | 514/44 |
| 2004/0241651 A1 * | 12/2004 | Olek et al. | 435/6 |

FOREIGN PATENT DOCUMENTS

| | | |
|---|---|---|
| EP | 0253193 | 1/1988 |
| EP | 0266099 | 5/1988 |
| EP | 0375408 | 6/1990 |
| WO | WO 92/20698 | 11/1992 |
| WO | WO 93/17102 | 9/1993 |
| WO | WO 95/01364 | 1/1995 |
| WO | WO 95/13650 | 1/1995 |
| WO | WO 95/26136 | 10/1995 |
| WO | WO96/02558 | * 2/1996 |
| WO | WO 96/17074 | 6/1996 |
| WO | WO 96/40271 | * 12/1996 |
| WO | WO 98/34945 | 8/1998 |
| WO | WO 00/22113 | 4/2000 |
| WO | WO 00/22114 | 4/2000 |
| WO | WO 01/25419 | 4/2001 |

OTHER PUBLICATIONS

Shahid et al (Biochem. 45: 1970-1978, published on the Web on Jan. 24, 2006).*
Kuhn et al (J. Mol. Biol. 286: 1337-1345, 1999).*
Rogers et al (Proc. Nat. Acad. Sci. USA 99(26): 16695-16700, 2002).*
Egholm et al (Nucl. Acids. Res. 23(2): 217-222, 1995).*
Mayer (Org. Biomol. Chem. 3:1653-1658, Apr. 2005).*
Triesman et al (Cell 29(3): 903-911, 1982).*
Kukreti et al (Nucl. Acids Res. 25(21): 4264-4270, 1997).*
Schneider et al (Nucl. Acids Res. 38(13): 4394-4403 , 2010).*
Vasquez et al (TIBS 23: 4-9, 1998).*
Seksek et al (Journal of Cell Science 109, 257-262 (1996).*
Agrawal, et al., "Pharmacokinetics, biodistribution, and stability of oligoeoxynucleotide phosphorothioates in mice," *Proc Natl Acad Sci U S A.* 88(17):7595-9 (1991).
Allison, et al, "The C-Terminal Domain of the Largest Subunit of RNA Polymerase II of *Saccharomyces cerevisiae, Drosophila melanogaster*, and Mamals: A Conserved Structure with an Essential Function," *Molecular and Cellular Biology*, 8(1):321-329 (1988).
Asensio, et al. "Thermodynamic, kinetic, and conformational properties of a parallel intermolecular DNA triplex containing 5' and 3' junctions", *Biochemistry*, 37(43):15188-98 (1998).

(Continued)

Primary Examiner — Richard Schnizer
(74) Attorney, Agent, or Firm — Pabst Patent Group LLP

(57) ABSTRACT

High affinity, chemically modified triplex-forming oligonucleotides (TFOs) and methods for use thereof are disclosed. TFOs are defined as triplex-forming oligonucleotides which bind as third strands to duplex DNA in a sequence specific manner. Triplex-forming oligonucleotides may be comprised of any possible combination of nucleotides and modified nucleotides. Modified nucleotides may contain chemical modifications of the heterocyclic base, sugar moiety or phosphate moiety. A high affinity oligonucleotide ($K_d \leq 2 \times 10^{-8}$) which forms a triple strand with a specific DNA segment of a target gene DNA is generated. It is preferable that the $K_d$ for the high affinity oligonucleotide is below $2 \times 10^{-10}$. The nucleotide binds or hybridizes to a target sequence within a target gene or target region of a chromosome, forming a triplex region. The binding of the oligonucleotide to the target region stimulates mutations within or adjacent to the target region using cellular DNA synthesis, recombination, and repair mechanisms. The mutation generated activates, inactivates, or alters the activity and function of the target gene.

23 Claims, 8 Drawing Sheets

(56) References Cited

OTHER PUBLICATIONS

Asensio, et al., "The Contribution of Cytosine Protonation to the Stability of Parallel DNA Triple Helices," *J. Mol. Biol.*, 275(5): 811-822 (1998).
Baron, et al., "Localization of the Centrin-Related 165,000—M.sub.r Protein of PtK.sub.2 Cells During the Cell Cycle," *Cell Motil. and the Cytoskel*, 18:144 (1991).
Barre, et al., "Unambiguous demonstration of triple-helix-directed gene modification," *Proc. Natl. Acad. Sci. USA* 97, 3084 (2000).
Baumann, et al., "Role of the human RAD51 protein in homologous recombination and double-stranded-break repair," *Trends Biochem Sci* 23(7):247-251 (1998).
Beal & Dervan, "The Influence of Single Base Triplet Changes on the Stability of a Pur.Pur.Pyr Triple Helix Determined by Affinity Cleaving," *Nucleic Acids Res*. 20(11): 2773-2776 (1992).
Beal, et al., "Second Structural Motif for Recognition of DNA by Oligonucleotide-Directed Triple-Helix Formation," *Science* 251:1360-1363 (1991).
Bennett & Davis, "Erythrocyte ankyrin: Immunoreactive analogues are associated with mitotic structures in cultured cells and with microtubules in brains," *Proc. Natl. Acad. Sci*. USA. 78: 7550-7554 (1981).
Blume, et al., "Triple helix formation by purine-rich oligonucleotides targeted to the human dihydrofolate reductase promoter", *Nucleic Acids Res.*, 20(7):1777-84 (1992).
Bramlage, et al., "Designing ribozymes for the inhibition of gene expression," *Trends Biotechnol*. 16, 434 (1998).
Bredberg, et al., "Psoralen adducts in a shuttle vector plasmid propagated in primate cells: high mutagenicity of DNA cross-links", *Carcinogenesis* 8(12):1923-27 (1987).
Bregman et al., "Cytostellin distributes to nuclear regions enriched with splicing factors," *J Cell Sci*. 107 (Pt 3):387-96 (1994).
Brenneman, et al., "Stimulation of intrachromosomal homologous recombination in human cells by electroporation with site-specific endonucleases," *Proc. Natl. Acad. Sci*. USA 93(8):3608-12 (1996).
Campbell, et al., "Homologous; recombination involving small single-stranded oligonucleotides in human cells," *New Biol.* 1(2):223-7 (1989).
Capecchi, "Altering the genome by homologous recombination," *Science* 244(4910): 1288-1292 (1989).
Chan, et al., "Targeted correction of an episomal gene in mammalian cells by a short DNA fragment tethered to a triplex-forming oligonucleotide," *J. Biol. Chem*. 274(17): 11541-11548 (1999).
Chan, et al., "Triplex DNA: Fundamentals, Advances, and Potential Applications for Gene Therapy," *J. Mol. Med*. 75: 267-282 (1997).
Chen, et al., "In Vivo Expression of Single-Stranded DNA in Mammalian Cells with DNA Enzyme Sequences Targeted to C-raf," *Antisense Nucleic Acid Drug Dev*. 10: 415-422 (2000).
Chen, et al., "Ethyl carbamate metabolism: in vivo inhibitors and in vitro enzymatic systems." *Drug Metab. Dispos*. 18, 815 (1990).
Connell, et al., *Biotechniques* 5:342 (1987).
Cooney, "Site-Specific Oligonucleotide Binding Represses Transcription of the Human *c-myc* Gene in Vitro," *Science* 241:456 (1988).
Cuenoud, et al., "Dual recognition of doUble-stranded DNA by 2'-aminoethoxy-modified oligonucleotides", *Angew. Chem. Int. Ed.*, 37:1288-12911 (1998).
Dagle, et al., "Positively charged oligonucleotides overcome potassium-mediated inhibition of triplex DNA formation", *Nucleic Acids Res.*, 24(11):2143-9 (1996).
Dahmus, "Phosphorylation of Eukaryotic DNA-dependent RNA Polymerase," J. Biol. Chem. 256:3332-3339 (1981).
Datta, et al., "Triplex-induced Recombination in Human Cell-free Extracts;" *J. Biol. Chem*. 276: 18018-18023 (2001).
Durland, et al., "Binding Of Triple Helix Forming Oligonucleotides to Sites In Gene Promoters", *Biochemistry* 30:9246 (1991).
Duval-Valentin, et al., "Specific Inhibition of Transcription by Triple Helix-Forming Oligonucleotides," *Proc. Natl. Acad. Sci. USA* 89:504 (1992).

Fakan & Bernhard, "Localization of Rapidly and Slowly Labelled Nuclear RNA as Visualized by High Resolution Autoradiography," *Exp. Cell Res*. 67:129-141 (1971).
Fakan & Nobis, "Ultrastructural Localization of Transcription Sites and of RNA Distribution During the Cell Cycle of Synchronized Cho Cells," *Exp. Cell Res*. 113:327-337 (1978).
Fakan & Puvion, "The Ultrastructural Visualization of Nucleolar and Extranucleolar RNA Synthesis and Distribution," *Int. Rev. Cytol..* 65:255-99 (1980).
Fakan, et al., "Localization and Characterization of Newly Synthesized Nuclear RNA in Isolated Rat Hepatocytes," *Exp. Cell. Res*. 99:155-164 (1976).
Famulok, "Oligonucleotide aptamers that recognize small molecules," *Curr. Opin. Struct. Biol*. 9, 324 (1999).
Faria, et al., "Targeted Inhibition of Trancription Elongation in Cells Mediated by Triplex-Forming Oligonucleotides," *Proc. Natl. Acad. Sci*. USA, 97: 3862-3867 (2000).
Faruqi, et al., "Triple-helix formation, induces recombination in mammalian cells via a nucleotide excision repair-dependent pathway," *Mol Cell Biol* 20(3): 990-1000 (2000).
Faruqi, et al., "Recombination induced by triple helix-targeted DNA damage in mammalian cells", *Mol. Cell. Biol*. 16: 6820-6828, (1996).
Felsenfeld, et al., "Formation of a three-stranded polynucleotide Molecule," *J. Am. Chem. Soc*. 79:2023-2024 (1957).
Francois, "Sequence-Specific Recognition and Cleavage of Duplex DNA via Triple-Helix Formation by Oligonucleotides Covalentiy Linked to a Phenanthroline-Copper Chelate," *Proc. Natl. Acad. Sci. USA* 86:9702 (1989).
Galderisi, et al., "Antisense oligonucleotides as therapeutic agents," *J. Cell Physiol*. 181, 251 (1999).
Gasparro, et al., "Site-specific targeting of Psoralen Photoadducts with a Triple Helix-Forming Oliganucleotide: Characterization of Psoralen Monoadduct and Crosslink Formation," *Nucleic Acids Research*, 22(14):2845-2852 (1994).
Gasparro, et al., "Photoactivatable antisense DNA: suppression of ampicillin resistance in normally resistant *Escherichia coli.,*" *Antisense Res. Dev*. 1:117-140 (1991).
Gasparro, et al.,"Rapid and sensitive analysis of 8-methoxypsoralen in plasma," *J. Invest. Derm*. 90:234-236 (1988).
Gerace, et al., "Immunocytochemical Localization of the Major Polypeptides of the Nuclear Pore Complex—Lamina Fraction," *J. Cell Biol*. 79:546-566 (1978).
Gia, et al., "Sequence specificity of psoralen photobinding to DNA: a quantitative approach," *Biochemistry* 31:11818-11822 (1992).
Giovannangeli, et al., "Oligodeoxynucleotide-directed photo-induced cross-linking of HIV proviral DNA via triple-helix formation," *Nucleic Acids Res*. 20:4275-4281 (1992).
Giovannangeli, et al., "Triplex-forming molecules for modulation of DNA information processing," *Curr. Opin. Mol. Ther*. 2(3): 288-296 (2000).
Giovannangeli, et al., "Triple-helix formation by oligonucleotides containing the three bases thymine, cytosine, and guanine," *Proc. Natl. Acad. Sci. USA* 89:8631-8635 (1992).
Glazer, et al., "Detection and Analysit of UV-induced Mutations in Mammalian Cell DNA Using A Phage Suttle Vector," *Proc. Natl. Acad. Sci*. 83:1041-1044 (1986).
Glazer, et al:, "DNA mismatch repair detected in human cell extracts," *Mol. Cell. Biol*. 7:218 (1987).
Goncz et al., "Site-directed alteration of genomic DNA by small-fragment homologous replacement," *Methods Mol. Biol*. 133:85-89 (2000).
Good, et al., "Progress in developing PNA as a gene-targeted drug," *Antisense Nucleic Acid Drug Dev*. 7(4):431-7 (1997).
Gordenin et al., "Yeast ARMs (DNA at-risk motifs) can reveal sources of geonome instabilty," *Mutat. Res*, 400(1-2)45-58 (1998).
Gorman, et al., "Stable Alteration of Pre-mRNA Splicing Patterns by Modified U7 Small Nuclear RNAs," *Proc. Natl. Acad. Sci*. USA, 95: 4929-4934 (1998).
Gottesfeld, et al., "Regulation of gene expression by small molecules" *Nature* 387(6629):202-5 (1997).
Grigoriev, et al., "A Triple-Helix-Forming Oligonucleotide-Intercalator Conjugate Acts as a Transcriptional Repressor via Inhi-

(56) References Cited

OTHER PUBLICATIONS bition of NF κB Binding to Interleukin-2 Receptor α-Regulatory Sequence," *J. of Biological Chem.* 267:3389 (1992).
Grigoriev, et al., "Inhibition of Gene Expression by Triple Helix-directed DNA Cross-Linking at Specific Sites," *Proceedings of the National Academy of Sciences of USA*, 90(8):3501-3505 (1993).
Grigoriev, et al., "Oligodeoxynucleotide-directed Photo-induced Cross-linking of HIV Proviral DNA via Triple-helix Formation," *Nucleic Acids Research*, 20(16):4275-4281 (1992).
Gura, "Antisense has growing pains," *Science* 270:575-77 (1995).
Hanawalt, "Transcription-coupled repair and human diseases," *Science* 266(5193): 1957-1958 (1994).
Hanson, et al., "Analysis of biological selections for high-efficiency gene targeting," *Mol. Cell. Biol.* 15(1):45-51 (1995).
Harding, "NMR Studies on YSPTSPSY: Implications for the Design of DNA Bisintercalators," *Journal of Medicinal Chemistry*, 35:4658-4664 (1992).
Hartley, et al., "Electrophoretic and chromatographic separation methods used to reveal interstrand crosslinking of nucleic acids", *J. Chromatogr.*, 618(1-2)277-88 (1993).
Havre & Glazer, "Targeted mutagenesis of simian virus 40 DNA mediated by a triple helix-forming oligonucleotide," *J. Virol.* 67(12):7324-31 (1993).
Havre, et al.; "Targed Mutagenesis of DNA Using Triple Helix-forming Oliginucleotides Linked to Psoralen," *Proc. Natl. Acad. Sci. USA*, 90(16):7879-7883 (1993).
Havre, et al., "Targeted mutagenesis of simian virus 40 DNA mediated by a triple helix-forming oligonucleotide," *J. Virology* 67:7324-7331 (1993).
Helene, "Sequence-selective.recognition and cleavage of double-helical DNA," *Curr. Opinion Biotechnology* 4:29-36 (1993).
Helene, et al., "The anti-gene strategy: control of gene expression by triplex-forming-oligonucleotides," *Anticancer Drug Des.* 6(6):569-84 (1991).
Henry & Hodge, "Nuclear Matrix: A Cell-Cycle-Dependent Site of Increased Intranuclear Protein Phosphorylation," *Eur. J. Biochem.* 133:23-29 (1983).
Hirt, et al., "Selective extraction of polyoma DNA from infected mouse cell cultures" *J. Mol. Biol.* 26:365-369 (1967).
Huang & Spector, "Nascent pre-mRNA transcripts are associated with nuclear regions enriched in splicing factors," *Genes and Dev.* 5:2288 (1991). Ito, et al., "Sequence-Specific DNA Purification By Triplex Affinity Capture", *Proc. Natl. Acad. Sci. USA* 89:495 (1992).
Huang, et al., "Functional silencing of hepatic microsomal glucose-6-phosphatase gene expression in vivo by adenovirus-mediated delivery of short hairpin RNA", *FEBS Lett.*, 558(1-3) 69-79 (2004).
Ito, et al., "Sequence-specific DNA purification by triplex affinity capture," *Proc. Natl. Acad. Sci. USA* 89:495 (1992).
Iverson, et al., "In vivo studies with phosphorothioate oligonucleotides: pharmacokinetics prologue," *Anticancer Drug Des.* 6(6):531-8 (1991).
Jackson, et al., "Visualization of focal sites of transcription within human nuclei," *EMBO* 12:1059-1065 (1993).
Jakubczak et al., "Analysis of genetic instability during mammary tumor progression using a novel selection-based assay for in vivo mutations in bacteriophage lambda transgene target," *Proc. Natl. Sci. USA* 93:9073-9078 (1996).
James, et al., "Towards gene-inhibition therapy: a review of progress and prospects in the field of antiviral antisense nucleic acids and ribozymes," *Antiviral Chemistry & Chemotherapy* 2:191-214 (1991).
Jepsen, et al., "LNA-antisense rivals siRNA for gene silencing", *Curr. Opin. Drug Discov. Devel.*, 7(2):188-94 (2004).
Jones & Wood, "Preferential binding of the xeroderma pigmentosum group A complementing protein to damaged DNA," *Biochemistry* 32(45):12096-104 (1993).
Khiat, et al., "Structural Differences Between the Free and Bound States of DNA-Bisintercalating Peptide YSPTSPSY," *Journal of Medicinal Chemistry*, 39(21):2495 (1996).

Kim, et al., "Inhibition of Transcription of the Human c-myc Protooncogene by Intermolecular Triplex," *Biochemistry* 37: 2299-304 (1998).
Kitagawa, et al., *J. Biochem.* 79:233-236 (1976).
Kramer, et al., "Monoclonal Antibody Directed Against RNA Polymerase II of *Drosophila melanogaster*," *Molec. Gen. Genet.* 180:193-199 (1980).
Lacroix, et al, "Triplex formation by oligtinucleotides containing 5-(1-propynyl)-2'-deoxyuridine: decreased magnesium dependence and improved intracellular gene targeting", *Biochemistry*, 38(6):1893-901(1999).
Laemmli, "Cleavage of Structural Proteins during the Assembly of the Head of Bacteriophage T4," *Nature.* 227:680-685 (1970).
Lassner, et al., "Targeting of T7 RNA polymerase to tobacco nuclei mediated by an SV40 nuclear location signal," *Plant Mol Biol.* 17(2):29-34 (1991).
Lee & Greenleaf, "A protein kinase that phosphorylates the C-terminal repeat domain of the largest subunit of RNA polymerase II," *Proc. Natl. Acad. Sci. U. S. A.* 86:3624-28 (1989).
Letai, et al., "Specificity in formation of triple-stranded nucleic acid helical complexes: studies with agarose-linked polyribonucleotide affinity columns," *Biochemistry* 27:9108 (1988).
Lin, et al., "Extrachromosomal recombination in mammalian cells as studied with single- and double-stranded DNA substrates," *Mol. Cell Biol* 7(1):129-140 (1987).
Lin, et al., "Repair of double-stranded DNA breaks by homologous DNA fragments during transfer of DNA into mouse L Cells," *Molecular and Cellular Biology* 10:113-119 (1990).
Lin, et al., "Use of EDTA derivatization to characterize interactions between oligodeoxyribonucleoside methylphosphonates and nucleic acids," *Biochemistry* 28:1054 (1989).
Lind, et al., "Structural characteristics of 2'-O-(2-methoxyethyl)-modified nucleic acids from molecular dynamics simulations", *Nucleic Acids Res.*, 26(16):3694-799 (1998).
Liu, et al., *Biochem.* 18:690-697 (1979).
Lorenz, et al., "Steriod and lipid conjugates of siRNAs to enhance cellular uptake and gene silencing in liver cells", *Bioorg. Med. Chem. Lett.*, 14(19):4975-7 (2004).
Luo, et al., "High-frequency intrachromosomal gene conversion induced by triplex-forming oligonucleotides microinjected into mouse cells," *Proc. Natl. Acad. Sci. USA* 97(16): 9003-9008 (2000).
Ma, et al., "Nuclease-resistant external guide sequence-induced cleavage of target RNA by human ribonuclease P", *Antisense Nucleic Acid Drug Dev.*, 8(5):415-26 (1998).
Maher, et al., "Analysis of Promoter-Specific Repression by Triple Helical DNA Complexes in a Eukaryotic Cell-Free Transcription System," *Biochemistry* 31:70 (1992).
Maher, et al., "Inhibition of DNA binding proteins by oligonucleotide-directed triple helix formation," *Science* 245:725 (1989).
Majumdar, et al., "Cell cycle modulation of gene targeting by a triple helix-forming oligonucleotide", *J. Biol. Chem.*, 278(13):11072-7 (2003).
Majumdar, et al., "Gene targeting by triple helix-forming oligonucleotides", *Ann. N.Y. Acad. Sci.*, 1002:141-53 (2003).
Majumdar, et al., "Targeted gene knockout mediated by triple helix forming oligonucleotides", *Nature Genet.* 20:212-214 (1998).
Mergny, et al., "Sequence specificity in triple-helix formation: experimental and theoretical studies of the effect of mismatches on triplex stability," *Biochemistry* 30:979 (1991).
Mirabelli, et al., "In Vitro and in vivo pharmacologic activities of antisense oligonucleotides," *Anticancer Design* 6:647-661 (1991).
Moser & Dervan, "Sequence-specific cleavage of double helical DNA by triple helix formation," *Science* 238: 645 (1987).
Myhr, "Validation studies with Muta Mouse: a transgenic mouse model for detecting mutations in vivo," *Environ. Mol. Mutagen*, 18:308(1991).
Narayanan, et al., "Elevated levels of mutation in multiple tissues of mice deficient in the DNA mismatch repair gene Pms2," *Proc. Natl. Acad. Sci. USA* 94:3122-3127 (1997).

(56) References Cited

OTHER PUBLICATIONS

Nickerson, et al., "A Normally Masked Nuclear Matrix Antigen That Appears at Mitosis on Cytoskeleton Filaments Adjoining Chromosomes, Centrioles, and Midbodies," *J. Cell. Biol*, 116:977-987 (1992).

Noonberg, et al., "In Vivo Generation of Highly Abundant Sequence-Specific Oligonucleotides for Antisense and Triplex Gene Regulation," *Nucleic Acids Res.* 22: 2830-2836 (1994).

Nyce and Metzger, "DNA antisense therapy for asthma in an animal model", *Nature*, 385(6618):721-5 (1997).

Obika, et al., "2'-O,4'-C-Methylene bridged nucleic acid (2', 4'-BNA): synthesis and triplex-forming properties", *Bioorg. Med. Chem.*, 9(4):1001-11 (2001).

Pierce Immunotechnology Catalog and Handbook, 1992-93 Edition, pp. A16-A17.

O'Keefe, et al., Disruption of Pre-mRNA Splicing In Vivo Results in Reorganization of Slicing Factors, *J. Cell Biol*. 124:249-260 (1994).

Orson, et al., "Oligonucleotide inhibition of IL2 alpha mRNA transcription by promoter region collinear triplex formation in lymphocytes," *Nucleic Acids Res*. 19:3435 (1991).

Park, et al., "Formation of ternary complex by human XPA, ERCC1, and ERCC4(XPF) excision repair proteins," *Proc. Natl. Acad. Sci. USA* 91:5017-5021 (1994).

Parris, et al., "Proximal and distal effects of sequence context on ultraviolet mutational hotspots in a shuttle vector replicated in xeroderma cells," *J mol Biol*. 236: 491 (1994).

Pattanayek, et al., "Structural rationalization of a large difference in RNA affinity despite a small difference in chemistry between two 2'-O-modified nucleic acid analogues", *J. Am. Chem. Soc.*, 126(46): 15006-7 (2004).

Pei, "Site Specific Cleavage of Duplex DNA by a Semisynthetic Nuclease via Triple-Helix Formation," *Proc. Natl. Acad. Sci. USA* 87:9858 (1990).

Perroualt, et al., "Sequence-specific artifical photo-induced ndonucleases based on triple-helix forming oligonucleotides," *Nature* 344:358 (1990).

Postel, et al., "Evidence that a triplex-forming oligodeoxyribonucleotide binds to the c-myc promoter in HeLa cells, thereby reducing c-myc mRNA levels," *Proc. Natl. Acad. Sci. USA* 88:8227 (1991).

Posvic, et al., "Sequence-Specific Alkylation of Double Helical DNA by Oligonucleotide Directed Triple-Helix Formation," *J. Am. Chem. Soc*. 112:9428 (1990).

Prakash, et al., "2'-O-[2-(guanidinium)ethyl]-modified ogligonucleotides: stabilizing effect on duplex and triplex structures", *Org. Lett.*, 6(12):1971-4 (2004).

Praseuth, et al., "Sequence-Specific Binding and Photocrosslinking of α and β Oligodeoxynucleotides to the Major Groove of DNA via Triple-Helix Formation," *Proc. Natl. Acad. Sci. USA* 85:1349 (1988).

Price & Pettijohn, "Redistribution of the Nuclear Mitotic Apparatus Protein (NuMA) during Mitosis and Nuclear Assembly," *Exp. Cell Res.*, 166:292-311 (1986).

Puri, et al., "Minimum number of 2'-O-(2-aminoethyl) residues required for gene knockout activity by triple helix forming oligonucleotides", *Biochemistry*, 41(24):7716-24 (2002).

Raha, et al., "Mutagenesis by Third-Strand-Directed Psoralen Adducts in Repair-Deficient Human Cells: High Frequency and Altered Specgrum in a Xeroderma Pigmentosum Variant," *Proc. Natl. Acad. Sci. USA*, 93(7):2941-2942 (1996).

Reardon, et al., "Removal of psoralen monoadducts and crosslinks by human cell free extracts," *Nucleic Acids Res*. 19:4623 (1991).

Roberts, et al., "Stability and Properties of Double and Triple Helices: Dramatic Effects of RNA or DNA Backbone Composition," *Science* 258: 1463-1466 (1992).

Rooney & Moore, "Antiparallel, intramolecular triplex DNA stimulates homologous recombination in human cells," *Proc. Natl. Acad. Sci. USA* 92:2141-2144 (1995).

Rump, et al., "Modification of the plasma clearence and liver uptake of steriod ester-conjugated oligodeoxynucleotides by association with (lactosylated) low-density lipoprotein", *Biochem. Pharmacol.*, 59(11):1407-16 (2000).

Sambrook, et al., Molecular Cloning, A Laboratory Manual, second edition, Cold Spring Harbor Laboratory Press, New York (1990).

Sancar, "DNA excision repair," *Annu. Rev. Biochem*. 65: 43-81 (1996).

Seipel, et al, "Basal Components of the Transcription Apparatus (RNA Polymerase II, TATA-binding Protein) Contain Activation Domains: Is Repetitive C-Terminal Domain (CTD) of RNA Polymerase II a Portable Enhancer Domain?," *Chemical Abstracts*, 122(17), Abstract No. 206769 (1994).

Seidman, et al., *The Clinical Journal of Investigation* 122(4):487-94 (2003).

Semerad & Maher, "Exclusion of RNA Strands from a Purine Motif Triple Helix," *Nucleic Acids Res*. 22: 5321-5325 (1994).

Shevelev, et al., "Potential Triple Helix-Mediated Inhibition of IGF-I Gene Expression Significantly Reduces Tumorigenicity of Gilolastoma in an Animal Model," *Cancer Gene Therapy* 4: 105-112 (1997).

Shimizu, et al., "Oligo(2'-O-methyl)ribonucleotides. Effective probes for duplex DNA", *FEBS Lett.*, 302(2):155-8 (1992).

Shivji, et al., "Proliferating cell nuclear antigen is required for DNA excision repair," *Cell* 69: 367 (1992).

Sibghat-Ullah, et al., "Human nucleotide excision repair in vitro: repair of pyrimidine dimers, psoralen and cisplatin adducts by HeLa cell-free extract," *Nucleic Acids Res*. 17:4471-4487 (1989).

Sidransky, et al., *Science* 252:706-709 (1991).

Singleton & Dervan, "Influence of pH on the Equilibrium Association Constants for Oligodeoxyribonucleotide-Directed Triple Helix Formation at Single DNA Sites," *Biochemistry* 31: 10995-1003 (1992).

Smith et al., "Alterations in chromatic Conformation Are Accompanies by Reorganization of Nonchromatin Domains That Contain U-snRNP Protein p28 and Nuclear Protein p107," *J. Cell. Biol*. 101:560-567 (1985).

Soutschek, et al., "Therapeutic silencing of an endogenous gene by systemic administration of modified siRNAs", *Nature*, 432(7014):173-8 (2004).

Spector, "Higher order nuclear organization: Three-dimensional distribution of small nuclear ribonucleoprotein particles," *Proc. Natl. Acad. Sci*. 87:147-151 (1990).

Streisinger, et al., "Frameshift mutations and genetic code," *Cold Spring harbor Symp. Quant. Biol*. 31:77-84 (1966).

Strobel, et al., "Site-specific cleavage of human chromosome 4 mediated by triple-helix formation", *Science*, 254(5038):1639-42 (1991).

Summerton, et al., "Morpholino antisense oligomers: design, preparation, and properties", *Antisense Nucleic Acid Drug Dev.*, 7(3):187-95 (1997).

Sung, et al., "Recombination factors of *Saccharomyces cerevisiae*," *Mutat Res* 451:257-75 (2000).

Takasugi, et al., "Sequence-specific photo-induced cross-linking of the two strands of double-helical DNA by a psoralen covalently linked to a triple helix-forming oligonucleotide," *Proc. Natl. Acad. Sci. USA* 88:5602 (1991).

Talmadge, "The pharmaceutics and delivery of therapeutic polypeptides and proteins," *Adv. Drug. Del. Rev*. 10:247-299 (1993).

Thacker, "A surfeit of RAD51-like genes?," *Trends Genet* 15(5):166-8 (1999).

Thacker, "The photoprotective effect of ascorbic acid, acetylsalicylic acid, and indomethacin evaluated by the photo hen's egg test," *Trends Genet* 15(5): 166-8 (1999).

Thibodeau & Vincent, "Monoclonal Antibody CC-3 Recognizes Phosphorproteins in Interphase and Mitotic Cells," *Experimental Cell Research* 195: 145-153 (1991).

Towbin, et al., "Electrophoretic transfer of proteins from polyacrylamide gets to nitrocellulose sheets: Procedure and some applications," *Proc. Natl. Acad. Sci USA*., 76:4350-4354 (1979).

Uhlmann, et al., "Antisense Oligonucleotides: A New Therapeutic Principle," *Chem. Reviews* 90(4):544-584 (1990).

(56) References Cited

OTHER PUBLICATIONS

Vasquez, et al., "Chromosomal mutations induced by triple-forming oligonucleotides in mammalian cells," *Nucleic Acids Res.* 27: 1176 (1999).
Vasquez, et al., "Specific mutations induced by triplex-forming oligonucleotides in mice," *Science* 290: 530-533 (2000).
Wang, et al., "Cell killing by the *Drosophila* gene reaper," *Science* 271: 802 (1996).
Wang, et al., "Mutagenesis in mammalian cells induced by triple helix formation and transcription-coupled repair," *Science* 271:802-805 (1996).
Wang, et al., "Stimulation of intrachromosomal homologous recombination in human cells by electroporation with site-specific endonucleases," *Proc. Natl. Acad. Sci.* USA 93(8): 3608-12 (1996).
Wang, et al., "Targeted Mutagenesis in Mammalian Cells Mediated by Intracellular Triple Helix Formation," *Molecular and Cellular Biology*, 15(32\), 1759-1768 (1995).
Wang, et al., "Altered Repair of Targeted Psoralen Photoadducts in the Context of an Oligonucleotide-mediated Triple Helix" *J. Biol. Chem.* 270(22):22595-22601(1996).
Wansink, et al., "Fluorescent Labeling of Nascent RNA Reveals Transcription by RNA Polymerase II in Domains Scattered Throughout the Nucleus," *J. Cell. Biol.* 122:283-293 (1993).
Warren & Nelson, "Nonmitogenic Morphoregulatory Action of pp60.sup.v-src on Multicellular Epithelial Structures," *Mol. Cell. Biol.* 7:1326-1337 (1987).
Warren, et al., "Cytostellin: a novel highly conserved protein that undergoes continuous redistribution during the cell cycle," *J. Cell Sci.* 103:381-388 (1992).
Warren, et al., Coordinated Transcription-Dependent Redistribution, *Journal of Cellular Biochemistry*, Supplement 21B:141 (1995).
Whitesell, et al., "Stability, clearance, and disposition of intraventricularly administered oligodeoxynucleotides: implications for therapeutic application within the central nervous system," *Proc Natl Acad Sci U S A.* 90(10):4665-9 (1993).
Wood, et al., "Complementation of the xeroderma pigmentosum DNA repair defect in cell-free extracts," *Cell* 53:97 (1988).
Wood, et al., "The Effect of Volume and Temperature on the Energy and Entropy of Pure Liquids," *J. Am. Chem. Soc.* 79:2023 (1957).
Xing & Lawrence, "Higher Level Organization of Individual Gene Transcription and RNA Splicing," *Science* 259:1326-1330 (1993).
Yang, et al., "Nu-MA: An Unusually Long Coiled-Coil Related Protein in the Mammalian Nucleus," *J. Cell Biol.* 116:1303-1317 (1992).
Young, "Triple Helix Formation Inhibits Transcription Elongation in vitro," *Proc. Natl. Sci. USA* 88:10023 (1991).
Zendegui, et al., "In vivo stability and kinetics of absorption and disposition of 3' phosphopropyl amine oligonucleotides," *Nucleic Acids Res.* 20(2):307-17 (1992).
Zon & Geiser, "Phosphorothioate oligonucleotides: chemistry, purification, analysis, scale-up and future directions," *Anticancer Drug Des.* 6(6):539-68 (1991).
Belousov, et al., "Triplex targeting of a native gene in permeabilized intact cells: covalent modification of the gene for the chemokine receptor CCR5," *Nucleic Acids Res.*, 26(5):1324-8 (1998).
Gorman and Glazer, "Directed gene modification via triple helix formation," *Curr. Mol. Med.*, 1(3): 391-399 (2001).
Rogers, et al., "Site-directed recombination via bifunctional PNA-DNA conjugates," *Proc. Natl. Acad. Sci. U.S.A.*, 99(26): 16695-16700 (2002).
Bentin, et al., "Combined triplex/duplex invasion of double-stranded DNA by "tail-clamp" peptide nucleic acid", Biochemistry, 42(47):13987-95 (2003).
Chin, et al., "Correction of a splice-site mutation in the beta-globin gene stimulated by triplex-forming peptide nucleic acids", Proceedings of the Natl. Academy of Sciences of the US.,105(36):13514-19 (2008).
Kaihatsu, et al., "Extending recognition by peptide nucleic acids (PNAs): binding to duplex DNA and inhibition of transcription by tail-clamp PNA-peptide conjugates", Biochemistry, 42(47):13996-4003 (2003).

\* cited by examiner

FIG. 7

```
(g)cagtctatggacccctgatgttctctccctctcttctcatggctaagtcatgt catgaggaagggggagaagtaacaggt
cactcagatacccctggaactacaaaagggcaaaagagataccagtatccttccctctttcattgtccca
IVS2-1                                                         IVS2-64
acagttcagaatggaaacagacgaatgcatcagtggaaagtccaggatgtttagtcccttctatcctgcttgctgttcataa
tgtcaaatctcaccctttgtctgctacacgtagtcacaccttcaggagtcctagagtcctagagtcaaaatcaagaaatacttactaaagccaaagttatt caattgtttctttctgttcaatctctgcttctttcctcttctttctctcgcaattttactattttactaaagcctaacatgtg
gttaacaaaagaaacaaattaagaacgaaagaaaaaagaggggttaaaatgataatgatatacgaattacgaattgtaacac
                    IVS2-194
tataacaaaaggaaatatctgagatacattaagtaacttaacttacacagtctgcctagtacattactattggaa
atattgtttccttataagagactctcatgaatccattgaatttttttgaaatgtgtcagacggatcatgtaatgataaaactt tatatgtgtgcttattgcatatcataatctccctacttattctctttatttttcaattgatacaataatcattatacatattta
atatacacgaataaacgtatagtattagaggatgaaaataaaaattaactattattaatgtatttattgaaatatgtataaat tgggttaaagtgtaatgttctaatatgtacacatatattgaccaaatcagggtaattttgcatttgtaatttaaaaatgcttc
acccaattccacattacaaaatttatacacaacctgttagtcccattaaacgtaaacattaaaattttttacgaaag
                                                               IVS2-512
ttctctttaatatactttttgttctatcttatttctaatacactttcccctaatctcttctttcttcagggcaatgatacaatgtacca
aagaaaatatatgaaaaacaaaatagaaataaagattatgaaaagggatcagagaaagaagtcccgttattactatgttacatagt
                                        IVS2-566 IVS2-654
tgcctctttgcaccatttcaaagaataacagtgataatttctgggttaagc atagcaatatattctgcatataaatattctgca
acggagaaacgtggtaagattcctattgtcactattcctaaaagaccccttatcgttataagaagacgtatattataaagacgt
   IVS2-705                               IVS2-745
tataaaattgtaactgc taagaggttcatatagcagtacaatccag accattctgcttcttttattggtggg(SEQ ID NO:59)
atattaacattgactacatctccaaagtataacgattatcgtcgatggtcgatgtaagacgaaggaagtacaagtaccaaccc
ataaggctggattattctgagtccaagtcaggcccttttgctaatcatgttcatcctcttatcctcctccacag
tattccgacctaataagactcaggttcggatccgggaaaaacgatttagagaatatatggaaggagggtc(SEQ ID NO:60)
                                                  IVS2-830
```

MODIFIED TRIPLE-HELIX FORMING OLIGONUCLEOTIDES FOR TARGETED MUTAGENESIS

CROSS-REFERENCE TO RELATED APPLICATIONS

This application claims priority under 35 U.S.C. 119 to U.S. Ser. No. 60/739,740 filed Nov. 23, 2005.

STATEMENT REGARDING FEDERALLY SPONSORED RESEARCH OR DEVELOPMENT

This invention was made with government support under CA064186 awarded by National Institute of Health. The government has certain rights in the invention.

REFERENCE TO SEQUENCE LISTING

The Sequence Listing submitted Aug. 8, 2013 as a text file named "YU 4198_revised_ST25.txt" created on Aug. 5, 2013, and having a size of 29,714 bytes is hereby incorporated by reference.

BACKGROUND OF THE INVENTION

This relates to the field of genetics, and more particularly relates to site-directed mutagenesis of a gene of interest.

Since the initial observation of triple-stranded DNA many years ago by Felsenfeld et al., *J. Am. Chem. Soc.* 79:2023 (1957), oligonucleotide-directed triple helix formation has emerged as a valuable tool in molecular biology. Current knowledge suggests that oligonucleotides can bind as third strands of DNA in a sequence specific manner in the major groove in polypurine/polypyrimidine stretches in duplex DNA. In one motif, a polypyrimidine oligonucleotide binds in a direction parallel to the purine strand in the duplex, as described by Moser and Dervan, *Science* 238:645 (1987), Praseuth et al., *Proc. Natl. Acad. Sci. USA* 85:1349 (1988), and Mergny et al., *Biochemistry* 30:9791 (1991). In the alternate purine motif, a polypurine strand binds anti-parallel to the purine strand, as described by Beal and Dervan, *Science* 251:1360 (1991). The specificity of triplex formation arises from base triplets (AAT and GGC in the purine motif) formed by hydrogen bonding; mismatches destabilize the triple helix, as described by Mergny et al., *Biochemistry* 30:9791 (1991) and Beal and Dervan, *Nuc. Acids Res.* 11:2773 (1992).

Triplex forming oligonucleotides (TFOs) are useful for several molecular biology techniques. For example, triplex forming oligonucleotides designed to bind to sites in gene promoters have been used to block DNA binding proteins and to block transcription both in vitro and in vivo. (Maher et al., *Science* 245:725 (1989), Orson et al., *Nucleic Acids Res.* 19:3435 (1991), Postal et al., *Proc. Natl. Acad. Sci. USA* 88:8227 (1991), Cooney et al., *Science* 241:456 (1988). Young et al., *Proc. Natl. Acad. Sci. USA* 88:10023 (1991), Maher et al., *Biochemistry* 31:70 (1992), Duval-Valentin et al., Proc. Natl. Acad. Sci. USA 89:504 (1992), Blume et al., *Nucleic Acids Res.* 20:1777 (1992), Durland et al., *Biochemistry* 30:9246 (1991), Grigoriev et al., *J. of Biological Chem.* 267:3389 (1992), and Takasugi et al., *Proc. Natl. Acad. Sci. USA* 88:5602 (1991)). Site specific cleavage of DNA has been achieved by using triplex forming oligonucleotides linked to reactive moieties such as EDTA-Fe(II) or by using triplex forming oligonucleotides in conjunction with DNA modifying enzymes (Perrouault et al., *Nature* 344:358 (1990), Francois et al., *Proc. Natl. Acad. Sci. USA* 86:9702 (1989), Lin et al., *Biochemistry* 28:1054 (1989), Pei et al., *Proc. Natl. Acad. Sci. USA* 87:9858 (1990), Strobel et al., *Science* 254:1639 (1991), and Posvic and Dervan, *J. Am. Chem Soc.* 112:9428 (1992)). Sequence specific DNA purification using triplex affinity capture has also been demonstrated (Ito et al., *Proc. Natl. Acad. Sci. USA* 89:495 (1992)). Triplex forming oligonucleotides linked to intercalating agents such as acridine, or to crosslinking agents, such as p-azidophenacyl and psoralen, have been utilized, but only to enhance the stability of triplex binding. (Praseuth et al., *Proc. Natl. Acad. Sci. USA* 85:1349 (1988), Grigoriev et al., *J. of Biological Chem.* 267:3389 (1992), Takasugi et al., *Proc. Natl. Acad. Sci. USA* 88:5602 (1991).

Gene therapy can be defined by the methods used to introduce heterologous DNA into a host cell or by the methods used to alter the expression of endogenous genes within a cell. As such, gene therapy methods can be used to alter the phenotype and/or genotype of a cell.

Targeted modification of the genome by gene replacement is of value as a research tool and in gene therapy. However, while facile methods exist to introduce new genes into mammalian cells, the frequency of homologous integration is limited (Hanson et al., (1995) Mol. Cell. Biol. 15(1), 45-51), and isolation of cells with site-specific gene insertion typically requires a selection procedure (Capecchi, M. R., (1989), Science 244(4910), 1288-1292). Site-specific DNA damage in the form of double-strand breaks produced by rare cutting endonucleases can promote homologous recombination at chromosomal loci in several cell systems, but this approach requires the prior insertion of the recognition sequence into the locus.

Methods which alter the genotype of a cell typically rely on the introduction into the cell of an entire replacement copy of a defective gene, a heterologous gene, or a small nucleic acid molecule such as an oligonucleotide, to treat human, animal and plant genetic disorders. The introduced gene or nucleic acid molecule, via genetic recombination, replaces the endogenous gene. This approach requires complex delivery systems to introduce the replacement gene into the cell, such as genetically engineered viruses, or viral vectors.

Alternatively, gene therapy methods can be used to alter the expression of an endogenous gene. One example of this type of method is antisense therapy. In antisense therapy a nucleic acid molecule is introduced into a cell, the nucleic acid molecule being of a specific nucleic acid sequence so as to hybridize or bind to the mRNA encoding a specific protein. The binding of the antisense molecule to an mRNA species decreases the efficiency and rate of translation of the mRNA.

Gene therapy is being used on an experimental basis to treat well known genetic disorders of humans such as retinoblastoma, cystic fibrosis, and globinopathies such as sickle cell anemia. However, in vivo efficiency is low due to the limited number of recombination events actually resulting in replacement of the defective gene.

A method for targeted mutagenesis of a target DNA molecule would be useful as another means of gene therapy which can be carried out in vivo. Such a method would also be a useful research tool for genetic engineering or for studying genetic mechanisms such as DNA repair.

Therefore, it is an object of the present invention to provide a method for in vivo and in vitro targeted mutagenesis of a target DNA molecule.

It is a further object of the present invention to provide a method for in vivo and in vitro targeted recombination, wherein previous modification of the target is not required.

It is a further object of the present invention to use triplex forming oligonucleotides (TFOs) to promote and increase the frequency of recombination resulting in a targeted genetic change.

It is a further object of the present invention to use TFOs to promote targeted genetic changes in human and animal cells.

It is a further object of the present invention to provide a method for mutagenesis of a target DNA molecule that is highly specific and efficient.

It is a further object of the present invention to provide a method for treating genetic disorders by gene therapy without the need for a viral vector.

It is a further object of the present invention to provide a method for treating cancer.

It is a further object of the present invention to provide a method for treating globinopathies, including sickle cell anemia and thalassemia.

It is a further object of the present invention to provide oligonucleotides for use in therapy and research.

SUMMARY OF THE INVENTION

High affinity, chemically modified triplex-forming oligonucleotides (TFOs) and methods for use thereof are disclosed. TFOs are defined as triplex-forming oligonucleotides which bind as third strands to duplex DNA in a sequence specific manner. Triplex-forming oligonucleotides may be comprised of any possible combination of nucleotides and modified nucleotides. Modified nucleotides may contain chemical modifications of the heterocyclic base, sugar moiety of phosphate moiety. A high affinity oligonucleotide ($K_d \leq 2 \times 10^{-8}$) which forms a triple strand with a specific DNA segment of a target gene DNA is generated. It is preferable that the $K_d$ for the high affinity of oligonucleotide is less than or equal to $2 \times 10^{-6}$. It is more preferable that the $K_d$ fore the high affinity oligonucleotide is less than or equal to $2 \times 10^{-7}$. It is still more preferable that the $K_d$ for the high affinity of oligonucleotide be below $2 \times 10^{-8}$. It is still more preferable that the the $K_d$ for the high affinity oligonucleotide be below $2 \times 10^{-9}$. It is even more preferable that the $K_d$ for the high affinity of oligonucleotide be below $2 \times 10^{-10}$. The oligonucleotide binds or hybridizes to a target sequence within a target gene or target region of a chromosome, forming a triplex region. The binding of the oligonucleotide to the target region stimulates mutations within or adjacent to the target region using cellular DNA synthesis, recombination, and repair mechanisms. The mutation generated activates, inactivates, or alters the activity and function of the target gene.

The examples demonstrate the effect of several chemical modifications. A series of pyrimidine and purine TFOs were characterized, containing adjacent cytosines or 5 methylcytosines (5-MeC), with different base, sugar, and backbone modifications. The base modification was 5-(1-propynyl)-2'-guanidoethyl (2'-OGE) (Prakash, 2004 5567), 2'-O,4'-C-methylene ribose (LNA) {Obika, 2001 3440) (Jepsen, 2004 5545), 2'-O-(2-methoxyethyl) (2'-OME) (Lind, 1998 1817), 2'-O—(N-(methyl)acetamido) (Pattanayek, 2004 5566), morpholino (Summerton, 1997 371), 2'-O-methyl (2'-OME), and 2'-aminoethoxy (2'-AE) (Cuenoud, 1998 1822). The backbone modification was the non bridging phosphate derivative, diethylethlenediamine (DEED) (Dagle, 1996 1502). Several modifications were demonstrated to greatly enhance stability of the resulting triplex. In another example the donor nucleic acid is single stranded or double stranded and contains one or more phosphorothioate internucleoside linkages which enhance stability.

BRIEF DESCRIPTION OF THE DRAWINGS

FIG. 7 shows the sequence of the wild-type intron 2 (IVS2) sequence of the human β-globin gene. The sequence shows six polypurine runs suitable for potential targeting by triplex forming oligonucleotides. These sites are boxed. The circled nucleotides represent various β-thalassemia-associated point mutations.

DETAILED DESCRIPTION OF THE INVENTION

I. Compositions

A. Triplex-forming Oligonucleotides (TFOs)

Figure 1:
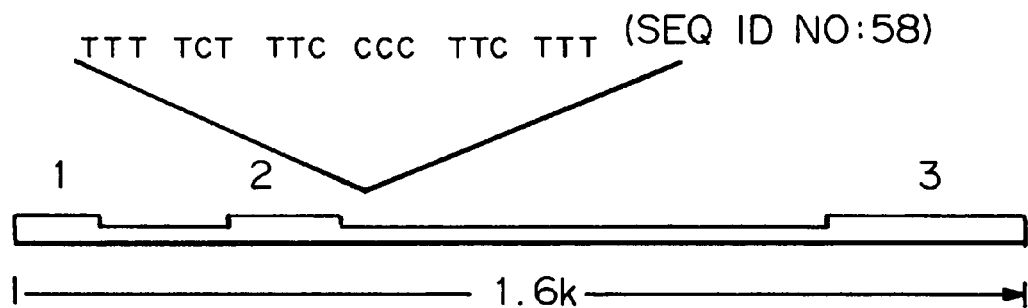
FIG. 1 shows the organization of the human β-globin gene and the sequence of the triplex target in intron 2.

Triplex-forming oligonucleotides (TFOs) are defined as oligonucleotides which bind as third strands to duplex DNA in a sequence specific manner. The oligonucleotides are synthetic or isolated nucleic acid molecules which selectively bind to or hybridize with a predetermined region of a double-stranded DNA molecule so as to form a triple-stranded structure. The predetermined region is referred to herein as the target sequence, target region, or target site.

Preferably, the target region of the double-stranded molecule contains or is adjacent to a defective or essential portion of a target gene, such as the site of a mutation causing a genetic defect, a site causing oncogene activation, or a site causing the inhibition or inactivation of an oncogene suppressor. More preferably, the gene is a human gene. In a preferred embodiment, the gene is human β-globin.

Preferably, the oligonucleotide is a single-stranded nucleic acid molecule between 7 and 40 nucleotides in length, most preferably 10 to 20 nucleotides in length for in vitro mutagenesis and 20 to 30 nucleotides in length for in vivo mutagenesis. The base composition may be homopurine or homopyrimidine. Alternatively, the base composition may be polypurine or polypyrimidine. However, other compositions are also useful.

The oligonucleotides are preferably generated using known DNA synthesis procedures. In the examples that follow, the oligonucleotides were obtained from a commercial supplier and were chemically modified where indicated by standard methods that are well known in the art.

The nucleotide sequence of the oligonucleotides is selected based on the sequence of the target sequence, the physical constraints imposed by the need to achieve binding of the oligonucleotide within the major groove of the target region, and the need to have a low dissociation constant ($K_d$) for the oligonucleotide/target sequence. The oligonucleotides will have a base composition which is conducive to triple-helix formation and will be generated based on one of the known structural motifs for third strand binding. The most stable complexes are formed on polypurine:polypyrimidine elements, which are relatively abundant in mammalian genomes. Triplex formation by TFOs can occur with the third strand oriented either parallel or anti-parallel to the purine strand of the duplex. In the anti-parallel, purine motif, the triplets are G.G:C and A.A:T, whereas in the parallel pyrimidine motif, the canonical triplets are $C^+$.G:C and T.A:T. The triplex structures are stabilized by two Hoogsteen hydrogen bonds between the bases in the TFO strand and the purine strand in the duplex. A review of base compositions for third strand binding oligonucleotides is provided in U.S. Pat. No. 5,422,251.

Preferably, the oligonucleotide binds/hybridize to the target nucleic acid molecule under conditions of high stringency and specificity. Most preferably, the oligonucleotides bind in a sequence-specific manner within the major groove of duplex DNA. Reaction conditions for in vitro triple helix formation of an oligonucleotide probe or primer to a nucleic acid sequence vary from oligonucleotide to oligonucleotide, depending on factors such as oligonucleotide length, the number of G:C and A:T base pairs, and the composition of the buffer utilized in the hybridization reaction. An oligonucleotide substantially complementary, based on the third strand binding code, to the target region of the double-stranded nucleic acid molecule is preferred.

As used herein, an oligonucleotide is said to be substantially complementary to a target region when the oligonucleotide has a base composition which allows for the formation of a triple-helix with the target region. As such, an oligonucleotide is substantially complementary to a target region even when there are non-complementary bases present in the oligonucleotide. As stated above, there are a variety of structural motifs available which can be used to determine the nucleotide sequence of a substantially complementary oligonucleotide.

The preferred conditions under which a triple-stranded structure will form are standard assay conditions for in vitro mutagenesis and physiological conditions for in vivo mutagenesis. (See for example, Moser and Dervan, *Science* 238:645 (1987); Praseuth et al., *Proc. Natl. Acad. Sci.* USA 85:1349 (1988); Mergny et al., *Biochemistry* 30:9791 (1991); Beal and Dervan, *Science* 251:1360 (1991); Mergny et al., *Biochemistry* 30:9791 (1991) and Beal and Dervan, *Nuc. Acids Res.* 11:2773 (1992).

A useful measure of triple helix formation is the equilibrium dissociation constant, $K_d$, of the triplex, which can be estimated as the concentration of oligonucleotide at which triplex formation is half-maximal. Preferably, the oligonucleotide has a binding affinity for the target sequence in the range of physiologic interactions. The preferred oligonucleotide has a $K_d$ less than or equal to approximately $10^{-7}$ M. Most preferably, the $K_d$ is less than or equal to $2 \times 10^{-8}$ M in order to achieve significant intramolecular interactions.

A variety of methods are available to determine the $K_d$ of an oligonucleotide/target pair. In the Examples which follow, the $K_d$ was estimated using a gel mobility shift assay (R. H. Durland et al., *Biochemistry* 30, 9246 (1991)). In one example below using this method, two complementary oligonucleotides containing the sequence corresponding to bp 11 to 56 of the second intron of the human β-globin gene were annealed to make a duplex containing a TFO target site. The annealed oligonucleotide was end-labeled with $\alpha$-$[P^{32}]$-ATP and T4 polynucleotide kinase, gel purified, and incubated overnight (approximately 18-24 hours) at 37° C. with increasing concentrations of TFO. The reactions were then subjected to gel electrophoresis in a 12% non-denaturing polyacrylamide (19:1 acrylamide:bisacrylamide) gel containing 89 mM Tris, 89 mM boric acid, pH 7.2, and 10 mM $MgCl_2$ (for pH 7.2 conditions) using a BioRad Mini PROTEAN 3 apparatus for ~4 hours at 65V. For pH 5.6 conditions, 12% non-denaturing gels contained 50 mM MES, pH 5.6, and 10 mM $MgCl_2$ and were run on a larger BioRad PROTEAN II xi cell apparatus for ~7 hours at 270V. The gels were then dried and visualized by autoradiography. The dissociation constant ($K_d$) was determined to be the concentration of TFO in which half was bound to the duplex and half was unbound.

Chemical Modifications

As used herein, an "oligonucleotide" is a nucleic acid polymer comprising a plurality of nucleotide subunits of defined base sequence. Oligonucleotides comprise a chain of nucleotides which are linked to one another by phosphate ester linkages. Each nucleotide typically comprises a heterocyclic base (nucleic acid base), a sugar moiety attached to the heterocyclic base, and a phosphate moiety which esterifies a hydroxyl function of the sugar moiety. The principal naturally-occurring nucleotides comprise uracil, thymine, cytosine, adenine and guanine as the heterocyclic bases, and ribose or deoxyribose as the sugar moiety. As used herein, oligonucleotide also includes polynucleotides.

As described in the Examples that follow, modified bases and base analogues, modified sugars and sugar analogues and/or phosphate analogues and modified phosphate moieties, known in the art, are also suitable for use in triplex-forming oligonucleotides. Under physiologic conditions, potassium levels are high, magnesium levels are low, and pH is neutral. These conditions are generally unfavorable to allow for effective binding of TFOs to duplex DNA. For example, high potassium promotes guanine (G)-quartet formation, which inhibits the activity of G-rich purine motif TFOs. Also, magnesium, which is present at low concentrations under physiologic conditions, supports third-strand binding by charge neutralization. Finally, neutral pH disfavors cytosine protonation, which is needed for pyrimidine motif third-strand binding. Target sequences with adjacent cytosines are particularly problematic. Triplex stability is greatly compromised by runs of cytosines, thought to be due to repulsion between the positive charge resulting from the $N^3$ protonation or perhaps because of competition for protons by the adjacent cytosines.

Chemical modification of nucleotides comprising TFOs may be useful to increase binding affinity of TFOs and/or triplex stability under physiologic conditions. Modified nucleotides may comprise one or more of the nucleotides which comprise a triplex-forming oligonucleotide. As used herein "modified nucleotide" or "chemically modified nucleotide" defines a nucleotide that has a chemical modification of one or more of the hetrocyclic base, sugar moiety or phosphate moiety constituents. Preferably, modified oligonucleotides in TFOs are able to form Hoogsteen and/or reverse Hoogsteen base pairs with bases of the duplex target DNA. More preferably, modified oligonucleotides increase the binding affinity of the TFO to the target duplex DNA, or the stability of the formed triplex.

Chemical modifications of hetrocyclic bases or heterocyclic base analogs may be effective to increase the binding affinity of a nucleotide or its stability in a triplex. Chemically-modified heterocyclic bases include, but are limited to, inosine, 5-(1-propynyl) uracil (pU), 5-(1-propynyl) cytosine (pC), 5-methylcytosine, 8-oxo-adenine, pseudocytosine, pseudoisocytosine, 5 and 2-amino-5-(2'-deoxy-β-D-ribofuranosyl)pyridine (2-aminopyridine), and various pyrrolo- and pyrazolopyrimidine derivatives. Substitution of 5-methylcytosine for cytosine in TFOs helps to stabilize triplex formation at neutral pH, especially in TFOs with isolated cytosines. This is because the positive charge partially reduces the negative charge repulsion between the TFO and the target duplex. As shown in the examples that follow, substitutions of 2'-O-methylpseudocytidine for cytidine are especially useful to stabilize triplexes formed by TFOs and target duplexes when the target sequence contains adjacent cytidines.

Triplex-forming oligonucleotides may also contain nucleotides with modified sugar moieties or sugar moiety analogs. Sugar moiety modifications include, but are not limited to, 2'-O-aminoetoxy, 2'-O-amonioethyl (2'-OAE), 2'-O-methoxy, 2'-O-methyl, 2-guanidoethyl (2'-OGE), 2'-O,4'-C-methylene (LNA), 2'-O-(methoxyethyl) (2'-OME) and 2'-O—(N-(methyl)acetamido) (2'-OMA), 2'-O-aminoethyl sugar moiety substitutions are especially preferred because they are protonated at neutral pH and thus suppress the charge repulsion between the TFO and the target duplex. This modification stabilizes the C3'-endo conformation of the ribose or dexyribose and also forms a bridge with the i-l phosphate in the purine strand of the duplex.

Modifications to the phosphate backbone of triplex-forming oligonucleotides may also increase the binding affinity of TFOs or stabilize the triplex formed between the TFO and the target duplex. Cationic modifications, including, but not limited to, diethyl-ethylenediamide (DEED) or dimethyl-aminopropylamine (DMAP) may be especially useful due to decrease electrostatic repulsion between TFO and duplex target phosphates.

Peptide nucleic acids (PNAs) are molecules in which the phosphate backbone backbone of oligonucleotides is replaced by repeating N-(2-aminoethyl)-glycine units and phosphodiester bonds are replaced by peptide bonds. The various heterocyclic bases are linked to the backbone by methylene carbonyl bonds. As used herein, peptide nucleic acids are defined as modified oligonucleotides. Peptide nucleic acids are comprised of peptide nucleic acid monomers. As used herein, a peptide nucleic acid monomer is defined as a modified nucleotide. Two PNAs may be linked together to form a bis-PNA molecule that forms a triplex "clamp" with one of the strands of the target duplex while displacing the other strand of the duplex target. The neutral backbone of PNAs decreases electrostatic repulsion between TFO and duplex target phosphates.

Modifications of the phosphate backbone may also include the substitution of a sulfur atom for one of the non-bridging oxygens in the phosphodiester linkage. This substitution creates a phosphorothioate internucleoside linkage in place of the phosphodiester linkage. Oligonucleotides containing phosphorothioate internucleoside linkages have been shown to be more stable in vivo.

Oligonucleotides may further be modified to be end capped to prevent degradation using a 3'propylamine group. Procedures for 3' or 5' capping oligonucleotides are well known in the art.

Formulations of the oligonucleotides embrace fusions of the oligonucleotides or modifications of the oligonucleotides, wherein the oligonucleotide is fused to another moiety or moieties, e.g., targeting moiety or another therapeutic agent. Such analogs may exhibit improved properties such as increased cell membrane permeability, activity and/or stability. Examples of moieties which may be linked or unlinked to the oligonucleotides include, for example, targeting moieties which provide for the delivery of oligonucleotides to specific cells, e.g., antibodies to red blood cells, immune cells, lung cells or any other preferred cell type, as well as receptor and ligands expressed on the preferred cell type. Preferably, the moieties target red blood cells. Other moieties that may be provided with the oligonucleotides include protein transduction domains (PTDs), which are short basic peptide sequences present in many cellular and viral proteins that mediate translocation across cellular membranes. Example protein transduction domains that are well-known in the are include for Antennapedia PTD and the TAT (transactivator of transcription) PTD.

B. Donor Oligonucleotides

The triplex forming oligonucleotides (TFOs) may be administered in combination with, or tethered to a donor oligonucleotide via a mixed sequence linker or used in conjunction with a non-tethered donor oligonucleotide that is homologous to the target sequence. Donor oligonucleotides are also referred to herein as donor fragments, donor nucleic acids, donor DNA, or donor DNA fragments. This strategy is intended to exploit the ability of a triplex, itself, to provoke DNA repair, potentially increasing the probability of recombination with the homologous donor DNA. It is understood in the art that a greater number of homologous positions within the donor fragment will increase the probability that the donor fragment will be recombined into the target sequence, target region, or target site. Tethering of a donor oligonucleotide to a TFO facilitates target site recognition via triple helix formation while at the same time positioning the tethered donor fragment for possible recombination and information transfer. As demonstrated in the examples that follow, TFOs also effectively induce homologous recombination of non-tethered donor oligonucleotides. The term "recombinagenic" as used herein, is used to define a DNA fragment, oligonucleotide, or composition as being able to recombine into a target site or sequence or induce recombination of another DNA fragment, oligonucleotide, or composition.

Non-tethered, or unlinked fragments may range in length from 30 nucleotides to several thousand. It is to be understood that the donor oligonucleotide molecules, whether linked or unlinked, can exist in single stranded or double stranded form. It is to be understood that the donor fragment to be recombined can be linked or un-linked to the triplex forming oligonucleotide. The linked donor fragment may range in length from 4 nucleotides to 50 nucleotides. However, the unlinked donor fragments have a much broader range: from 30 nucleotides to several thousand. It is preferable that the triplex forming recombinagenic oligonucleotide is at least 10 nucleotides in length. It is more preferable that the oligonucleotide be at least 20 nucleotides in length. It is still more preferable that the oligonucleotide be between 30 and 60 nucleotides in length.

II. Methods of Use

Triplex-forming oligonucleotides bind/hybridize to a target sequence within a target gene or target region of a chromosome, forming a triplex region. The binding of the oligonucleotide to the target region stimulates mutations within or adjacent to the target region using cellular DNA synthesis, recombination, and repair mechanisms. The mutation generated activates, inactivates, or alters the activity and function of the target gene.

If the target gene contains a mutation that is the cause of a genetic disorder, then the oligonucleotide is useful for mutagenic repair that restores the DNA sequence of the target gene to normal. If the target gene is a viral gene needed for viral survival or reproduction or an oncogene causing unregulated proliferation, such as in a cancer cell, then the mutagenic oligonucleotide is useful for causing a mutation that inactivates the gene to incapacitate or prevent reproduction of the virus or to terminate or reduce the uncontrolled proliferation of the cancer cell. The mutagenic oligonucleotide is also a useful anti-cancer agent for activating a repressor gene that has lost its ability to repress proliferation.

The triplex-forming oligonucleotide is also particularly useful as a molecular biology research tool to cause targeted mutagenesis. Targeted mutagenesis has been shown to be a very useful tool when employed to not only elucidate functions of genes and gene products, but alter known activities of genes and gene products as well. Targeted mutagenesis is also useful for targeting a normal gene and for the study of mechanisms such as DNA repair. Targeted mutagenesis of a specific gene in an animal oocyte, such as a mouse oocyte, provides a useful and powerful tool for genetic engineering for research and therapy and for generation of new strains of "transmutated" animals and plants for research and agriculture.

The induction of targeted recombination may be best served, for example, to correct a mutation in a target gene that is the cause of a genetic disorder. Alternatively, if the target gene is a viral gene needed for viral survival or reproduction or an oncogene causing unregulated proliferation, such as in a cancer cell, then the use of recombinagenic TFOs should be useful for inducing a mutation or correcting the mutation, by homologous recombination, thereby inactivating the gene to incapacitate or prevent reproduction of the virus or to terminate or reduce the uncontrolled proliferation of the cancer cell.

The oligonucleotides can be used alone or in combination with other mutagenic agents. As used herein, two agents are said to be used in combination when the two agents are co-administered, or when the two agents are administered in a fashion so that both agents are present within the cell or serum simultaneously. A preferred agent for co-administration is psoralen-linked oligonucleotides as described in PCT/US94/07234 by Yale University.

The oligonucleotides can further be used to stimulate homologous recombination of an exogenously supplied, donor oligonucleotide, into a target region. Specifically, by activating cellular mechanisms involved in DNA synthesis, repair and recombination, the triplex-forming oligonucleotides can be used to increase the efficiency of targeted recombination.

In targeted recombination, a triplex forming oligonucleotide is administered to a cell in combination with a separate donor fragment which minimally contains a sequence complementary to the target region or a region adjacent to the target region, referred to herein as the donor fragment. The donor fragment can further contain nucleic acid sequences which are to be inserted within the target region. The co-administration of a triplex forming oligonucleotide with the fragment to be recombined increases the frequency of insertion of the donor fragment within the target region when compared to procedures which do not employ a triplex forming oligonucleotide.

A. Methods of Use as Molecular Research Tools

For in vitro research studies, a solution containing the triplex-forming oligonucleotides is added directly to a solution containing the DNA molecules of interest in accordance with methods well known to those skilled in the art and described in more detail in the examples below.

In vivo research studies are conducted by transfecting cells with the triplex-forming oligonucleotide in a solution such as growth media with the transfected cells for a sufficient amount of time for entry of the TFO into the cells for triplex formation with a target duplex sequence. The target duplex sequence may be episomal DNA, such as nonintegrated plasmid DNA. The target duplex sequence may also be exogenous DNA, such as plasmid DNA or DNA from a viral construct, which has been integrated into the cell's chromosomes. The target duplex sequence may also be a sequence endogenous to the cell. The transfected cells may be in suspension or in a monolayer attached to a solid phase, or may be cells within a tissue wherein the oligonucleotide is in the extracellular fluid.

B. Methods of Use for Treatment or Prevention

Conditions to be Treated

The relevance of DNA repair and mediated recombination as gene therapy is apparent when studied in the context of human genetic diseases, for example, cystic fibrosis, hemophelia, globinopathies such as sickle cell anemia and beta-thalassemia, and xeroderma pigmentosum. If the target gene contains a mutation that is the cause of a genetic disorder, then the oligonucleotide is useful for mutagenic repair that may restore the DNA sequence of the target gene to normal.

Targeted DNA repair and recombination induced by triplex-forming oligonucleotides is especially useful to treat genetic deficiencies, disorders and diseases caused by mutations in single genes. TFOs are also especially useful to correct genetic deficiencies, disorders and diseases caused by point mutations.

Worldwide, globinopathies account for significant morbidity and mortality. Over 1,200 different known genetic mutations affect the DNA sequence of the human alpha-like (HBZ, HBA2, HBA1, and HBQ1) and beta-like (HBE1, HBG1, HBD, and HBB) globin genes. Two of the more prevalent and well-studied globinopathies are sickle cell anemia and β-thalassemia. Substitution of valine for glutamic acid at position 6 of the β-globin chain in patients with sickle cell anemia predisposes to hemoglobin polymerization, leading to sickle cell rigidity and vasoocclusion with resulting tissue and organ damage. In patients with β-thalassemia, a variety of mutational mechanisms results in reduced synthesis of β-globin leading to accumulation of aggregates of unpaired, insoluble α-chains that cause ineffective erythropoiesis, accelerated red cell destruction, and severe anemia.

All together, globinopathies represent the most common single-gene disorders in man. Triplex forming oligonucleotides are particularly well suited to treat globinopathies, as they are single gene disorders caused by point mutations. The examples that follow demonstrate that TFOs disclosed herein are effective at binding to the human β-globin both in vitro and in living cells. The examples further demonstrate, using a reporter based system in living cells, that TFOs targeted to specific target sites in the human β-globin gene effectively induce repair of known mutations when co-administered with appropriate donor oligonucleotides.

Xeroderma pigmentosum (XP) is a rare, autosomal recessive disease that exhibits its influence worldwide, with a frequency of about 1 in 250,000 in the U.S. and Europe, and roughly 1 in 40,000 in Japan. Patients diagnosed with the disease are hypersensitive to the UV component of sunlight and less than 40% will live beyond the age of 20. This hypersensitivity manifests in numerous skin and eye lesions including cancers. XP was first described in 1874 by Hebra and Kaposi. In 1882, Kaposi named the condition "xeroderma pigmentosum", referring to its characteristic dry, pigmented skin and was the first to point out the hereditary nature of the disease, noting that two patients were siblings. XP is characterized by photosensitivity, pigmentary changes, premature skin aging and the development of malignant tumors.

Cells from XP patients are unable to correctly respond to DNA damage caused by UV light. In normal functioning cells, mutations in DNA caused by UV and other common mutagens may be removed by the nucleotide excision repair pathway (NER) in mammalian cells. Briefly, the pathway involves removing the damaged nucleotides from the double-stranded DNA, and converting the resulting single-stranded DNA back to double-strandedness via the action of DNA polymerases, using the non-damaged strand as a template, and DNA ligase.

Nucleotide excision repair is strikingly similar in *E. coli* and mammals. UV sensitivity is the result of mutations in any of the genes involved in this type of repair in humans, including XP-A through XP-I and XP-V, and in any of the uvrA, uvrB, and uvrC genes in *E. coli*. UV mimetic compounds such as psoralen, cisplatin, mitomycin-C, benzo[a]pyrene and 4-nitroquinolone oxide can affect the enzymatic action of the gene encoded repair products mentioned above.

If the target gene is an oncogene causing unregulated proliferation, such as in a cancer cell, then the oligonucleotide is useful for causing a mutation that inactivates the gene and terminates or reduces the uncontrolled proliferation of the cell. The oligonucleotide is also a useful anti-cancer agent for activating a repressor gene that has lost its ability to repress proliferation.

The oligonucleotide is useful as an antiviral agent when the oligonucleotide is specific for a portion of a viral genome necessary for proper proliferation or function of the virus.

Formulations

The compounds are preferably employed for therapeutic uses in combination with a suitable pharmaceutical carrier. Such compositions comprise an effective amount of the compound, and a pharmaceutically acceptable carrier or excipient. The formulation is made to suit the mode of administration. Pharmaceutically acceptable carriers are determined in part by the particular composition being administered, as well as by the particular method used to administer the composition. Accordingly, there is a wide variety of suitable formulations of pharmaceutical compositions containing the nucleic acids some of which are.

It is understood by one of ordinary skill in the art that nucleotides administered in vivo are taken up and distributed to cells and tissues (Huang, et al., *FEBS Lett.* 558(1-3):69-73 (2004)). For example, Nyce et al. have shown that antisense oligodeoxynucleotides (ODNs) when inhaled bind to endogenous surfactant (a lipid produced by lung cells) and are taken up by lung cells without a need for additional carrier lipids (Nyce and Metzger, *Nature,* 385:721-725 (1997). Small nucleic acids are readily taken up into T24 bladder carcinoma tissue culture cells (Ma, et al., *Antisense Nucleic Acid Drug Dev.* 8:415-426 (1998).

The compounds may be in a formulation for administration topically, locally or systemically in a suitable pharmaceutical carrier. Remington's Pharmaceutical Sciences, 15th Edition by E. W. Martin (Mark Publishing Company, 1975), discloses typical carriers and methods of preparation. The compound may also be encapsulated in suitable biocompatible microcapsules, microparticles or microspheres formed of biodegradable or non-biodegradable polymers or proteins or liposomes for targeting to cells. Such systems are well known to those skilled in the art an may be optimized for use with the appropriate nucleic acid.

Various methods for nucleic acid delivery are described, for example, in Sambrook et al., 1989, *Molecular Cloning: A Laboratory Manual*, Cold Spring Harbor Laboratory, New York; and Ausubel et al., 1994, *Current Protocols in Molecular Biology*, John Wiley & Sons, New York. Such nucleic acid delivery systems comprise the desired nucleic acid, by way of example and not by limitation, in either "naked" form as a "naked" nucleic acid, or formulated in a vehicle suitable for delivery, such as in a complex with a cationic molecule or a liposome forming lipid, or as a component of a vector, or a component of a pharmaceutical composition. The nucleic acid delivery system can be provided to the cell either directly, such as by contacting it with the cell, or indirectly, such as through the action of any biological process. The nucleic acid delivery system can be provided to the cell by endocytosis, receptor targeting, coupling with native or synthetic cell membrane fragments, physical means such as electroporation, combining the nucleic acid delivery system with a polymeric carrier such as a controlled release film or nanoparticle or microparticle, using a vector, injecting the nucleic acid delivery system into a tissue or fluid surrounding the cell, simple diffusion of the nucleic acid delivery system across the cell membrane, or by any active or passive transport mechanism across the cell membrane. Additionally, the nucleic acid delivery system can be provided to the cell using techniques such as antibody-related targeting and antibody-mediated immobilization of a viral vector.

Formulations for topical administration may include ointments, lotions, creams, gels, drops, suppositories, sprays, liquids and powders. Conventional pharmaceutical carriers, aqueous, powder or oily bases, or thickeners can be used as desired.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions, solutions or emulsions that can include suspending agents, solubilizers, thickening agents, dispersing agents, stabilizers, and preservatives. Formulations for injection may be presented in unit dosage form, e.g., in ampules or in multi-dose containers, with an added preservative. The compositions may take such forms as sterile aqueous or nonaqueous solutions, suspensions and emulsions, which can be isotonic with the blood of the subject in certain embodiments. Examples of nonaqueous solvents are polypropylene glycol, polyethylene glycol, vegetable oil such as olive oil, sesame oil, coconut oil, arachis oil, peanut oil, mineral oil, injectable organic esters such as ethyl oleate, or fixed oils including synthetic mono or diglycerides. Aqueous carriers include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, and electrolyte replenishers (such as those based on Ringer's dextrose). Preservatives and other additives may also be present such as, for example, antimicrobials, antioxidants, chelating agents and inert gases. In addition, sterile, fixed oils are conventionally employed as a solvent or suspending medium. For this purpose any bland fixed oil including synthetic mono- or diglycerides may be employed. In addition, fatty acids such as oleic acid may be used in the preparation of injectables. Carrier formulation can be found in Remington's Pharmaceutical Sciences, Mack Publishing Co., Easton, Pa. Those of skill in the art can readily determine the various parameters for preparing and formulating the compositions without resort to undue experimentation.

The compound alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and air. For administration inhalation, the compounds are delivered in the form of an aerosol spray presentation from pressurized packs or a nebulizer, with the use of a suitable propellant.

In some embodiments, the compound described above may include pharmaceutically acceptable carriers with formulation ingredients such as salts, carriers, buffering agents, emulsifiers, diluents, excipients, chelating agents, fillers drying agents, antioxidants, antimicrobials, preservatives, binding agents, bulking agents, silicas, solubilizers, or stabilizers. In one embodiment, the compounds are conjugated to lipophilic groups like cholesterol and lauric and lithocholic acid derivatives with C32 functionality to improve cellular uptake. For example, cholesterol has been demonstrated to enhance uptake and serum stability of siRNA in vitro (Lorenz, et al., *Biorg. Med. Chem. Lett.* 14(19):4975-4977 (2004)) and in vivo (Soutschek, et al., *Nature* 432(7014):173-178 (2004)). In addition, it has been shown that binding of steroid conjugated oligonucleotides to different lipoproteins in the bloodstream, such as LDL, protect integrity and facilitate biodistribution (Rump, et al., *Biochem. Pharmacol.* 59(11):1407-1416 (2000)). Other groups that can be attached or conjugated to the compound described above to increase cellular uptake, include acridine derivatives; cross-linkers such as psoralen derivatives, azidophenacyl, proflavin, and azidoproflavin; artificial endonucleases; metal complexes such as EDTA-Fe (II) and porphyrin-Fe(II); alkylating moieties; nucleases such as alkaline phosphatase; terminal transferases; abzymes; cholesteryl moieties; lipophilic carriers; peptide conjugates; long chain alcohols; phosphate esters; radioactive markers; non-radioactive markers; carbohydrates; and polylysine or other polyamines. U.S. Pat. No. 6,919,208 to Levy, et al., also describes methods for enhanced delivery. These pharmaceutical formulations may be manufactured in a manner that is itself known, e.g., by means of conventional mixing, dissolving, granulating, levigating, emulsifying, encapsulating, entrapping or lyophilizing processes.

Methods of Administration

In general, methods of administering compounds, including oligonucleotides and related molecules, are well known in the art. In particular, the routes of administration already in use for nucleic acid therapeutics, along with formulations in current use, provide preferred routes of administration and formulation for the oligonucleotides described above. Preferably the oligonucleotides are injected into the organism undergoing genetic manipulation, such as an animal requiring gene therapy or anti-viral therapeutics.

Compositions can be administered by a number of routes including, but not limited to: oral, intravenous, intraperitoneal, intramuscular, transdermal, subcutaneous, topical, sublingual, or rectal means. The preferred route of administration is intravenous. Compounds can also be administered via liposomes. Such administration routes and appropriate formulations are generally known to those of skill in the art.

Administration of the formulations may be accomplished by any acceptable method which allows the triplex-forming oligonucleotide and optionally a donor nucleotide, to reach its target.

Any acceptable method known to one or ordinary skill in the art may be used to administer a formulation to the subject. The administration may be localized (i.e., to a particular region, physiological system, tissue, organ, or cell type) or systemic, depending on the condition being treated.

Injections can be e.g., intravenous, intradermal, subcutaneous, intramuscular, or intraperitoneal. In some embodiments, the injections can be given at multiple locations. Implantation includes inserting implantable drug delivery systems, e.g., microspheres, hydrogels, polymeric reservoirs, cholesterol matrixes, polymeric systems, e.g., matrix erosion and/or diffusion systems and non-polymeric systems, e.g., compressed, fused, or partially-fused pellets. Inhalation includes administering the composition with an aerosol in an inhaler, either alone or attached to a carrier that can be absorbed. For systemic administration, it may be preferred that the composition is encapsulated in liposomes.

The oligonucleotides may be delivered in a manner which enables tissue-specific uptake of the agent and/or nucleotide delivery system. Techniques include using tissue or organ localizing devices, such as wound dressings or transdermal delivery systems, using invasive devices such as vascular or urinary catheters, and using interventional devices such as stents having drug delivery capability and configured as expansive devices or stent grafts.

The formulations may be delivered using a bioerodible implant by way of diffusion or by degradation of the polymeric matrix. In certain embodiments, the administration of the formulation may be designed so as to result in sequential exposures to the triplex-forming oligonucleotides, and optionally donor oligonucleotides, over a certain time period, for example, hours, days, weeks, months or years. This may be accomplished, for example, by repeated administrations of a formulation or by a sustained or controlled release delivery system in which the oligonucleotides are delivered over a prolonged period without repeated administrations. Administration of the formulations using such a delivery system may be, for example, by oral dosage forms, bolus injections, transdermal patches or subcutaneous implants. Maintaining a substantially constant concentration of the composition may be preferred in some cases.

Other delivery systems suitable include time-release, delayed release, sustained release, or controlled release delivery systems. Such systems may avoid repeated administrations in many cases, increasing convenience to the subject and the physician. Many types of release delivery systems are available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations of these. Microcapsules of the foregoing polymers containing nucleic acids are described in, for example, U.S. Pat. No. 5,075,109. Other examples include non-polymer systems that are lipid-based including sterols such as cholesterol, cholesterol esters, and fatty acids or neutral fats such as mono-, di- and triglycerides; hydrogen release systems; liposome-based systems; phospholipid based-systems; silastic systems; peptide based systems; wax coatings; compressed tablets using conventional binders and excipients; or partially fused implants. Specific examples include erosional systems in which the miRNA is contained in a formulation within a matrix (for example, as described in U.S. Pat. Nos. 4,452,775, 4,675,189, 5,736,152, 4,667,013, 4,748,034 and 5,239,660), or diffusional systems in which an active component controls the release rate (for example, as described in U.S. Pat. Nos. 3,832,253, 3,854,480, 5,133,974 and 5,407,686). The formulation may be as, for example, microspheres, hydrogels, polymeric reservoirs, cholesterol matrices, or polymeric systems. In some embodiments, the system may allow sustained or controlled release of the composition to occur, for example, through control of the diffusion or erosion/degradation rate of the formulation containing the oligonucleotides. In addition, a pump-based hardware delivery system may be used to deliver one or more embodiments.

Examples of systems in which release occurs in bursts include systems in which the composition is entrapped in liposomes which are encapsulated in a polymer matrix, the liposomes being sensitive to specific stimuli, e.g., temperature, pH, light or a degrading enzyme and systems in which the composition is encapsulated by an ionically-coated microcapsule with a microcapsule core degrading enzyme. Examples of systems in which release of the inhibitor is gradual and continuous include, e.g., erosional systems in which the composition is contained in a form within a matrix and effusional systems in which the composition permeates at a controlled rate, e.g., through a polymer. Such sustained release systems can be in the form of pellets, or capsules.

Use of a long-term release implant may be particularly suitable in some embodiments. "Long-term release," as used herein, means that the implant containing the composition is constructed and arranged to deliver therapeutically effective levels of the composition for at least 30 or 45 days, and preferably at least 60 or 90 days, or even longer in some cases. Long-term release implants are well known to those or ordinary skill in the art, and include some of the release systems described above.

The triplex-forming oligonucleotides will be further understood in view of the following non-limiting examples.

EXAMPLE 1

Targeted Crosslinking of the Human β-globin Gene by Modified Triple Helix Forming Oligonucleotides In Vitro Materials and Methods:
Reagents.
Reagent grade chemicals were used unless otherwise noted. HPLC grade acetonitrile was dried over calcium hydride. Anhydrous pyridine, dimethyl formamide, benzene, tetrahydrofuran and methylene chloride were from Aldrich Chemical Co. Inc. 5-β-$_D$-ribofuranosyluracil (pseudouridine) was generous gift from Dr. Kris Pankiewicz. The 5'-O-(4,4'-dimethoxytrityl)-5-methyluridine-2'-O-methyl-3'-O-(β-cyanoethyl-N,N-diisopropyl) phosphoramidite, the 5'-O-(4,4'-dimethoxytrityl)-5-methyluridine-2'-O-methyl-3'-O-succinamide-N$^6$-hexanamide N$^3$-propyl-controlled pore glass support were purchased from Chemgenes, Ashland, Mass. Protected deoxyribonucleoside phosphoramidites, the N$^4$-acetyl-5'-O-(4,4'-dimethoxytrityl)-5-methylcytidine-2'-O-methyl-3'-O-(β-cyanoethyl-N,N-diisopropyl)phosphoramidite and 6-[4'-(hydroxymethyl-4,5',8-trimethylpsoralen] hexyl-1-O-(β-cyanoethyl-N,N-diisopropyl) phosphoramidite, 8-hydroxy-5'-dimethoxytrityl-N6-benzoyldeoxyadenosine3'-[(2-cyanoethyl)(N,N-diisopropyl)]-phosphoramidite were purchased from Glen Research, Inc, Sterling, Va. The modified nucleosides 5'-O-(4,4'-dimethoxytrityl)-5-methyluridine-2'-O-(2-aminoethyl)-3'-O-(β-cyanoethyl-N,N-diisopropyl)phosphoramidite and N$^4$—(N-methylpyrrolidineamidine)-5'-O-(4,4'-dimethoxytrityl)-5-methylcytidine-2'-O-(2-aminoethyl)-3'-O-(β-cyanoethyl-N,N-diisopropyl)phosphoramidite were synthesized as described (Cuenoud, 1998 1822). All the reagents used for oligonucleotides synthesis were standard and were obtained form Chemgenes, Ashland, Mass. [[γ]-$^{32}$P]ATP was purchased from Amersham Inc. and T$_4$ polynucleotide kinase was purchased from United States Biochemical Corp. Thin layer chromatography (TLC) was performed on silicagel 60F$_{254}$ plates (0.2 mm) and flash chromatography was carried out using EM Science Kieselgel 60 (230-400 mesh). Proton NMR spectra were recorded on a JEOL 400 MHz spectrometer with tetramethylsilane as reference for chemical shift. Polyacrylamide gel electrophoresis was carried out in 12% polyacrylamide gels with or without 7 M urea. The TAE running buffer contained 40 mM Tris, 10 mM MgAc$_2$ and 5 mM NaAc buffered at pH 7.0. Reversed phase HPLC was carried out using a Symmetric 300™ C$_{18}$ column from Waters on a Shimadzu HPLC system (LC-10ADvp) with a duel wavelength detector (SPD-10AVvp) and an autoinjector (SIL-10AVvp).

Synthesis of Pseudoisocytidine Phosphoramidite.

The synthesis of 2[[(Dimethyl-amino)methylene]amino]-5-[2-O-methyl-5-O-(dimethoxytrityl)-β-D-ribofuranosyl]-4 (1H)-pyrimidinone-[N$^2$-[(Dimethylamino)methylene]-2'-O-methyl-5'-O-(dimethoxytrityl)-pseudoisocytidine-3'-O-(β-cyanoethyl-N,N-diisopropyl)phosphoramidite was done using the scheme reported previously (Ono, 1992 1728). The route involved conversion of pseudouridine to 1,3-dimethyl-3'-5'-O-(tetraisopropyldisiloxanyl)pseudouridine followed by methylation of the 2'-hydroxy group, deprotection of the silyl group, reprotection of 5'-hydroxy group with dimethoxytrityl, guandinylation and finally the protection of the amino group by (N,N-dimethylamino)methylene gave 2-[[(Dimethylamino)methylene]amino]-5-[2-O-methyl-5-O-(dimethoxytrityl)-β-$_D$-ribofuranosyl]-4(1H)-pyrimidinone-[N$^2$-[(Dimethylamino)methylene]-2'-O-methyl-5'-O-(dimethoxytrityl)pseudoisocytidine. Phosphitylation of the 3'-hydroxy group gave the expected pseudoisocytidine phosphoramidite which was confirmed from its NMR and MS data.

Oligonucleotide Syntheses.

The oligonucleotides were synthesized on CPG supports using an Expedite Model 8909 DNA/RNA synthesizer. All protected nucleoside phosphoramidites were dissolved in anhydrous acetonitrile at a concentration of 0.05 M. The nucleoside pseudoisocytidine phosphoramidite solution was stored for 2 h over 4° A molecular sieves prior to use. Standard coupling times were employed for general nucleosides, except for pseudoisocytidine phosphoramidite and for the psoralen phosphoramidites, which were 360 s and 600 s respectively. The synthesizer was programed to carry out a capping step, an oxidation step and then another capping step after each coupling step and finally to remove the last 5'-terminal dimethoxytrityl group from the protected oligomer. The psoralen-derivatized oligomers were prepared on the controlled pore glass support using 2-[4'-(hydroxymethyl)-4,5',8-trimethylpsoralen]hexyl-1-O-[(2-cyanoethyl)-(N,N-diisopropyl)]phosphoramidite in the final coupling reaction.

Deprotection and Purification of Oligonucleotides.

The non-psoralen oligonucleotides were deprotected by treatment with a solution of 28~30% ammonium hydroxide (J. T. Baker) at 55° C. for 5 h. Oligonucleotides containing 8-oxo-adenine and pseudoisocytidine were deprotected by treating the support-bound oligomer with a solution of ethylenediamine in 95% ethanol (1:1 v/v) at room temperature for 16 h and in the case of psoralen oligos, deprotection time was 90 min. The deprotected oligomers were taken up in distilled water and purified by analytical and semipreparative anion exchange (IE) HPLC using DIONEX DNAPac column on a Shimadzu HPLC system (LC-10ADvp) with a duel wavelength detector (SPD-10ADvp) and an autoinjector (SIL-10AVvp). The column was eluted using a linear gradient of 0-50% acetonitrile in 100 mM Tris-HCl buffer (pH 7.8) at a flow rate of 1.5 ml/min and monitored at 254 and 315 nm. The oligomers were desalted on a SEP PAK $C_{18}$ cartridge following standard procedures. The purified oligomers migrated as single bands on 12% polyacrylamide gels and characterized by matrix-assisted laser desorption-ionization time of flight (MALDI TOF) mass spectrometry at the Johns Hopkins University School of Medicine Mass Spectrometry Facility.

Thermal Stability Measurements.

The constituent strands of the target duplexes (1 µM) were dissolved in buffer containing 100 mM NaCl, 2 mM $MgCl_2$, and 10 mM Na-Cacodylate, pH 7.0. The solutions were heated at 80° C. for 3 min, and allowed to come to RT. The TFOs (1 µM) were added to the duplex solution and incubated at room temperature overnight. The thermal denaturation experiments were carried out using a Cary 3E UV-vis spectrophotometer fitted with a thermostatted sample holder and temperature controller. Triplexes were heated from 10 to 85° C. at a rate of 0.4° C./min, and the absorbance at 260 nm was recorded as a function of the temperature. All analyses were performed at least 2 times with an error of no more than 0.5° C.

TFO Association Analysis by Absorbance Decay.

The TFO+duplex→triplex transition is accompanied by decrease in UV absorbance. This decay curve has used to estimate association rates of a TFO with the target duplex (Arya, 2001 3527). The duplex strand was formed in Kinetics Buffer I (1 mM $MgCl_2$, 10 mM sodium cacodylate (pH 7.2), 150 mM KCl) to give a final concentration of 1 µM. 1 ml of the duplex stock solution was monitored by UV in a cuvette at 25° C. and gave a horizontal line as a function of time. The analyses were done at 25° C. (using a Peltier temperature controller). An aliquot of the TFO stock solution in Kinetics Buffer I was added with vigorous mixing to 1 ml of duplex stock solution. The mixing process took less than 10 sec. The experiments were run on a Cary Dual beam spectrophotometer. The decay curves were fit using second order kinetics with the software supplied with the instrument. Rate constants were reported as an average of three or more experiments.

Band Shift Analysis of Triplex Formation.

The pyrimidine strand of the duplex was labeled with $^{32}P$, the duplex formed and then the triplex formed by incubation of the duplex (approximately 1 nM) and the third strand (2 µM) overnight in triplex formation buffer. The samples were then electrophoresed on 12% neutral polyacrylamide gels, in 10 mM Tris acetate (pH 7.0), 5 mM $MgCl_2$.

Psoralen Integrity Assay.

After triplex formation on a $^{32}P$ labeled duplex, the samples were exposed to UVA (365 nM) for 10 min, denatured by heating in loading buffer (containing 90% formamide), and then electrophoresed in a 12% denaturing polyacrylamide gel in 10 mM tris borate, pH 8.0, 7 M urea.

Results:

The β-Globin IVS2 Target Sequence.

The human β-globin gene consists of three exons and two introns. Inside the second intron is a 21 base polypurine:polypyrimidine element that contains four adjacent cytosines and is terminated by a 5' TA step, which is a favored site for psoralen crosslinking (FIG. 1). This element was chosen as a model triplex target sequence (FIG. 1). Triplex forming oligonucleotides (TFOs) were characterized based on their ability to form a triplex with this target sequence. A series of pyrimidine and purine TFOs were characterized, containing adjacent cytosines or 5 methylcytosines (5-MeC), with different base, sugar, and backbone modifications. The base modification was 5-(1-propynyl)-2'-deoxyuridine (pdU) (Lacroix, 1999 35). The sugar modifications were 2'-guanidoethyl (2'-OGE) (Prakash, 2004 5567), 2'-O,4'-C-methylene ribose (LNA) {Obika, 2001 3440) (Jepsen, 2004 5545), 2'-O-(2-methoxyethyl) (2'-OME) (Lind, 1998 1817), 2'-O—(N-(methyl)acetamide) (Pattanayek, 2004 5566), morpholino (Summerton, 1997 371), 2'-O-methyl (2'-OME), and 2'-aminoethoxy (2'-AE) (Cuenoud, 1998 1822). The backbone modification was the non bridging phosphate derivative, diethylethlenediamine (DEED) (Dagle, 1996 1502). Target binding by the TFOs (shown in Table 1) were analyzed in a band shift assay at pH 5.6 and 7.2.

TABLE 1

Triplex-farming oligonucicotide derivatives used in Example 1.

| TFO | Base | Sugar |
|---|---|---|
| TCTTTTCTTCCCCTTTCTTTT (SEQ ID NO:1) | 5MeC | deoxy |
| AAAAGAAAGGGGAAGAAAAGA (SEQ ID NO:2) | | deoxy |
| UCUUUUCUUCCCCUUUCUUUU (SEQ ID NO:3) | 5MeC/pdU | deoxy |

TABLE 1-continued

Triplex-forming oligonucleotide derivatives used in Example 1.

| TFO | Base | Sugar |
|---|---|---|
| U*CU*U*U*U*CTTCCCCTTTCTTTU* (SEQ ID NO:4) | 5MeC/5MeU* | 2-OGE*, 2'-OMe |
| TCTTTTCTTCCCCTTTCTTTU$^A$ (SEQ ID NO:5) | 5MeC | 2'-OMOE, 3'-OMOE$^A$ |
| TCTTTTCTTC$_{AE}$C$_{AE}$C$_{AE}$C$_{AE}$TTTCTTTT (SEQ ID NO:6) | 5MEC | 2'-AE, 2'-OMe |
| TCTTTTCTTCC$_{AE}$C$_{AE}$CTTTCTTTT (SEQ ID NO:7) | 5MeC | 2'-AE, 2'OMe |
| TGTTTTGTTGGGGTTTGTTTT (SEQ ID NO:8) | | deoxy |
| T$_L$CT$_L$TT$_L$TC$_L$TT$_L$CC$_L$CC$_L$TT$_L$TC$_L$TT$_L$TT$_L$ (SEQ ID NO:9) | | LNA (alt) |
| (UCUUUUCUUCCCCUUUCUUU)$_{MA}$ U (SEQ ID NO:10) | 5MeC/5MeU | 2'-OMA |
| TCTTTTCTTCCCCTTTCTTTT $_{(MORPH)}$ (SEQ ID NO:11) | | morpholino |
| A+G+A+A+A+G+G+G+A+A+G+A+A+A+ A+G+A+ (SEQ ID NO:12) | | Deed (diethylethylenediamine) |

AE, 2'-aminoethoxy; pdU, 5-(1-propynyl)-2'-deoxyuridine; OGE, 2'-O-(2-guanidoethyl)-5 methyl-U); UMOE, methoxyethyl; LNA, 2'-O,4'-C-methylene linked locked nucleic acid; OMA, 2'-O—(N-(methyl)acetomido)-5-methyl; MORPH, morpholino; DEED, diethylethylenediamide. The TFO containing the oGE derivative has the OGE sugar modification linked to 5 methyl-U.

While a number of the TFOs were able to form stable triplexes at pH 5.6, they either showed weak binding (the DEED TFO, $K_d$=10$^{-6}$), or no binding (all other TFOs) at pH 7.2. Of particular interest were the TFOs containing 2'-O-aminoethoxy (AE) residues in the cytosine patch. The AE moiety is positively charged at neutral pH and has been shown to stabilize triplexes (Cuenoud, 1998 1822). The band shift assays with all the oligonucleotides, including the AE TFOs, indicated that the inhibitory effect of the cytosine run overcame substitutions that otherwise stabilize triplexes at neutral pH.

Figure 2A:
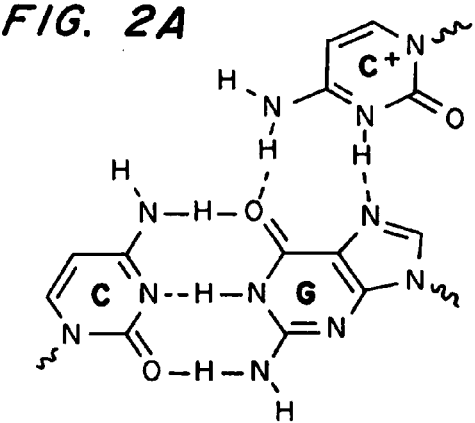
FIG. 2 shows the structure of C⁺•G:C (a), T•A:T (b), 8-oxo-A (A⁸)•G:C(c), and 2'-O-methylpseudoisocytidine (P)•G:C (d) triplets.
Figure 2B:
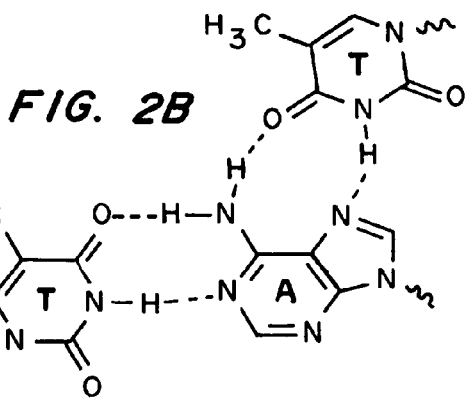
Figure 2C:
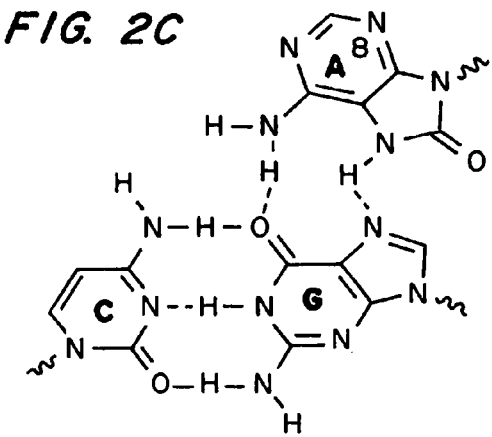
Figure 2D:
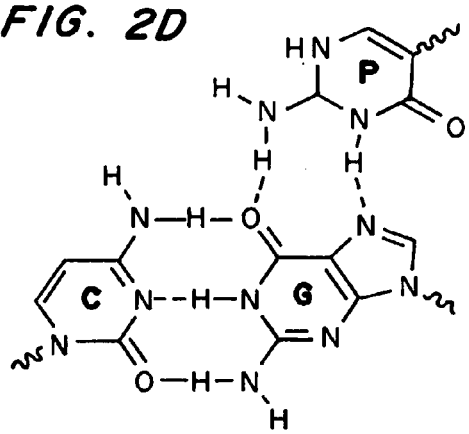

All of the pyrimidine TFOs contained cytosine or 5MeC, both isolated and adjacent. The failure of these constructions prompted consideration of the effect of substitutions of cytosine replacements within the cytosine patch. C$^+$•G:C or 5-MeC$^+$•G:C triplets are stabilized by hydrogen bonding, and also the positive charge, which appears to make a major contribution (Asensio, 1998 3461). However, cytosine replacements, such as 8-oxo-adenine (A$^8$), or 2'-O-methylpseudoisocytidine (P) (FIG. 2A), used in the following experiments, lack the positive charge. In order to assess the consequences for triplex stability of the loss of the protonated cytosine, charge duplex targets were synthesized for binding studies in which all (duplex 2), or two of the four cytosines (duplex 3, 4), were replaced with T, as shown below. The four clustered G:C pairs are separated from the remainder of the sequence, and the psoralen crosslink site is indicated in larger font. In Duplex 2, the adjacent G:C pairs were replaced with A:T. In Duplex 3, G:C and A:T pairs were alternated, while in Duplex 4, the G:C flanked adjacent A:T pairs. These targets provided the opportunity to examine the stability of complexes in which the T•A:T triplets would provide a reference for triplets formed by the uncharged cytosine replacements.

```
Duplex 1
5'-ATGTTTTCTTT CCCC TTCTTTTCTATGG  (SEQ ID NO:13)
3'-TACAAAAGAAA GGGG AAGAAAAGATACC  (SEQ ID NO:14)

Duplex 2
5'-ATGTTTTCTTT TTTT TTCTTTTCTATGG  (SEQ ID NO:15)
3'-TACAAAAGAAA AAAA AAGAAAAGATACC  (SEQ ID NO:16)

Duplex 3
5'-ATGTTTTCTTT CTCT TTCTTTTCTATGG  (SEQ ID NO:17)
3'-TACAAAAGAAA GAGA AAGAAAAGATACC  (SEQ ID NO:18)

Duplex 4
5'-ATGTTTTCTTT CTTC TTCTTTTCTATGG  (SEQ ID NO:19)
3'-TACAAAAGAAA GAAG AAGAAAAGATACC  (SEQ ID NO:20)
```

Triplexes were prepared with the duplexes and the corresponding TFOs shown below.

```
TFO-1   3'-TTTT5TTT 5555 TT5TTTT5T   (SEQ ID NO:21)
TFO-2   3'-TTTT5TTT TTTT TT5TTTT5T   (SEQ ID NO:22)
TFO-3   3'-TTTT5TTT 5T5T TT5TTTT5T   (SEQ ID NO:23)
TFO-4   3'-TTTT5TTT 5TT5 TT5TTTT5T   (SEQ ID NO:24)
TFO-5   3'-TT5TT5TT 5TT5 TT5TT5TT5   (SEQ ID NO:25)
```

The third strands contained 5-MeC (5) as indicated and all sugars were 2'-O methyl ribose. TFO-5 was prepared as a scrambled sequence control. Thermal stability analysis demonstrated that the $T_m$ value of the duplex containing the β-globin target sequence was 65.5° C., while the sequences of the other duplex targets were similar (Duplex 3, 64.2° C.) or reduced, reflecting the alterations in sequence context and the replacement of C with T (Duplex 2, 56.7° C.; Duplex 4, 58.4° C.). Previous work has shown that triplexes with isolated cytosines, formed by TFOs containing 2'-O methyl ribose at all positions, had $T_m$ values that were similar to that of the underlying duplex at neutral pH (Puri, 2002 3567) (Shimizu, 1992 1285). This was observed with the triplexes formed on the variant duplexes 2, 3, 4. However, the destabilizing effect of the adjacent (5-Me) cytosines was readily apparent in the analysis of the triplex formed by TFO-1 on Duplex 1, as the $T_m$ value was 21.5° C. lower than the duplex. The scrambled control TFO-5 failed to make a stable triplex.

TFOs Containing A[8].

Third strands were synthesized with A[8] variously used as a cytosine replacement, as shown below.

```
TFO-1   3'-TTTT5TTT AAAA TT5TTTT5T    (SEQ ID NO:26)

TFO-8   3'-TTTT5TTT AAA5 TT5TTTT5T    (SEQ ID NO:27)

TFO-9   3'-TTTT5TTT 5AA5 TT5TTTT5T    (SEQ ID NO:28)

TFO-10  3'TTTT5TTT 5A5A TT5TTTT5T     (SEQ ID NO:29)

TFO-11  3'-TTTTATTT AAAA TTATTTTAT    (SEQ ID NO:30)
```

Figure 4:
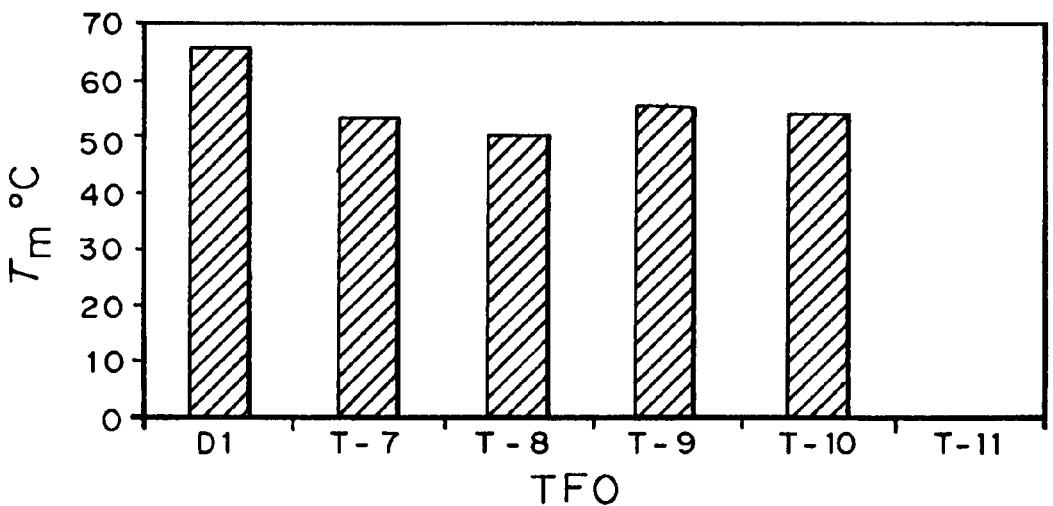
FIG. 4 is a graph of $T_m$ values for the triplexes formed by TFOs-7-10. For reference the value for Duplex 1 is also shown.

These oligonucleotides were designed to examine the effect of adjacent A[8] residues (TFO-7, 8, 9) as well as in alternation with 5-MeC. A TFO in which all cytosine positions were replaced by A[8] was also prepared (TFO-11). This TFO was unable to form a triplex. However, the other oligonucleotides in this group formed triplexes that were more stable than that formed by TFO-1. The most stable triplexes were formed by TFOs-7, 9, 10, with $T_m$ values 8-10 degrees higher than with TFO1 (FIG. 4). Band shift analysis confirmed the formation of stable triplexes by TFOs 7, 9, 10, but not by TFO-1 or the scrambled control TFO-5.

Figure 3:
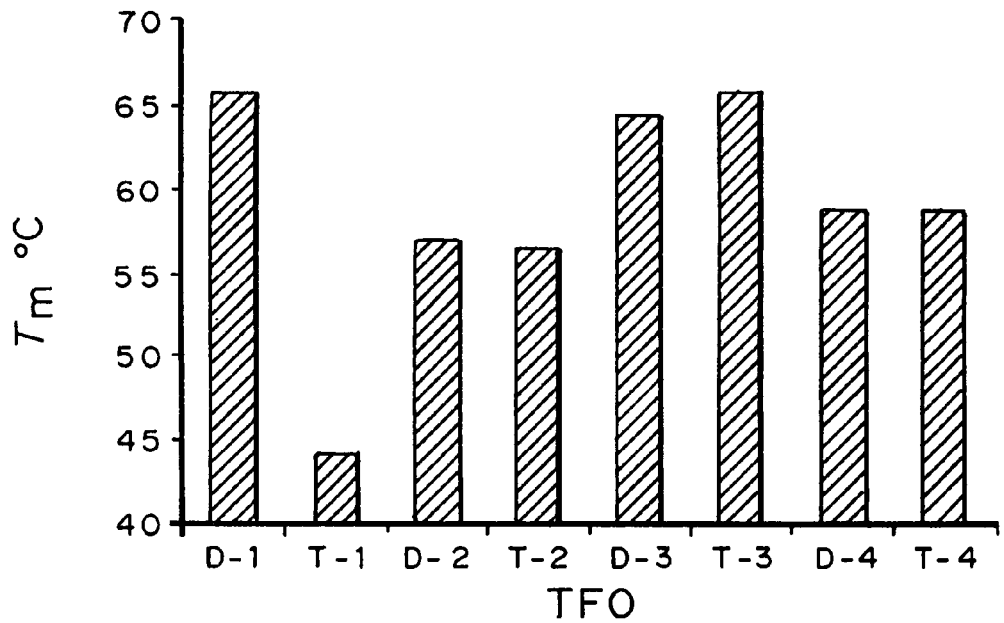
FIG. 3 is a graph of the thermal stability of duplexes 1-4 and the triplexes formed by TFO-1-4. In this figure D=duplex and T=triplex.

Although TFOs 7-10 were an improvement relative to TFO-1, their triplexes were not as stable as the duplex target. This would be expected given the absence of positive charge on A[8]. However, comparison with the results with the cognate triplexes shown in FIG. 3 indicated that triplexes with A[8]•A:T triplets were less stable than triplexes with T•A:T triplets at the corresponding positions. Thus the absence of the positive charge did not completely explain the relatively low Tm values.

TFOs Containing Pseudoisocytidine.

TFOs 12-14 were synthesized. These replaced cytosine with pseudoisocytidine (P) in the same pattern as the TFOs with A[8].

```
TFO-12  3'-TTTT5TTT PPPP TT5TTTT5T    (SEQ ID NO:31)

TFO-13  3'-TTTT5TTT 5PP5 TT5TTTT5T    (SEQ ID NO:32)

TFO-14  3'-TTTT5TTT 5P5P TT5TTTT5T    (SEQ ID NO:33)
```

Figure 5:
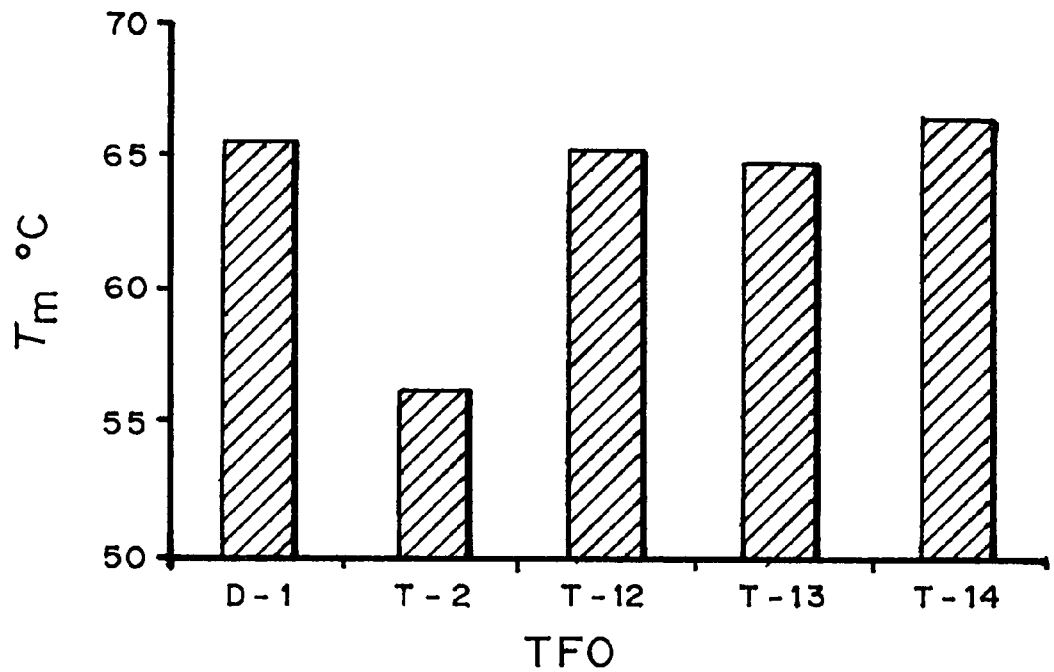
FIG. 5 is a graph of the thermal stability of triplexes formed by Duplex 1 and TFO12-14. For comparison the $T_m$ value for Duplex 1 and the triplex on the variant duplex with 4 adjacent A:T pairs are shown.

Thermal analysis of the triplex formed by TFO-14 (with the alternation of P and 5-MeC) yielded a $T_m$ slightly higher than the duplex (66.3 vs 65.5° C.). Indeed the $T_m$ values for the triplexes formed by TFOs 12-14 were similar to the value for the duplex target (FIG. 5). Band shift analysis confirmed triplex formation by the three TFOs. These results indicated that P could effectively replace cytosine in runs of adjacent cytosines, producing TFOs that could form quite stable triplexes at neutral pH.

TFOs with P and AE Substitutions.

TFOs were prepared which contained a patch of 4 AE residues at the 3' end and different patterns of P substitution.

```
TFO-17
3'-TTTT5TTT PPPP TT5TTTT5T-pso    (SEQ ID NO:34)

TFO-18
3'-TTTT5TTT 5PP5 TT5TTTT5T-pso    (SEQ ID NO:35)

TFO-19
3'-TTTT5TTT 5P5P TT5TTTT5T-pso    (SEQ ID NO:36)

TFO-20
3'-TTTT5TTT PPPP TTPTTTTPT-pso    (SEQ ID NO:37)

TFO-22
3'-TTTT5TTT 5P5P TT5TTTTPT-pso    (SEQ ID NO:38)
```

Figure 6:
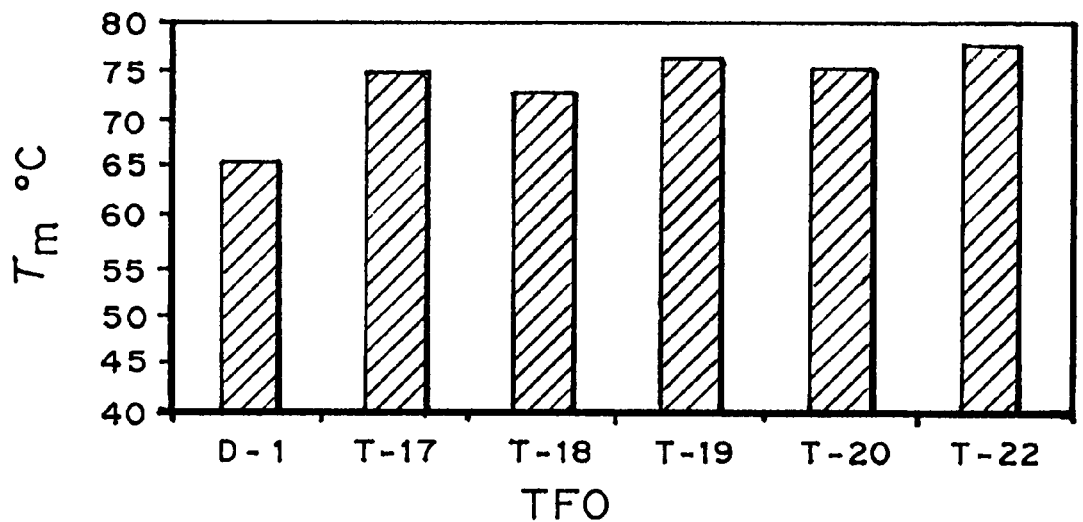
FIG. 6 is a graph of the thermal stability of triplexes formed by Duplex 1 and TFO7-22. For comparison the $T_m$ value for Duplex 1 and the triplex on the variant duplex with 4 adjacent A:T pairs are shown.

The introduction of AE residues increased the $T_m$ values for all the TFOs (FIG. 6). The TFOs with different patterns of the P substitution showed marked increases. TFO-19, for example with the alternation of 5-MeC and P, had a $T_m$ value of 76.6° C., approximately 12° C. higher than the underlying duplex. Triplex formation was confirmed by band shift analysis. Complete conversion of the labeled duplex to triplex was observed with TFOs-17, 18, and 19. It was noteworthy that the pattern of P substitution in the cytosine run did not appear to be critical as the oligonucleotide with four contiguous P residues (TFO-17) was as effective in both assays as the TFO-18, 19, with non adjacent P substitutions.

The P replacement for cytosine is non-charged which prompted an inquiry as to the consequences of replacement of isolated cytosines in the TFOs. Two additional oligonucleotides were synthesized. One was based on TFO-19 and had one additional P residues near the 5' end (TFO-22). In the second, all but one cytosine were replaced with the P substitution (TFO-20). Both these TFOs formed quite stable triplexes as indicated by the $T_m$ values and the band shift analysis (FIG. 4), essentially equivalent to the other TFOs in this group.

The TFOs in the AE-P group were linked to psoralen. Psoralen is labile to alkali and it was important to insure that it was still active after deprotection and purification. Triplexes were prepared on radioactively labeled duplex, and then exposed the preparations to long wave ultraviolet light to photoactivate the psoralen. The samples were then electrophoresed on polyacrylamide gels in the presence of 7M urea. The urea denatures the triplex, and thus resolves three strand complexes linked via psoralen, while non crosslinked molecules migrate with the unconjugated, denatured duplex strands. This assay verified the integrity of the psoralen, which was essential for the analysis of the biological activity of the TFOs.

EXAMPLE 2

Targeted Crosslinking of the Human β-globin Gene by Modified Bis-peptide Nucleic Acids (bis-PNAs) In Vitro Materials and Methods:
Bis-PNAs.

Bis-PNAs were generated either by Peter Nielson & Biosynthesis, Inc. (Lewisville, Tex.) or Applied Biosystems (Framingham, Mass.). Sequences of bis-PNAs used in this Example are indicated in the Results section.

Duplex Sequences for Electrophoretic Mobility Shift Assays (EMSAs) of TFOs.

Underlined sections of the sequences represents the polypyrimidine/polypurine run The IVS2-24 synthetic duplex was generated from the following oligos.

OJK3
(SEQ ID NO:39)
5'-GGGACCCTTGATG<u>TTTTCTTTCCCCTTCTTTTCT</u>ATGGTTAAGTTC-3'

OJK4
(SEQ ID NO:40)
3'-CCCTGGGAACTAC<u>AAAAGAAAGGGGAAGAAAAGA</u>TACCAATTCAAG-5'

Plasmid Vectors.

Plasmid pBluescript-2-24 containing the target site for the 2-24 bis-PNAs was generated by annealing the oligonucleotides 5'-GATCTTTTCTTTCCCCTTCTTTTCT ATG-GTTA-3' (SEQ ID NO:41) and 5'-GATCTAACCATA-GAAAAGAAGGGGAAAGAAAA-3' (SEQ ID NO:42) then cloning them into the BamHI site of pBluescriptII-SK (Stratagene, La Jolla, Calif.). Directly adjacent to the bis-PNA binding site of pBluescript-2-24 is an AT site capable of psoralen intercalation and crosslinking. Plasmids pBluescript-2-512 and pBluescript-2-830 were also generated containing the target sites for the 2-512 bis-PNAs (by annealing the oligonucleotides 5'-GATCTTTAAAAAATGCTTTCT-TCTTTTAATATACTT-3 (SEQ ID NO:43) and 5'-AAT-TAAGTATATTAAAAGAAGAAAGCATTTTTTAAA-3') (SEQ ID NO:44) and 2-830 bis-PNAs (by annealing the oligonucleotides 5'-GATCATACCTCTTATCTTCCTCCCA-CAGGAC TGC-3' (SEQ ID NO:45) and 5'-AATTGCAGTC-CTGTGGGAGGAAGATAAGAGGTAT-3') (SEQ ID NO:46), respectively, then cloning them between the BamHI/EcoRI sites of pBluescriptII-SK.

Electrophoretic Mobility Shift Assays (EMSAs) of TFOs.
Electrophoretic Mobility Shift Assays (EMSAs) were performed to determine apparent dissociation constants ($K_d$ values) of the TFOs. Annealed oligonucleotides (synthetic duplex) containing the TFO target site were end-labeled using T4 polynucleotide kinase and [$\alpha$-$^{32}$P]ATP, gel purified, and incubated overnight (approximately 18-24 hours) at 37° C. with increasing concentrations of TFO. Ion concentration ($Mg^{++}$ and/or $K^+$) and pH can be modified by changing these parameters in the buffer of the binding reaction. The reactions are then subjected to gel electrophoresis in a 12% non-denaturing polyacrylamide (19:1 acrylamide:bisacrylamide) gel containing 89 mM Tris, 89 mM boric acid, pH 7.2, and 10 mM $MgCl_2$ (for pH 7.2 conditions) using a BioRad Mini PROTEAN 3 apparatus for approximately 4 hours at 65V. For pH 5.6 conditions, 12% non-denaturing gels contain 50 mM MES, pH 5.6, and 10 mM $MgCl_2$ and were run on a larger BioRad PROTEAN II xi cell apparatus for approximately 7 hours at 270V. The gels were then dried and visualized by autoradiography. The dissociation constant ($K_d$) is determined to be the concentration of TFO in which half is bound to the duplex and half is unbound and is a function of the reaction conditions.

TFO Purification.
TFOs were resuspended in water and purified using a NAP-5 column (Amersham Biosciences, Uppsala, Sweden) and concentrated using Centricon-10 columns (Millipore, Bedford, Mass.) at 5,000 g for 1 hour.

BisPNA Triplex-Invasion Complex Formation.
Plasmid (2 μg) containing the bis-PNA binding site (pBluescript derivatives) is incubated overnight with increasing concentrations of PNA (0 μM, 0.2 μM, 0.4 μM, 0.8 μM, and up to 1.2 μM) at 37° C. in TE buffer (pH 7.4) with 10 mM KCl.

Electrophoretic Mobility Shift Assays (EMSAs) of bisPNA-Bound Plasmid.
After plasmid:PNA complex formation, the reaction was digested with restriction enzymes SacI and XhoI for 2 hours. This releases a 119 bp, 105 bp, and 103 bp fragment in pBluescript-2-24, pBluescript-2-512 and pBluescript-2-830, respectively, containing the bis-PNA binding site. The digestion reactions were run on an 8% non-denaturing TBE acrylamide (19:1 acrylamide:bisacrylamide) gel and visualized by silver staining.

T7 RNA Polymerase-Based Transcription Elongation Arrest Assay for Analysis of Photoadduct Formation.
After plasmid:PNA complex formation, the reactions were UVA irradiated (365 nm) at a dose of 1.8 J/cm$^2$ and the plasmid:PNA complexes were linearized with XbaI for approximately 1.5 hours at 37° C. After purification of the linearized template, the transcription elongation arrest assay was performed in 30 μL of transcription reaction mixture (1 mM NTPs [except UTP], 0.2 mM UTP 2 μCi[$\alpha$$^{32}$P]UTP, and 2.5 units of T7 RNA polymerase) for 30 minutes at 37° C. The reaction was terminated by adding a stop buffer containing formamide. The transcription reaction was boiled for 3 minutes and analyzed on a 8% denaturing polyacrylamide (20:1 acrylamide:bisacrylamide) gel containing 7M urea in TBE buffer. Non-irradiated plasmid:PNA complexes were run in parallel as controls. As size markers, transcription reactions of a PstI linearized and a SpeI linearized pBluescript-2-24 plasmid were also loaded. Products were visualized by autoradiography.

Results:
Binding of Chemically Modified Bis-PNAs to β-Globin In Vitro.

The same 21 base polypurine:polypyrimidine element in the second intron of the human β-globin gene that was chosen as a target sequence in Example 1 was used as a target sequence in this Example. As in Example 1, this target sequence contains four adjacent cytosines and is terminated by a 5' TA step, which is a favored site for psoralen crosslinking (FIG. 1). The second intron of the human β-globin gene is also referred to as IVS2, and the target sequence used in this Example and in Example 1 is also referred to in this Example as IVS2-24 (FIG. 7). Two additional target sequences from the second intron of the human β-globin gene used in this Example are IVS2-512 and IVS2-830. The numbers following the IVS2 designation refer to the number of the first nucleotide of the target sequence relative to the first nucleotide of intron 2. Bis-PNAs were characterized based on their ability to bind to this target sequence in vitro. Two bis-PNAs were designed and synthesized to test for binding to IVS2-24. These two bis-PNAs, designated PNA 2843 and PNA 2844, shared the same sequence, but PNA 2844 was conjugated to psoralen, while PNA 2843 was left unconjugated. The sequence of these PNAs was: TPTTTTPTTP-(egl)3-CT-TCTTTTCT-(Lys-Lys-Lys) (SEQ ID NO:47), where T=thymidine, P=pseudoisocytidine, egl=8-amino-3,6-dioxaoctanoic acid, C=cytosine and Lys=lysine. Bis-PNA oligos bind first by strand invasion followed by triple helix formation and therefore their binding affinity cannot be represented with a dissociation constant as with TFOs as the "on rate" for strand invasion is slow but, once formed, the complex is extremely stable. The estimated melting temperature ($T_m$) of the bis-PNAs designed to IVS2-24 is approximately 75° C. off a single strand of DNA. PNA 2843 and PNA 2844 were assayed for binding to IVS2-24 by electrophoretic mobility shift assays (EMSAs). Both unconjugated bis-PNA (PNA 2843) and and bis-PNA conjugated to psoralen (PNA 2844) bound at neutral pH in TE buffer. A bis-PNA designed in the reverse orientation did not exhibit any binding, thus illustrating both the sequence and orientation specificity of these molecules. Moreover, increasing amounts of PNA 2843 and PNA 2844 bis-PNAs caused an increasing amount of dsDNA to shift. The additional bands present at increasing PNA concentrations may be attributed to different structural isomers formed by the 1:1 bisPNA:dsDNA complex where the linker may pass on the outside of the target DNA strand, inside the DNA helix between the target and non-target strand, or encircle both DNA strands causing bands of varying mobilities. Furthermore, a 2:1 complex could be formed at the highest PNA concentrations where the N-terminal strand of one PNA molecule and the C-terminal strand of another may both bind the target.

Covalent DNA Crosslinking In Vitro with Psoralen-Conjugated PNAs to IVS2-24.

The ability of psoralen-conjugated PNA to form interstrand crosslinks at its target site was studied using a T7 RNA polymerase transcription elongation arrest assay. In this assay, the transcription reaction is run on a sequencing gel and if there is an interstrand cross-link present after UVA irradiation, the polymerase will stall, causing an accumulation of shorter, "truncated" bands. It was demonstrated that interstrand crosslinks appear only when the sample is exposed to UVA and increased concentrations of PNA correlate to an increased amount of crosslinks, evidenced by the accumulation of the truncated elongation band at the expected size.

Binding of Chemically Modified Bis-PNAs to β-Globin IVS2-512 and IVS2-830 in vitro.

As described above, two other bis-PNAs were designed to target A-rich IVS2-512 and G-rich IVS2-830. The sequence of the bis-PNA targeting IVS2-512 was: TTPTTPTTTP-(egl)-Lys(SMCC)-(egl)-CTTTCTTCTT (SEQ ID NO:48), where T=thymidine, P=pseudoisocytidine, egl=8-amino-3,6-dioxaoctanoic acid, Lys=lysine, SMCC=succinimidyl-4-(N-maleimidomethyl)cyclohexane-1-carboxylate and C=cytosine. The sequence of the bis-PNA targeting IVS2-830 was: PPPTPPTTPT-(egl)-Lys(SMCC)-(egl)-TCTTC-CTCCC (SEQ ID NO:49), where T=thymidine, P=pseudoisocytidine, egl=8-amino-3,6-dioxaoctanoic acid, Lys=lysine, SMCC=succinimidyl-4-(N-maleimidomethyl) cyclohexane-1-carboxylate and C=cytosine.

Both bis-PNAs demonstrated binding at neutral pH in TE buffer while showing fewer structural isomers than the bisPNA to IVS2-24. The bisPNA targeting IVS2-512 also caused greater shifting at lower concentrations than the bisPNA targeting IVS2-830 which may be due to the IVS2-512 target site composition which contains 70% A:T basepairs while the IVS2-830 site is more G:C rich (only 40% A:T), thus slowing down PNA strand invasion.

EXAMPLE 3

Targeted Crosslinking of the Human β-globin Gene by Modified Triple Helix Forming Oligonucleotides (TFOs) in Living Cells Materials and Methods:
Crosslinking of the Triplex Target in the Human β-Globin Gene in Cultured Cells.

Human erythroleukemia K562 cells were suspended in 100 μl solution with TFO-22 at 4 μM, and then electroporated (Amaxa). The cells were suspended in medium and incubated for 3 hrs at room temperature. They were then exposed to UVA (365 nM) for 3 min in a Rayonet chamber at 1.8 J/cm$^3$.

Genomic DNA was then extracted from the cells, purified and then digested with EcoRI restriction enzyme. The digested samples were denatured by heating in 90% formamide and then electrophoresed in a neutral 1.5% agarose gel. The gel was blotted onto a nylon filter which was hybridized with a $^{32}$P labeled probe against the human β-globin gene in a 5 kb restriction fragment.

Results:
Bioactivity of TFOs.

Results form Examples 1 and 2 indicated that triplex forming oligonucleotides (TFOs) and peptide nucleic acids (PNAs) could bind to target sequences in vitro. However, it was essential to assay the ability of TFOs to bind to target sequences in living cells. The β-globin gene is not amenable to the facile mutation reporting that has made the HPRT gene so popular for mutagenesis studies. Consequently it was necessary to develop a biochemical strategy to measure TFO bioactivity. It is known that a psoralen-linked TFO can introduce crosslinks into target sequences at sufficiently high levels to allow detection of the crosslink as a biochemical entity. Denaturation resistance of crosslinked restriction fragments is well known (Hartley, 1993 2005). Denatured crosslinked strands snapback to duplex form upon entry into a neutral environment, while non crosslinked DNA fails to re-anneal. The denatured and snapback duplex fragments have different electrophoretic mobilities in agarose gels, and the amount of snapback target DNA can be used as a measure of targeted crosslinking (Majumdar, 2003 4243). TFO-22 was introduced into erythroleukemia K562 cells by electroporation. After 3 hours the cells were exposed to UVA to photoactivate the psoralen conjugated to TFO-22. DNA was extracted from the cells and then digested with EcoRI generating a 5 kb fragment containing the triplex target site. The DNA digests were denatured and electrophoresed in a neutral agarose gel. The gel was blotted and then hybridized with a β-globin gene probe. As expected the band in the non denatured sample migrated more slowly than in the denatured control sample. While there was no detectable band at the non-denatured position in the DNA isolated from untreated cells, there was a readily detected band in the snapback position in DNA from cells treated with TFO-22. Analysis of the band intensity by densitometry indicated that about 10% of the target DNA was in the crosslinked band. This assay is known to under reports the actual extent of crosslinking by about twofold (Majumdar, 2003 5011). In a parallel analysis, the digested DNA was examined by hybridization with a probe against the dihydrofolate reductase (DHFR) gene. There was no denaturation resistant band in this pattern. These results demonstrated that TFOs are capable of finding and binding the β-globin IVS2 target sequence in living human cultured cells. Furthermore, the lack of crosslinking in the DHFR gene argued for targeting specificity, at least at the level of the gene.

EXAMPLE 4

Conversion of a Splicing Defective Mutation in the Human β-Globin Gene Using Sequence-Specific Binding Molecules and Donor Oligomers Materials and Methods:
Oligonucleotides.

Donor oligonucleotides were synthesized by Midland Certified Reagent Company (Midland, Tex.) and purified by Reversed Phase HPLC. Primer Sequences were as follows:
DonorGFP-IVS2-1 (Sense)
5'-GTTCAGCGTGTCCGGCGAGGGCGAGGT-GAGTCTATGGGACCC TTGATGTTT-3' (SEQ ID NO:50)

DonorGFP-IVS2-1 (Antisense)
5'-AAACATCAAGGGTCCCATAGACTCAC-CTCGCCCTCGCCGGAC ACGCTGAAC-3' (SEQ ID NO:51)
Donor FLAS
5'-CGGGCCTTTCTTTATGTTTTTGGCGTCT-TCCATGGTGGCTTTA CCAAGCT-3' (SEQ ID NO:52)
Donor FLS
5'-TGGTAAAGCCACCATGGAAGACGC-CAAAAACATAAAGAAAG GCCCGGCGCC-3' (SEQ ID NO:53)

All donor molecules were 5' and 3' end protected with three phosphorothioate internucleoside linkages.

RT-PCR and Sequencing Primers
pJK115 forward primer: 5'-AGCAAGGGCGAGGAGCT-GTTCACC-3' (SEQ ID NO:54)
pJK118 reverse primer: 5'-CACTGCACGCCGTAGGT-CAGGGT-3' (SEQ ID NO:55)
Primers to Generate 1168 bp dsDonor
pJK127 forward primer: 5'-CCAGTACATGACCT-TATGGGACTT-3' (SEQ ID NO:56)
pJK128 reverse primer: 5'-TATTGCTATTGCCTTAAC-CCAGAA-3' (SEQ ID NO:57)

All primers were synthesized by W.M. Keck Oligonucleotide Synthesis Facility, Yale University, New Haven, Conn.

Plasmid Vectors.

Figure 8:
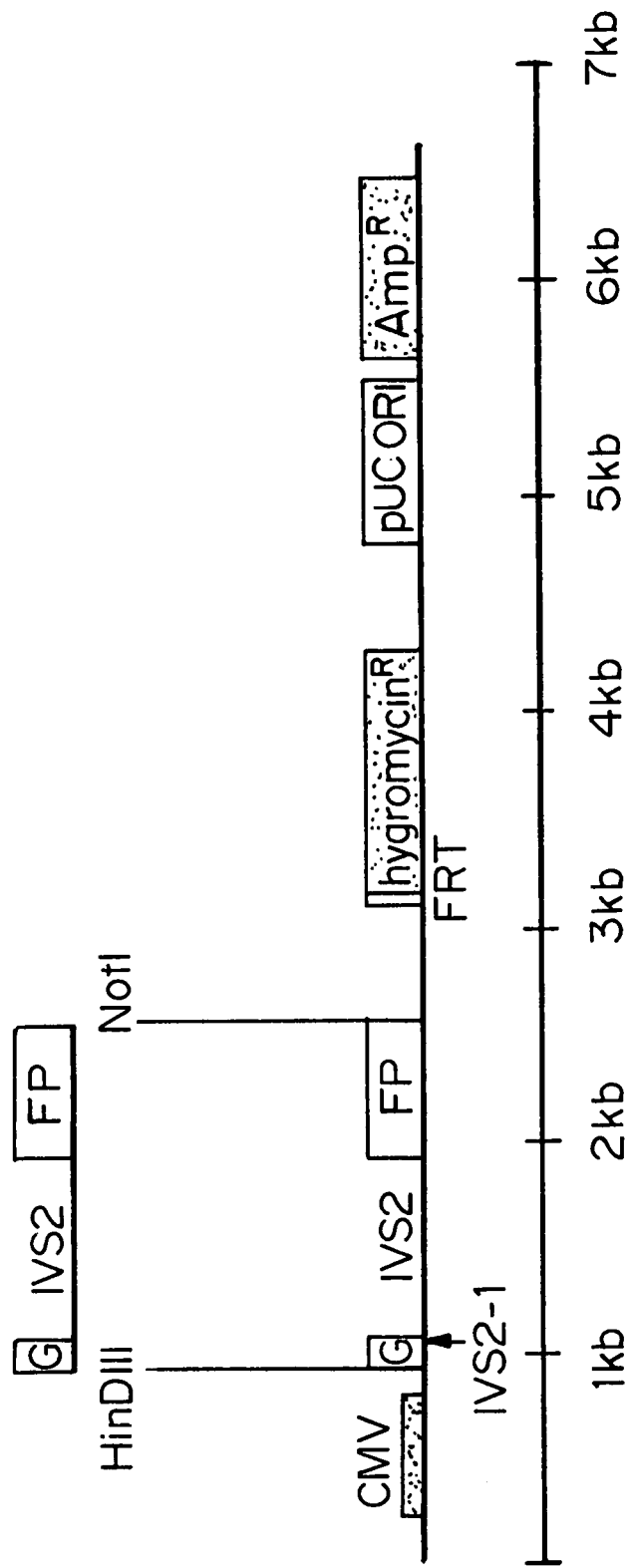
FIG. 8 is a schematic showing the plasmid maps of pcDNA/FRT-GFP-IVS2-1 wt and pcDNA/FRT-GFP-IVS2-1mut. The site of the G to A mutation in the pcDNA/FRT-GFP-IVS2-1mut plasmid at position IVS2-1 (the first nucleotide of the IVS2 sequence) is indicated by an arrow. The plasmid is depicted as linear for illustration purposes, but is, in fact, circular.

GFP-based reporter CHO cell lines were established that provide a fluorescent readout for gene correction. CHO cell lines were generated that stably express pGFP-IVS2-1 (G/A) and pGFP-IVS2wt. These constructs were generated by interrupting the GFP gene contained in pEGFP-N1 (Clontech, Palo Alto, Calif.) with either the wild-type β-globin IVS2 intron or a mutant IVS2 intron containing a G to A mutation at position 1 of the intron. The IVS2 intron was inserted 105 nt downstream of the ATG translation start sequence of the GFP coding region. The HinDIII-NotI fragment of these plasmids (containing the GFP-IVS2 construct) were inserted into the multiple cloning site of pcDNA5/FRT (Invitrogen, Carlsbad, Calif.) to generate pcDNA5/FRT-GFP-IVS2-1mut and pcDNA5/FRT-GFP-IVS2wt (FIG. 8).

Cell Lines.

CHO-Flp cells were obtained form Invitrogen (Carlsbad, Calif.) and maintained in Ham's F12 media supplemented with 10% bovine serum (FBS), 2 mM L-glutamine, and 100 µg/mL Zeocin (Invitrogen). pcDNA5/FRT-GFP-IVS2-1mut or pcDNA5/FRT-GFP-IVS2wt plasmids were co-transfected into CHO-Flp cells with plasmid pOG44 which expresses FLP recombinase. Upon transfection, the expression of Flp recombinase mediates homologous recombination events between the FRT sites in the genome and on the pcDNA5/FRT plasmids in order to generate cell lines containing a single-copy of the GFP-IVS2-1mut or GFP-IVS2wt gene at a defined genomic locus (i.e. the FRT site in the original CHO-Flp cell lines). Following co-transfection, the cells were selected for 2-3 weeks in 600 µg/mL Hygromycin B in full media without Zeocin. Clones were isolated from single colonies formed during selection. This resulted in the creation of isogenic cell lines containing the desired inserts. Isolated clones were subjected to a β-gal staining assay for loss of β-galactosidase activity that indicates proper insertion of the plasmid into the genome at the integrated FRT site rather than random genomic insertion. Southern blot analysis confirmed that the constructed were integrated as a single-copy. CHO cells expressing GFP flanking a mutant β-globin IVS2 intron (CHOFLP-GFP-IVS2-1mut) show very low background GFP expression while those with the wildtype IVS2 intron (CHOFLP-GFP-IVS2wt) demonstrate high-level GFP expression as observed using fluorescent microscopy and fluorescence activated cell sorting (FACS). Post selection, CHOFLP cell lines were maintained in Ham's F12 media supplemented with 10% FBS and 2 mM L-glutamine.

β-Galalactosidase Staining Assay.

Cells were seeded the day before the assay in 6-well plates and 80% confluent on the day of staining. Cells were washed once with PBS and fixed for 10 minutes in a fixative solution containing 2% formaldehyde and 0.2% glutaraldehyde made in PBS. After fixation, cells were washed twice with PBS and incubated at 37° C. for 1 hour in a staining solution containing 4 mM potassium ferricyanide, 4 mM potassium ferrocyanide, and 2 mM magnesium chloride, and 0.2 mg/ml, 5-bromo-4-chloro-3-indolyl-β-D-galactopyranoside (X-gal) made in PBS, pH 6.0. Cells were observed under a microscope for development of blue color.

Fluorescence Microscopy, FACS, and Live Flow Cytometry.

Cells were visualized using a Zeiss Axiovert 200 (Thornwood, N.Y.) fluorescent microscope at 100× and 200× magnification. Cells for GFP FACS analysis were trypsinized, washed once in PBS, and fixed for at least 2 hours at 4° C. in 2% paraformaldehyde made in PBS. Prior to FACS, the cells were pelleted and resuspended in PBS. Cells were analyzed using a Becton Dickinson FACSCalibur flow cytometer (Franklin Lakes, N.J.). Collected data were then analyzed using the FlowJo software (Tree Star Inc., Ashland, Oreg.). Settings and gating parameters were based on a protocol from Methods in Molecular Biology. Briefly, a gate on SSC (side scatter) vs. FSC (forward scatter) was set to select for cells with a well-defined size and shape, taking care to eliminate debris and clumps. A second gate was then drawn using the CHOFLP-GFP-IVS2-1mut cells as a negative control to include no more than 0.012% background. Nonfluorescent cells fall on the GFP/autofluorescence diagonal and cells expressing GFP are shifted higher on the Y-axis (GFP+). Cells analyzed by FACS for cell cycle stage/progression were fixed in cold methanol for 8 hours at 4° C., washed once in PBS, then resuspended and incubated for 20-30 minutes in the dark in a staining solution containing 0.1% TritonX-100, 1 µg/mL DNase-free Rnase, and 35 µg/mL propidium iodide (PI). Cell cycle data was analyzed using the ModFit LT software (Verity House, Topsham, Me.). Flow cytometry (live cell sorting) of samples was performed in the Yale University Cell Sorter Facility using a Becton Dickinson FACSVantage SE flow cytometer and cells were collected in Ham's F12 media supplemented with 20% FBS.

CHOFLP Cell Line Southern Blot.

Genomic DNA was purified from confluent plates of expanded hygromycin resistant clones using the Wizard Genomic DNA Purification kit (Promega, Madison, Wis.). DNA concentration was determined via $OD_{260}$ absorbance measurements and 25 µg of DNA was digested overnight with XhoI and EcoRI. Prior to electrophoresis, the DNA concentration was rechecked and 20 µg of digested genomic DNA was loaded into a 1% TAE agarose gel containing ethidium bromide and run overnight at 30V to allow for separation. Migration, completion of digestion, and equal loading of DNA was visualized on an ultraviolet light box. The agarose gel was then soaked in a denaturing solution (1.5 M NaCl, 0.5 N NaOH) and denatured for 30 minutes, neutralized (1 M Tris pH 7.4, 1.5 M NaCl) for 30 minutes, and soaked in 10×SSC transfer buffer (1.5M NaCl, 0.15 M Sodium Citrate) for another 30 minutes before being rinsed quickly with distilled water. Transfer onto Nytran SuPerCharge membrane was set up using the Turboblotter Rapid Downward Transfer System (Schleicher & Schuell, Dassel, Germany) and DNA was optimally crosslinked to the membrane in the UV Crosslinker FB-UVXL-1000 (Fisher Scientific, Hampton, N.H.) which delivers an energy dose of 120 mJ/cm$^2$. A probe was constructed by gel purification of the 1.6 kb XhoI/EcoRI fragment from digestion of pcDNA5/FRT-GFP-IVS2-1mut and internally labeled using the Random Primers DNA Labeling System (Invitrogen, Carlsbad, Calif.) in the presence of [α-32P]-dCTP. The membrane was prehybridized at 65° C. in PerfectHyb Plus solution (Sigma-Aldrich, St. Louis, Mo.) for 12 hours then hybridized for an additional 24 hours in the presence of labeled probe. Post hybridization, the membrane was rinsed several times in 2×SSC and 0.3% SDS and exposed to film.

CHOFLP-GFP cell line transfection by cationic lipid.

CHO cells were transfected with donor DNA using Geneporter 2 (Gene Therapy Systems Inc., San Diego, Calif.) per manufacturer's protocol. Briefly, 1-1.5×10$^5$ cells were seeded in a 60 mm dish, 24 hours prior to transfection. On the day of transfection, the indicated amount of DNA was complexed with Geneporter 2 and added to the appropriate plates. Cells were expanded to 90% confluence (2-3 days) and were then visualized via fluorescence microscopy and harvested for analysis by FACS.

CHOFLP-GFP Cell Line Transfection by Electroporation.

1×10$^6$ cells in 100 μL volume of media are mixed with TFO, PNA, donor DNA or TE (not DNA control), as indicated, and electroporated in a 0.4 cm cuvette using a Bio-Rad Gene Pulser (Hercules, Calif.) set at 280V, 960 μFd capacitance, 200 ohms (Ω) resistance. Cells were replated in 60 mm dishes following electroporation and allowed to expand to ~90% confluency (2-3 days). They were then visualized via fluorescence microscopy and analyzed by FACS.

Synchronization of CHO Cells by Serum Starvation.

CHO cells were synchronized in G0/G1 phase by plating 1×10$^6$ cells on a 10 cm dish in Ham's F12 media containing 5% FBS and 2 mM L-glutamine for 24 hours, then washing three times in PBS and changing the media to Ham's F12 with 0.1% FBS and 2 mM L-glutamine for 72 additional hours. Cells were then released by trypsinization and replated in full media containing 10% serum.

Total RNA Isolation and Reverse Transcription-PCR (RT-PCR) Analysis. Total RNA was isolated from expanded GFP-positive flow-sorted cells using TRIzol Reagent (Invitrogen, Carlsbad, Calif.). Messenger RNA transcripts were then analyzed by reverse transcription-PCR (RT-PCR) on 50 ng purified total RNA with primers pJK115 and pJK118 using the SuperScript One-Step RT-PCR kit (Invitrogen) and subsequent analysis of the products by electrophoresis on a 1.7% TAE agarose gel. This technique is used to detect and differentiate between wildtype mRNA transcript produced by cells containing a correctly spliced wildtype β-globin IVS2 and mutant mRNA transcript produced by cells containing an incorrectly spliced mutant β-globin IVS2. A G to A mutation at position IVS2-1 results in the insertion of an additional 47 nt of IVS2 intron sequence as this mutation disrupts the 5'donor splice site, activating a cryptic splice site downstream.

Sequence Analysis of Genomic DNA.

Genomic DNA was purified from expanded GFP-positive flow-sorted cells using the Wizard Genomic DNA Purification kit (Promega, Madison, Wis.) and the GFP-IVS2 region was amplified using primers pJK115 and pJK118. The resulting PCR products were gel purified and sequenced with forward primer pJK115.

Results:

Cell Lines Containing GFP Interrupted by Wildtype β-Globin IVS2 Sequence Exhibit High Level GFP Expression.

Cells lines were generated which could be used to assay for gene conversion events in live cells stimulated by the addition of sequence-specific TFOs or PNAs. Intron 2 (also referred to as IVS2) of the human β-globin gene was selected as a model target sequence as above in Examples 1-3. A β-thalessemia-related point mutation in IVS2 was chosen as a model for gene conversion events. This mutation, from A to G at basepair 1 of IVS2 disrupts the 5' donor site and prevents normal splicing of this intron. Instead, a cryptic spice site 3' to basepair 1 becomes activated, resulting in the insertion of 47 nucleotides of IVS2 intron sequence in the spiced mRNA. The wild-type IVS2 sequence or the mutant (A to G at position 1) IVS2 sequence was inserted 105 nucleotides downstream of the ATG translation start site of the green fluorescent protein (GFP) coding region. The disrupted GFP constructs were then stably transfected into Chinese hamster ovary (CHO) cells using the FRT-FLP system. This resulted in the cell lines CHOFLP-GFP-IVS2wt and CHOFLP-GFP-IVS2-1mut containing GFP coding sequence disrupted with the wild-type and mutant IVS2 sequence, respectively. It was reasoned that the wild-type IVS2 sequence would be properly spliced out of the GFP coding region, thus allowing for GFP expression and fluorescence in the CHOFLP-GFP-IVS2wt cells. In contrast, it was predicted that the mutated IVS2 sequence would fail to be spliced out of the GFP coding sequence in the CHOFLP-GFP-IVS2-1mut cells, and thus the resulting GFP would fail to fold properly and fail to fluoresce. This system provided a way to assay for gene conversion events in living cells in which reversion of the mutated splice site in IVS2 to wild-type could be assayed for based on the appearance of GFP fluorescence.

CHOFLP-GFP-IVS2wt cells containing the GFP reporter construct interrupted by wild-type β-globin IVS2 sequence exhibited high-level GFP expression as observed by FACS and microscopy. Genomic DNA sequenced at the GFP-IVS2 junction had a wildtype G at the IVS2-1 position, as expected. Greater than 95% of the cells containing the GFP construct interrupted by IVS2wt fluoresce, suggesting that fluorescence would be observed if a gene conversion event reversion of mutant A to wildtype G) takes place at the IVS2-1 position CHOFLP-GFP-IVS2-1mut cells did not demonstrate any fluorescence when assayed by FACS or fluorescence microscopy.

PNA Alone and Unrelated Donor Sequences do not Induce Recombination Over Cell Background.

Figure 9A:
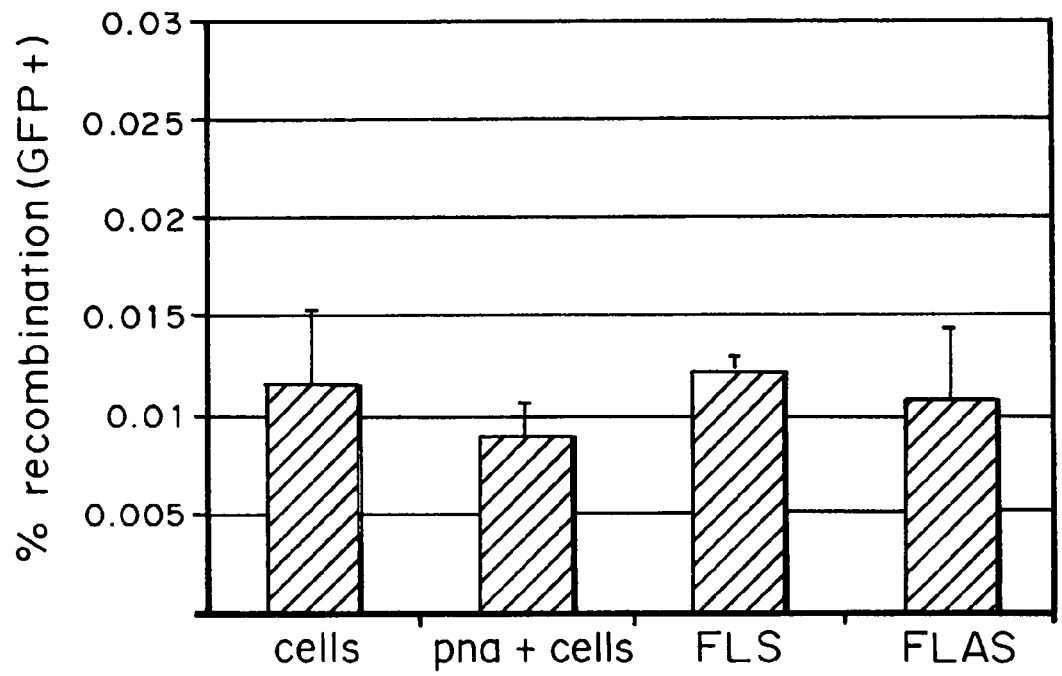
FIG. 9A is a graph showing percent recombination in cells electroporated with either PNA 2844 or randomized 50 mer single-stranded donor molecules (FLS or FLAS) alone. Recombination was scored as a percentage of cells expressing GFP fluorescence over background levels.

Potential background effects of PNA molecules or donor oligomers containing random sequences on gene conversion events were checked for in the CHOFLP-GFP-IVS2-1mut cell line. Cells were electroporated with either PNA 2844 or 50 mer donor molecules FLAS or FLS (whose sequences do not correspond to any portion of the GFP-IVS2 construct) and were subsequently analyzed by FACS. Results indicated that the addition of PNA alone or either of the donor molecules did not induce recombination and GFP-positive signal was not detected over cell background alone (FIG. 9A).

Single-Stranded Donor Oligomers Alone Induce Recombination Over Cell Background.

Single-stranded donor molecules 50 bp in length were generated containing the wildtype GFP-IVS2 sense and antisense sequence. These oligomers can cause gene conversion in the absence of TFO- or PNA-induced repair, demonstrating that the presence of these molecules alone stimulates some recombination. At this site there does not appear to be a significant strand preference for either the sense (FIG. 9B) or antisense donor sequence (FIG. 9C), as either donor electroporated at 8 μM (12 μg) stimulated similar recombination frequencies in the 0.015-0.025% range, approximately 2- to 3-fold over background. Background fluorescence was between 0.005-0.01%. The gene conversion frequencies also appeared to be dose dependent, as donor concentrations less than 3 μM did not have a visible effect.

Addition of PNA or Cationic α-Oligomers Enhances Recombination by a Single-Stranded Donor.

Figure 9B:
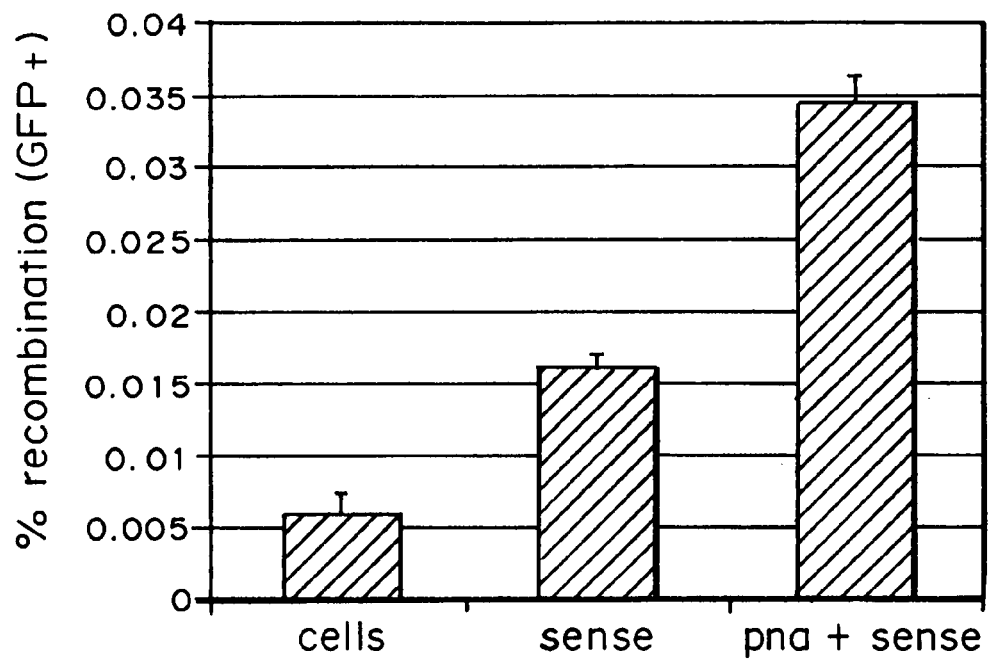
FIG. 9B is a graph showing percent recombination in cells electroporated either with single-stranded sense donor alone or together with PNA 2844. Recombination was scored as a percentage of cells expressing GFP fluorescence over background levels.
Figure 9C:
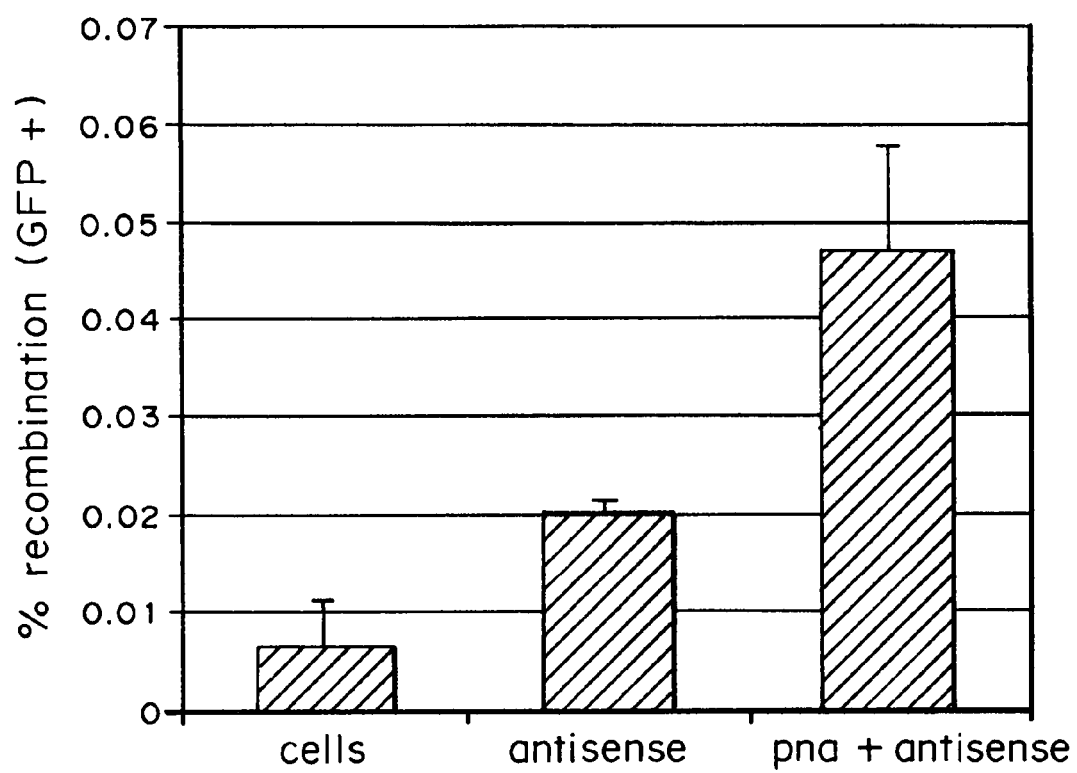
FIG. 9C is a graph showing percent recombination in cells electroporated either with single-stranded antisense donor alone or together with PNA 2844. Recombination was scored as a percentage of cells expressing GFP fluorescence over background levels.

A pair of PNAs designed to IVS2-24 (PNA 2843 and PNA 2844) were shown to bind the β-globin IVS2-24 target site with high affinity using in vitro binding assays in Example 2. Co-transfection of these sequence-specific PNAs with the single stranded 50-mer donor molecule stimulates recombination an additional 2- to 2.5-fold into the 0.04-0.05% range (FIGS. 9B and 9C). Although it was demonstrated that the psoralen-conjugated version of the IVS2-24 PNA (PNA 2844) was capable of generating interstrand crosslinks in vitro, UVA irradiation following electroporation of the PNAs did not further enhance their effect. This suggests that crosslinking of the duplex is unnecessary and the PNA clamp structure is recombinogenic enough, by itself, to stimulate gene conversion. Therefore, subsequent experiments omitted this irradiation step. Both sense and antisense molecules performed similarly in these assays.

Figure 10A:
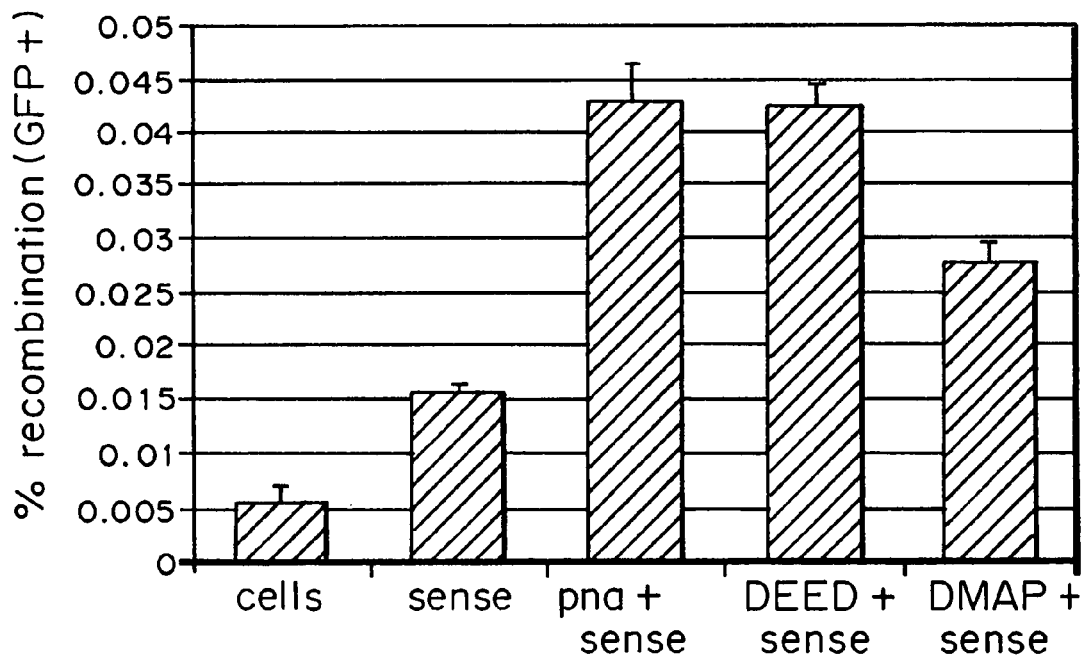
FIG. 10A is a graph showing percent recombination in cells electroporated with either single-stranded sense donor alone or together with either αDEED 2-24, αDMAP 2-24 or PNA 2844. Recombination was scored as a percentage of cells expressing GFP fluorescence over background levels.
Figure 10B:
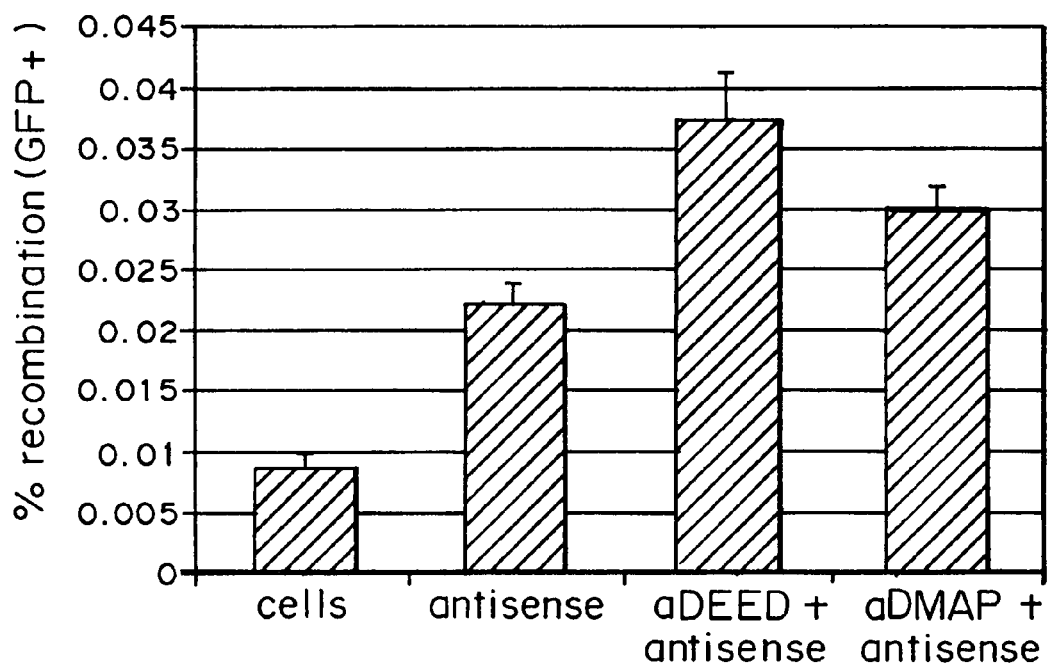
FIG. 10B is a graph showing percent recombination in cells electroporated with either single-stranded antisense donor alone or together with either αDEED 2-24, αDMAP 2-24 or PNA 2844. Recombination was scored as a percentage of cells expressing GFP fluorescence over background levels.

Chemically modified cationic α-ligomers also demonstrated about a 2-fold enhancement of recombination over donor molecules alone to approximately 0.04%. This effect was not as robust using antisense donors (FIG. 10B) as with the sense donors (FIG. 10A) indicating a slight strand preference. Moreover, the oligomer containing the diethyl-ethylenediamine (DEED) linkages had a greater effect than the corresponding dimethyl-aminopropylamine (DMAP) oligo which is consistent with the increased binding affinity that αDEED 2-24 oligos demonstrated in vitro compared to the αDMAP 2-24.

RT-PCR of Sorted Cells Indicates a Restoration of Correct Splicing at the mRNA Level.

A G to A mutation at position IVS2-1 results in the insertion of an additional 47 nt of IVS2 intron sequence as this mutation disrupts the 5'donor splice site, activating a cryptic splice site downstream. This difference in length can be detected by RT-PCR of mRNA transcripts and can be used to differentiate between cells containing a wildtype intron and those carrying the IVS2-1 G to A mutation.

Total RNA was isolated from GFP positive sorted cells which were treated with either PNA or αDEED 2-24 in combination with sense donor and subjected to RT-PCR. The cells which were subjected to two rounds of sorting for GFP expression showed near 100% wildtype mRNA transcript.

Sequencing of the GFP-IVS2 Junction Indicates a Reversion of the IVS2-1 Mutation.

In order to demonstrate gene conversion at the genomic level of the GFP-IVS2 junction mutation, the GFP-IVS2 region was PCR amplified from the pooled genomic DNA of the GFP positive cells sorted above for sequencing. The uncloned PCR products were then sequenced using primers flanking the GFP-IVS2 junction. Sequencing data showed the expected sequence change from a mutant A to a wild-type G at position IVS2-1.

We claim:

1. A recombinagenic or mutagenic composition comprising
   a single-stranded oligonucleotide that binds to a polypyrimidine:polypurine target motif in a double stranded nucleic acid molecule in a beta globin gene to form a triple-stranded nucleic acid molecule,
   wherein the polypyrimidine strand of the polypyrimidine:polypurine target motif comprises from nucleotide 837 to nucleotide 846 of SEQ ID NO:59 or nucleotide 774 to nucleotide 787 of SEQ ID NO:60,
   wherein the single-stranded oligonucleotide comprises a sequence substantially complementary to the polypurine strand of the polypyrimidine:polypurine target motif, and
   wherein the single stranded oligonucleotide comprises one or more chemically modified cytosine nucleotides substituted for one or more cytosine nucleotides and has increased triplex stability at neutral pH relative to the single-stranded oligonucleotide in the absence of the substituted cytosine nucleotides.

2. The recombinagenic or mutagenic composition of claim 1 further comprising a donor nucleic acid.

3. The recombinagenic or mutagenic composition of claim 2 wherein the donor nucleic acid is single stranded or double stranded.

4. The composition of claim 3 wherein the donor nucleic acid comprises one or more phosphorothioate linkages.

5. The composition of claim 2 wherein the donor nucleic acid is tethered to the single stranded oligonucleotide.

6. The composition of claim 2 wherein the donor nucleic acid is separate from the single stranded oligonucleotide.

7. The composition of claim 1 wherein the single stranded oligonucleotide is between 10 and 60 nucleotides residues in length.

8. The composition of claim 1 wherein the single stranded oligonucleotide comprises a chemically modified sugar moiety selected from the group consisting of 2'-O-aminoethoxy, 2'-O-amonioethyl, 2'-O-methoxy, 2'-O-methyl, 2-guanidoethyl, 2'-O,4'-C-methylene, 2'-O-(methoxyethyl) and 2'-O—(N-(methyl)acetamido).

9. The composition of claim 1 wherein the single stranded oligonucleotide comprises a chemically modified phosphate moiety selected from the group consisting of diethyl-ethylenediamide and dimethyl-aminopropylamine.

10. The composition of claim 1 wherein the single stranded oligonucleotide comprises a peptide nucleic acid monomer.

11. The composition of claim 10 wherein the single stranded oligonucleotide comprises peptide nucleic acid monomers positioned in the oligonucleotide to form a bis-peptide nucleic acid.

12. A cell comprising the recombinagenic or mutagenic composition of claim 1.

13. A method for targeted recombination or mutation of a nucleic acid molecule comprising administering to cells or an individual an effective amount of the recombinagenic or mutagenic composition of claim 1 to induce mutation or recombination in a double stranded nucleic acid molecule in the cells or individual.

14. The method of claim 13 wherein the targeted recombination or mutation corrects a point mutation in the human β-globin gene and restores the DNA sequence of the human β-globin gene to normal.

15. The method of claim 14 wherein the point mutation in the human β-globin gene is associated with sickle cell anemia or β-thalassemia.

16. The recombinagenic or mutagenic composition of claim 1 wherein the double-stranded nucleic acid molecule is a defective β-hemoglobin gene.

17. The recombinogenic or mutagenic composition of claim 1 wherein the one or more chemically modified cytosines are selected from the group consisting of pseudocytosine, pseudoisocytosine, and 5-methylcytosine.

18. The recombinagenic or mutagenic composition of claim 11 wherein the bis-peptide nucleic acid comprises SEQ ID NO:49.

19. The recombinagenic or mutagenic composition of claim 2 wherein the donor oligonucleotide is selected from the group consisting of SEQ ID NO:50 and SEQ ID NO:51.

20. The recombinagenic or mutagenic composition of claim 16 wherein the defect in the β-hemoglobin gene is caused by a point mutation in intron two of the human β-hemoglobin gene.

21. The recombinagenic or mutagenic composition of claim 20 wherein the point mutation is in position one of intron two of the human β-hemoglobin gene.

22. The method of claim 15 wherein the defect in the β-hemoglobin gene is caused by a point mutation in intron two of the human β-hemoglobin gene.

23. The method of claim 22 wherein the point mutation is in position one of intron two of the human β-hemoglobin gene.

* * * * *

SEQUENCE LISTING

<160> NUMBER OF SEQ ID NOS: 60

<210> SEQ ID NO 1
<211> LENGTH: 21
<212> TYPE: DNA
<213> ORGANISM: Artificial Sequence
<220> FEATURE:
<223> OTHER INFORMATION: Triple helix forming oligonucleotide
<220> FEATURE:
<221> NAME/KEY: misc_feature
<222> LOCATION: (1)..(21)
<223> OTHER INFORMATION: deoxy sugar
<220> FEATURE:
<221> NAME/KEY: modified_base
<222> LOCATION: (2)..(2)
<223> OTHER INFORMATION: 5-methyl cytosine
<220> FEATURE:
<221> NAME/KEY: modified_base
<222> LOCATION: (7)..(7)
<223> OTHER INFORMATION: 5-methyl cytosine
<220> FEATURE:
<221> NAME/KEY: modified_base
<222> LOCATION: (10)..(13)
<223> OTHER INFORMATION: 5-methyl cytosine
<220> FEATURE:
<221> NAME/KEY: modified_base
<222> LOCATION: (17)..(17)
<223> OTHER INFORMATION: 5-methyl cytosine

<400> SEQUENCE: 1
tcttttcttc ccctttcttt t                                             21

<210> SEQ ID NO 2
<211> LENGTH: 21
<212> TYPE: DNA
<213> ORGANISM: Artificial Sequence
<220> FEATURE:
<223> OTHER INFORMATION: Triple-forming oligonucleotide

```
<220> FEATURE:
<221> NAME/KEY: misc_feature
<222> LOCATION: (1)..(21)
<223> OTHER INFORMATION: deoxy sugar

<400> SEQUENCE: 2
aaaagaaagg ggaagaaaag a                                              21

<210> SEQ ID NO 3
<211> LENGTH: 21
<212> TYPE: RNA
<213> ORGANISM: Artificial Sequence
<220> FEATURE:
<223> OTHER INFORMATION: Triple-forming oligonucleotide
<220> FEATURE:
<221> NAME/KEY: modified_base
<222> LOCATION: (1)..(1)
<223> OTHER INFORMATION: 5-(1-propynyl)-2'-deoxyuridine
<220> FEATURE:
<221> NAME/KEY: misc_feature
<222> LOCATION: (1)..(21)
<223> OTHER INFORMATION: deoxy sugar
<220> FEATURE:
<221> NAME/KEY: modified_base
<222> LOCATION: (2)..(2)
<223> OTHER INFORMATION: 5-methyl cytosine
<220> FEATURE:
<221> NAME/KEY: modified_base
<222> LOCATION: (3)..(6)
<223> OTHER INFORMATION: 5-(1-propynyl)-2'-deoxyuridine
<220> FEATURE:
<221> NAME/KEY: modified_base
<222> LOCATION: (7)..(7)
<223> OTHER INFORMATION: 5-methyl cytosine
<220> FEATURE:
<221> NAME/KEY: modified_base
<222> LOCATION: (8)..(9)
<223> OTHER INFORMATION: 5-(1-propynyl)-2'-deoxyuridine
<220> FEATURE:
<221> NAME/KEY: modified_base
<222> LOCATION: (10)..(13)
<223> OTHER INFORMATION: 5-methyl cytosine
<220> FEATURE:
<221> NAME/KEY: modified_base
<222> LOCATION: (14)..(16)
<223> OTHER INFORMATION: 5-(1-propynyl)-2'-deoxyuridine
<220> FEATURE:
<221> NAME/KEY: modified_base
<222> LOCATION: (17)..(17)
<223> OTHER INFORMATION: 5-methyl cytosine
<220> FEATURE:
<221> NAME/KEY: modified_base
<222> LOCATION: (18)..(21)
<223> OTHER INFORMATION: 5-(1-propynyl)-2'-deoxyuridine

<400> SEQUENCE: 3
ucuuuucuuc cccuuucuuu u                                              21

<210> SEQ ID NO 4
<211> LENGTH: 21
<212> TYPE: DNA
<213> ORGANISM: Artificial Sequence
<220> FEATURE:
<223> OTHER INFORMATION: Triple-forming oligonucleotide
<220> FEATURE:
<221> NAME/KEY: modified_base
<222> LOCATION: (1)..(1)
<223> OTHER INFORMATION: 5-methyluridine
<220> FEATURE:
<221> NAME/KEY: misc_feature
<222> LOCATION: (1)..(1)
<223> OTHER INFORMATION: 2-guanidoethyl-sugar modification
<220> FEATURE:
<221> NAME/KEY: misc_feature
<222> LOCATION: (2)..(2)
<223> OTHER INFORMATION: 2'-O-methyl sugar modification
```

-continued

```
<220> FEATURE:
<221> NAME/KEY: modified_base
<222> LOCATION: (2)..(2)
<223> OTHER INFORMATION: 5-methyl cytosine
<220> FEATURE:
<221> NAME/KEY: modified_base
<222> LOCATION: (3)..(6)
<223> OTHER INFORMATION: 5-methyluridine
<220> FEATURE:
<221> NAME/KEY: misc_feature
<222> LOCATION: (3)..(6)
<223> OTHER INFORMATION: 2-guanidoethyl-sugar modification
<220> FEATURE:
<221> NAME/KEY: misc_feature
<222> LOCATION: (7)..(20)
<223> OTHER INFORMATION: 2'-O-methyl sugar modification
<220> FEATURE:
<221> NAME/KEY: modified_base
<222> LOCATION: (7)..(7)
<223> OTHER INFORMATION: 5-methyl cytosine
<220> FEATURE:
<221> NAME/KEY: modified_base
<222> LOCATION: (10)..(13)
<223> OTHER INFORMATION: 5-methyl cytosine
<220> FEATURE:
<221> NAME/KEY: modified_base
<222> LOCATION: (17)..(17)
<223> OTHER INFORMATION: 5-methyl cytosine
<220> FEATURE:
<221> NAME/KEY: modified_base
<222> LOCATION: (21)..(21)
<223> OTHER INFORMATION: 5-methyluridine
<220> FEATURE:
<221> NAME/KEY: misc_feature
<222> LOCATION: (21)..(21)
<223> OTHER INFORMATION: 2-guanidoethyl-sugar modification

<400> SEQUENCE: 4
ucuuuucuuc ccctttcttt u                                              21

<210> SEQ ID NO 5
<211> LENGTH: 21
<212> TYPE: DNA
<213> ORGANISM: Artificial sequence
<220> FEATURE:
<223> OTHER INFORMATION: TRiple-helix forming nucleotide
<220> FEATURE:
<221> NAME/KEY: misc_feature
<222> LOCATION: (1)..(20)
<223> OTHER INFORMATION: 2'-O-(2-methxyethyl) sugar modification
<220> FEATURE:
<221> NAME/KEY: modified_base
<222> LOCATION: (2)..(2)
<223> OTHER INFORMATION: 5-methyl cytosine
<220> FEATURE:
<221> NAME/KEY: modified_base
<222> LOCATION: (7)..(7)
<223> OTHER INFORMATION: 5-methyl cytosine
<220> FEATURE:
<221> NAME/KEY: modified_base
<222> LOCATION: (10)..(13)
<223> OTHER INFORMATION: 5-methyl cytosine
<220> FEATURE:
<221> NAME/KEY: modified_base
<222> LOCATION: (17)..(17)
<223> OTHER INFORMATION: 5-methyl cytosine
<220> FEATURE:
<221> NAME/KEY: misc_feature
<222> LOCATION: (21)..(21)
<223> OTHER INFORMATION: 3'-O-(2-methxyethyl) sugar modification

<400> SEQUENCE: 5
tcttttcttc ccctttcttt u                                              21

<210> SEQ ID NO 6
<211> LENGTH: 20
```

```
-continued

<212> TYPE: DNA
<213> ORGANISM: Artificial Sequence
<220> FEATURE:
<223> OTHER INFORMATION: Triple-forming oligonucleotide
<220> FEATURE:
<221> NAME/KEY: misc_feature
<222> LOCATION: (1)..(9)
<223> OTHER INFORMATION: 2'-O-methyl sugar modification
<220> FEATURE:
<221> NAME/KEY: modified_base
<222> LOCATION: (2)..(2)
<223> OTHER INFORMATION: 5-methyl cytosine
<220> FEATURE:
<221> NAME/KEY: modified_base
<222> LOCATION: (7)..(7)
<223> OTHER INFORMATION: 5-methyl cytosine
<220> FEATURE:
<221> NAME/KEY: misc_feature
<222> LOCATION: (10)..(13)
<223> OTHER INFORMATION: 2'-aminoethoxy sugar modification
<220> FEATURE:
<221> NAME/KEY: modified_base
<222> LOCATION: (10)..(13)
<223> OTHER INFORMATION: 5-methyl cytosine
<220> FEATURE:
<221> NAME/KEY: misc_feature
<222> LOCATION: (10)..(13)
<223> OTHER INFORMATION: 2'-O-aminoethoxy sugar
<220> FEATURE:
<221> NAME/KEY: misc_feature
<222> LOCATION: (14)..(20)
<223> OTHER INFORMATION: 2'-O-methyl sugar modification
<220> FEATURE:
<221> NAME/KEY: modified_base
<222> LOCATION: (17)..(17)
<223> OTHER INFORMATION: 5-methyl cytosine

<400> SEQUENCE: 6
tcttttcttc ccctttcttt                                              20

<210> SEQ ID NO 7
<211> LENGTH: 21
<212> TYPE: DNA
<213> ORGANISM: Artificial Sequence
<220> FEATURE:
<223> OTHER INFORMATION: Triple-forming oligonucleotide
<220> FEATURE:
<221> NAME/KEY: misc_feature
<222> LOCATION: (1)..(10)
<223> OTHER INFORMATION: 2'-O-methyl sugar modification
<220> FEATURE:
<221> NAME/KEY: modified_base
<222> LOCATION: (2)..(2)
<223> OTHER INFORMATION: 5-methyl cytosine
<220> FEATURE:
<221> NAME/KEY: modified_base
<222> LOCATION: (7)..(7)
<223> OTHER INFORMATION: 5-methyl cytosine
<220> FEATURE:
<221> NAME/KEY: modified_base
<222> LOCATION: (10)..(13)
<223> OTHER INFORMATION: 5-methyl cytosine
<220> FEATURE:
<221> NAME/KEY: misc_feature
<222> LOCATION: (11)..(12)
<223> OTHER INFORMATION: 2'-O-aminoethoxy sugar
<220> FEATURE:
<221> NAME/KEY: misc_feature
<222> LOCATION: (13)..(21)
<223> OTHER INFORMATION: 2'-O-methyl sugar modification
<220> FEATURE:
<221> NAME/KEY: modified_base
<222> LOCATION: (17)..(17)
<223> OTHER INFORMATION: 5-methyl cytosine

<400> SEQUENCE: 7
tcttttcttc ccctttcttt t                                            21
```

```
<210> SEQ ID NO 8
<211> LENGTH: 21
<212> TYPE: DNA
<213> ORGANISM: Artificial Sequence
<220> FEATURE:
<223> OTHER INFORMATION: Triple-forming oligonucleotide
<220> FEATURE:
<221> NAME/KEY: misc_feature
<222> LOCATION: (1)..(21)
<223> OTHER INFORMATION: deoxy sugar

<400> SEQUENCE: 8
tgttttgttg gggtttgttt t                                              21

<210> SEQ ID NO 9
<211> LENGTH: 21
<212> TYPE: DNA
<213> ORGANISM: Artificial Sequence
<220> FEATURE:
<223> OTHER INFORMATION: Triple-forming oligonucleotide
<220> FEATURE:
<221> NAME/KEY: misc_feature
<222> LOCATION: (1)..(1)
<223> OTHER INFORMATION: 2'-O,4'-C-methylene ribose
<220> FEATURE:
<221> NAME/KEY: misc_feature
<222> LOCATION: (3)..(3)
<223> OTHER INFORMATION: 2'-O,4'-C-methylene ribose
<220> FEATURE:
<221> NAME/KEY: misc_feature
<222> LOCATION: (5)..(5)
<223> OTHER INFORMATION: 2'-O,4'-C-methylene ribose
<220> FEATURE:
<221> NAME/KEY: misc_feature
<222> LOCATION: (7)..(7)
<223> OTHER INFORMATION: 2'-O,4'-C-methylene ribose
<220> FEATURE:
<221> NAME/KEY: misc_feature
<222> LOCATION: (9)..(9)
<223> OTHER INFORMATION: 2'-O,4'-C-methylene ribose
<220> FEATURE:
<221> NAME/KEY: misc_feature
<222> LOCATION: (11)..(11)
<223> OTHER INFORMATION: 2'-O,4'-C-methylene ribose
<220> FEATURE:
<221> NAME/KEY: misc_feature
<222> LOCATION: (13)..(13)
<223> OTHER INFORMATION: 2'-O,4'-C-methylene ribose
<220> FEATURE:
<221> NAME/KEY: misc_feature
<222> LOCATION: (15)..(15)
<223> OTHER INFORMATION: 2'-O,4'-C-methylene ribose
<220> FEATURE:
<221> NAME/KEY: misc_feature
<222> LOCATION: (17)..(17)
<223> OTHER INFORMATION: 2'-O,4'-C-methylene ribose
<220> FEATURE:
<221> NAME/KEY: misc_feature
<222> LOCATION: (19)..(19)
<223> OTHER INFORMATION: 2'-O,4'-C-methylene ribose
<220> FEATURE:
<221> NAME/KEY: misc_feature
<222> LOCATION: (21)..(21)
<223> OTHER INFORMATION: 2'-O,4'-C-methyl ribose

<400> SEQUENCE: 9
tcttttcttc ccctttcttt t                                              21

<210> SEQ ID NO 10
<211> LENGTH: 21
<212> TYPE: RNA
<213> ORGANISM: Artificial Sequence
<220> FEATURE:
<223> OTHER INFORMATION: Triplex-forming oligonucleotide
```

```
<220> FEATURE:
<221> NAME/KEY: modified_base
<222> LOCATION: (1)..(1)
<223> OTHER INFORMATION: 5-methyl uridine
<220> FEATURE:
<221> NAME/KEY: misc_feature
<222> LOCATION: (1)..(20)
<223> OTHER INFORMATION: 2'-O-(N-(nethyl)acetomido) sugar modification
<220> FEATURE:
<221> NAME/KEY: modified_base
<222> LOCATION: (2)..(2)
<223> OTHER INFORMATION: 5-methyl cytosine
<220> FEATURE:
<221> NAME/KEY: modified_base
<222> LOCATION: (3)..(6)
<223> OTHER INFORMATION: 5-methyl uridine
<220> FEATURE:
<221> NAME/KEY: modified_base
<222> LOCATION: (7)..(7)
<223> OTHER INFORMATION: 5-methyl cytosine
<220> FEATURE:
<221> NAME/KEY: modified_base
<222> LOCATION: (8)..(9)
<223> OTHER INFORMATION: 5-methyl uridine
<220> FEATURE:
<221> NAME/KEY: modified_base
<222> LOCATION: (10)..(13)
<223> OTHER INFORMATION: 5-methyl cytosine
<220> FEATURE:
<221> NAME/KEY: modified_base
<222> LOCATION: (14)..(16)
<223> OTHER INFORMATION: 5-methyl uridine
<220> FEATURE:
<221> NAME/KEY: modified_base
<222> LOCATION: (17)..(17)
<223> OTHER INFORMATION: 5-methyl cytosine
<220> FEATURE:
<221> NAME/KEY: modified_base
<222> LOCATION: (18)..(21)
<223> OTHER INFORMATION: 5-methyl uridine

<400> SEQUENCE: 10 ucuuucuuc cccuuucuuu u                                       21

<210> SEQ ID NO 11
<211> LENGTH: 21
<212> TYPE: DNA
<213> ORGANISM: Artificial Sequence
<220> FEATURE:
<223> OTHER INFORMATION: Triple-forming oligonucleotide
<220> FEATURE:
<221> NAME/KEY: misc_feature
<222> LOCATION: (21)..(21)
<223> OTHER INFORMATION: morpholino sugar modification

<400> SEQUENCE: 11
tcttttcttc ccctttctttt t                                     21

<210> SEQ ID NO 12
<211> LENGTH: 18
<212> TYPE: DNA
<213> ORGANISM: Artificial Sequence
<220> FEATURE:
<223> OTHER INFORMATION: Triple-forming oligonucleotide
<220> FEATURE:
<221> NAME/KEY: misc_feature
<222> LOCATION: (1)..(18)
<223> OTHER INFORMATION: diethylethlenediamide backbone modification

<400> SEQUENCE: 12
agaaagggga agaaaaga                                          18

<210> SEQ ID NO 13
<211> LENGTH: 28
```

```
<212> TYPE: DNA
<213> ORGANISM: Artificial Sequence
<220> FEATURE:
<223> OTHER INFORMATION: 5'-3' Sequence for synthesizing TFO (Duplex 1)

<400> SEQUENCE: 13
atgttttctt tccccttctt ttctatgg                                          28

<210> SEQ ID NO 14
<211> LENGTH: 28
<212> TYPE: DNA
<213> ORGANISM: Artificial Sequence
<220> FEATURE:
<223> OTHER INFORMATION: 3'-5' Sequence for synthesizing TFO (Duplex 1)

<400> SEQUENCE: 14
ccatagaaaa gaagggggaaa gaaaacat                                         28

<210> SEQ ID NO 15
<211> LENGTH: 28
<212> TYPE: DNA
<213> ORGANISM: Artificial
<220> FEATURE:
<223> OTHER INFORMATION: 5'-3'  Sequence for synthesizing TFO (Duplex 2)

<400> SEQUENCE: 15
atgttttctt ttttttctt ttctatgg                                           28

<210> SEQ ID NO 16
<211> LENGTH: 28
<212> TYPE: DNA
<213> ORGANISM: Artificial Sequence
<220> FEATURE:
<223> OTHER INFORMATION: 3'-5' Sequence for synthesizing FTO (Duplex 2)

<400> SEQUENCE: 16
ccatagaaaa gaaaaaaaaa gaaaacat                                          28

<210> SEQ ID NO 17
<211> LENGTH: 28
<212> TYPE: DNA
<213> ORGANISM: Artificial Sequence
<220> FEATURE:
<223> OTHER INFORMATION: 5'-3' sequence for synthesizing FTO (Duplex 3)

<400> SEQUENCE: 17
atgttttctt tctctttctt ttctatgg                                          28

<210> SEQ ID NO 18
<211> LENGTH: 28
<212> TYPE: DNA
<213> ORGANISM: Artificial Sequence
<220> FEATURE:
<223> OTHER INFORMATION: 3'-5' sequence for synthesizing FTO (Duplex 3)

<400> SEQUENCE: 18
ccatagaaaa gaaagagaaa gaaaacat                                          28

<210> SEQ ID NO 19
<211> LENGTH: 28
<212> TYPE: DNA
<213> ORGANISM: Artificial Sequence
<220> FEATURE:
<223> OTHER INFORMATION: 5'-3' sequence for synthesizing FTO (Duplex 4)

<400> SEQUENCE: 19
atgttttctt tcttcttctt ttctatgg                                          28
```

-continued

<210> SEQ ID NO 20
<211> LENGTH: 28
<212> TYPE: DNA
<213> ORGANISM: Artificial Suence
<220> FEATURE:
<223> OTHER INFORMATION: 5'-3' sequence for synthesizing FTO (Duplex 4)

<400> SEQUENCE: 20
ccatagaaaa gaagaagaaa gaaaacat                                              28

<210> SEQ ID NO 21
<211> LENGTH: 21
<212> TYPE: DNA
<213> ORGANISM: Artificial sequence
<220> FEATURE:
<223> OTHER INFORMATION: Triple-forming oligonucleotide
<220> FEATURE:
<221> NAME/KEY: modified_base
<222> LOCATION: (2)..(2)
<223> OTHER INFORMATION: 5-methyl cytosine
<220> FEATURE:
<221> NAME/KEY: modified_base
<222> LOCATION: (7)..(7)
<223> OTHER INFORMATION: 5-methyl cytosine
<220> FEATURE:
<221> NAME/KEY: modified_base
<222> LOCATION: (10)..(13)
<223> OTHER INFORMATION: 5-methyl cytosine
<220> FEATURE:
<221> NAME/KEY: modified_base
<222> LOCATION: (17)..(17)
<223> OTHER INFORMATION: 5-methyl cytosine

<400> SEQUENCE: 21
tcttttcttc ccctttcttt t                                                     21

<210> SEQ ID NO 22
<211> LENGTH: 21
<212> TYPE: DNA
<213> ORGANISM: Artificial Sequence
<220> FEATURE:
<223> OTHER INFORMATION: Triple-forming oligonucleotide
<220> FEATURE:
<221> NAME/KEY: modified_base
<222> LOCATION: (2)..(2)
<223> OTHER INFORMATION: 5-methyl cytosine
<220> FEATURE:
<221> NAME/KEY: modified_base
<222> LOCATION: (7)..(7)
<223> OTHER INFORMATION: 5-methyl cytosine
<220> FEATURE:
<221> NAME/KEY: modified_base
<222> LOCATION: (17)..(17)
<223> OTHER INFORMATION: 5-methyl cytosine

<400> SEQUENCE: 22
tcttttcttt tttttctttt t                                                     21

<210> SEQ ID NO 23
<211> LENGTH: 21
<212> TYPE: DNA
<213> ORGANISM: Artificial Sequence
<220> FEATURE:
<223> OTHER INFORMATION: Triple-forming helix
<220> FEATURE:
<221> NAME/KEY: modified_base
<222> LOCATION: (2)..(2)
<223> OTHER INFORMATION: 5-methyl cytosine
<220> FEATURE:
<221> NAME/KEY: modified_base
<222> LOCATION: (7)..(7)
<223> OTHER INFORMATION: 5-methyl cytosine

```
<220> FEATURE:
<221> NAME/KEY: modified_base
<222> LOCATION: (11)..(11)
<223> OTHER INFORMATION: 5-methyl cytosine
<220> FEATURE:
<221> NAME/KEY: modified_base
<222> LOCATION: (13)..(13)
<223> OTHER INFORMATION: 5-methyl cytosine
<220> FEATURE:
<221> NAME/KEY: modified_base
<222> LOCATION: (17)..(17)
<223> OTHER INFORMATION: 5-methyl cytosine

<400> SEQUENCE: 23
tcttttcttt ctctttcttt t                                              21

<210> SEQ ID NO 24
<211> LENGTH: 21
<212> TYPE: DNA
<213> ORGANISM: Artificial Sequence
<220> FEATURE:
<223> OTHER INFORMATION: Triple-forming oligonucleotide
<220> FEATURE:
<221> NAME/KEY: modified_base
<222> LOCATION: (2)..(2)
<223> OTHER INFORMATION: 5-methyl cytosine
<220> FEATURE:
<221> NAME/KEY: modified_base
<222> LOCATION: (7)..(7)
<223> OTHER INFORMATION: 5-methyl cytosine
<220> FEATURE:
<221> NAME/KEY: modified_base
<222> LOCATION: (10)..(10)
<223> OTHER INFORMATION: 5-methyl cytosine
<220> FEATURE:
<221> NAME/KEY: modified_base
<222> LOCATION: (13)..(13)
<223> OTHER INFORMATION: 5-methyl cytosine
<220> FEATURE:
<221> NAME/KEY: modified_base
<222> LOCATION: (17)..(17)
<223> OTHER INFORMATION: 5-methyl cytosine

<400> SEQUENCE: 24
tcttttcttc ttctttcttt t                                              21

<210> SEQ ID NO 25
<211> LENGTH: 21
<212> TYPE: DNA
<213> ORGANISM: Artificial Sequence
<220> FEATURE:
<223> OTHER INFORMATION: Triple-forming oligonucleotide
<220> FEATURE:
<221> NAME/KEY: modified_base
<222> LOCATION: (1)..(1)
<223> OTHER INFORMATION: 5-methyl cytosine
<220> FEATURE:
<221> NAME/KEY: modified_base
<222> LOCATION: (4)..(4)
<223> OTHER INFORMATION: 5-methyl cytosine
<220> FEATURE:
<221> NAME/KEY: modified_base
<222> LOCATION: (7)..(7)
<223> OTHER INFORMATION: 5-methyl cytosine
<220> FEATURE:
<221> NAME/KEY: modified_base
<222> LOCATION: (10)..(10)
<223> OTHER INFORMATION: 5-methyl cytosine
<220> FEATURE:
<221> NAME/KEY: modified_base
<222> LOCATION: (13)..(13)
<223> OTHER INFORMATION: 5-methyl cytosine
<220> FEATURE:
<221> NAME/KEY: modified_base
<222> LOCATION: (16)..(16)
<223> OTHER INFORMATION: 5-methyl cytosine
```

```
<220> FEATURE:
<221> NAME/KEY: modified_base
<222> LOCATION: (19)..(19)
<223> OTHER INFORMATION: 5-methyl cytosine

<400> SEQUENCE: 25
cttcttcttc ttcttcttct t                                              21

<210> SEQ ID NO 26
<211> LENGTH: 21
<212> TYPE: DNA
<213> ORGANISM: Artificial Sequence
<220> FEATURE:
<223> OTHER INFORMATION: Triple-forming oligonucleotide
<220> FEATURE:
<221> NAME/KEY: modified_base
<222> LOCATION: (2)..(2)
<223> OTHER INFORMATION: 5-methyl cytosine
<220> FEATURE:
<221> NAME/KEY: modified_base
<222> LOCATION: (7)..(7)
<223> OTHER INFORMATION: 5-methyl Cytosine
<220> FEATURE:
<221> NAME/KEY: modified_base
<222> LOCATION: (10)..(13)
<223> OTHER INFORMATION: 8-oxo adenine
<220> FEATURE:
<221> NAME/KEY: modified_base
<222> LOCATION: (17)..(17)
<223> OTHER INFORMATION: 5-methyl cytosine

<400> SEQUENCE: 26
tcttttctta aaatttcttt t                                              21

<210> SEQ ID NO 27
<211> LENGTH: 21
<212> TYPE: DNA
<213> ORGANISM: Artificial Sequence
<220> FEATURE:
<223> OTHER INFORMATION: Triple-forming oligonucleotide
<220> FEATURE:
<221> NAME/KEY: modified_base
<222> LOCATION: (2)..(2)
<223> OTHER INFORMATION: 5-methyl cytosine
<220> FEATURE:
<221> NAME/KEY: modified_base
<222> LOCATION: (7)..(7)
<223> OTHER INFORMATION: 5-methyl cytosine
<220> FEATURE:
<221> NAME/KEY: modified_base
<222> LOCATION: (10)..(10)
<223> OTHER INFORMATION: 5-methyl cytosine
<220> FEATURE:
<221> NAME/KEY: modified_base
<222> LOCATION: (11)..(13)
<223> OTHER INFORMATION: 8-oxo adenine
<220> FEATURE:
<221> NAME/KEY: modified_base
<222> LOCATION: (17)..(17)
<223> OTHER INFORMATION: 5-methyl cytosine

<400> SEQUENCE: 27
tcttttcttc aaatttcttt t                                              21

<210> SEQ ID NO 28
<211> LENGTH: 21
<212> TYPE: DNA
<213> ORGANISM: Artificial Sequence
<220> FEATURE:
<223> OTHER INFORMATION: TRiple-forming oligonucleotide
<220> FEATURE:
<221> NAME/KEY: modified_base
<222> LOCATION: (2)..(2)
<223> OTHER INFORMATION: 5-methyl cytosine
```

```
<220> FEATURE:
<221> NAME/KEY: modified_base
<222> LOCATION: (7)..(7)
<223> OTHER INFORMATION: 5-methyl cytosine
<220> FEATURE:
<221> NAME/KEY: modified_base
<222> LOCATION: (10)..(10)
<223> OTHER INFORMATION: 5-methyl cytosine
<220> FEATURE:
<221> NAME/KEY: modified_base
<222> LOCATION: (11)..(12)
<223> OTHER INFORMATION: 8-oxo adenine
<220> FEATURE:
<221> NAME/KEY: modified_base
<222> LOCATION: (13)..(13)
<223> OTHER INFORMATION: 5-methyl cytosine
<220> FEATURE:
<221> NAME/KEY: modified_base
<222> LOCATION: (17)..(17)
<223> OTHER INFORMATION: 5-methyl cytosine

<400> SEQUENCE: 28
tcttttcttc aactttcttt t                                           21

<210> SEQ ID NO 29
<211> LENGTH: 21
<212> TYPE: DNA
<213> ORGANISM: Artificial Sequence
<220> FEATURE:
<223> OTHER INFORMATION: Triple-forming oligonucleotide
<220> FEATURE:
<221> NAME/KEY: modified_base
<222> LOCATION: (2)..(2)
<223> OTHER INFORMATION: 5-methyl cytosine
<220> FEATURE:
<221> NAME/KEY: modified_base
<222> LOCATION: (7)..(7)
<223> OTHER INFORMATION: 5-methyl cytosine
<220> FEATURE:
<221> NAME/KEY: modified_base
<222> LOCATION: (10)..(10)
<223> OTHER INFORMATION: 8-oxo adenine
<220> FEATURE:
<221> NAME/KEY: modified_base
<222> LOCATION: (11)..(11)
<223> OTHER INFORMATION: 5-methyl cytosine
<220> FEATURE:
<221> NAME/KEY: modified_base
<222> LOCATION: (13)..(13)
<223> OTHER INFORMATION: 5-methyl cytosine
<220> FEATURE:
<221> NAME/KEY: modified_base
<222> LOCATION: (13)..(13)
<223> OTHER INFORMATION: 8-oxo adenine
<220> FEATURE:
<221> NAME/KEY: modified_base
<222> LOCATION: (17)..(17)
<223> OTHER INFORMATION: 5-methyl cytosine

<400> SEQUENCE: 29
tcttttctta cactttcttt t                                           21

<210> SEQ ID NO 30
<211> LENGTH: 21
<212> TYPE: DNA
<213> ORGANISM: Artificial Sequence
<220> FEATURE:
<223> OTHER INFORMATION: Triple-forming oligonucleotide
<220> FEATURE:
<221> NAME/KEY: modified_base
<222> LOCATION: (2)..(2)
<223> OTHER INFORMATION: 8-oxo adenine
<220> FEATURE:
<221> NAME/KEY: modified_base
<222> LOCATION: (7)..(7)
<223> OTHER INFORMATION: 8-oxo adenine
```

```
<220> FEATURE:
<221> NAME/KEY: modified_base
<222> LOCATION: (10)..(13)
<223> OTHER INFORMATION: 8-oxo adenine
<220> FEATURE:
<221> NAME/KEY: modified_base
<222> LOCATION: (17)..(17)
<223> OTHER INFORMATION: 8-oxo adenosine

<400> SEQUENCE: 30
tattttatta aaatttattt t                                              21

<210> SEQ ID NO 31
<211> LENGTH: 21
<212> TYPE: DNA
<213> ORGANISM: Artificial Sequence
<220> FEATURE:
<223> OTHER INFORMATION: Triple-forming oligonucleotide
<220> FEATURE:
<221> NAME/KEY: modified_base
<222> LOCATION: (2)..(2)
<223> OTHER INFORMATION: 5-methyl cytosine
<220> FEATURE:
<221> NAME/KEY: modified_base
<222> LOCATION: (7)..(7)
<223> OTHER INFORMATION: 5-methyl cytosine
<220> FEATURE:
<221> NAME/KEY: modified_base
<222> LOCATION: (10)..(13)
<223> OTHER INFORMATION: pseudoisocytidine
<220> FEATURE:
<221> NAME/KEY: modified_base
<222> LOCATION: (17)..(17)
<223> OTHER INFORMATION: 5-methyl cytosine

<400> SEQUENCE: 31
tcttttcttc ccctttcttt t                                              21

<210> SEQ ID NO 32
<211> LENGTH: 21
<212> TYPE: DNA
<213> ORGANISM: Artificial Sequence
<220> FEATURE:
<223> OTHER INFORMATION: Triple-forming oligonucleotide
<220> FEATURE:
<221> NAME/KEY: modified_base
<222> LOCATION: (2)..(2)
<223> OTHER INFORMATION: 5-methyl cytosine
<220> FEATURE:
<221> NAME/KEY: modified_base
<222> LOCATION: (7)..(7)
<223> OTHER INFORMATION: 5-methyl cytosine
<220> FEATURE:
<221> NAME/KEY: modified_base
<222> LOCATION: (10)..(10)
<223> OTHER INFORMATION: 5-methyl cytosine
<220> FEATURE:
<221> NAME/KEY: modified_base
<222> LOCATION: (11)..(12)
<223> OTHER INFORMATION: pseudoisocytidine
<220> FEATURE:
<221> NAME/KEY: modified_base
<222> LOCATION: (13)..(13)
<223> OTHER INFORMATION: 5-methyl cytosine
<220> FEATURE:
<221> NAME/KEY: modified_base
<222> LOCATION: (17)..(17)
<223> OTHER INFORMATION: 5-methyl cytosine

<400> SEQUENCE: 32
tcttttcttc ccctttcttt t                                              21

<210> SEQ ID NO 33
<211> LENGTH: 21
```

```
<212> TYPE: DNA
<213> ORGANISM: Artificial Sequence
<220> FEATURE:
<223> OTHER INFORMATION: Triplr-forming oligonucleotide
<220> FEATURE:
<221> NAME/KEY: modified_base
<222> LOCATION: (2)..(2)
<223> OTHER INFORMATION: 5-methyl cytosine
<220> FEATURE:
<221> NAME/KEY: modified_base
<222> LOCATION: (7)..(7)
<223> OTHER INFORMATION: 5-methyl cytosine
<220> FEATURE:
<221> NAME/KEY: modified_base
<222> LOCATION: (10)..(10)
<223> OTHER INFORMATION: pseudoisocytidine
<220> FEATURE:
<221> NAME/KEY: modified_base
<222> LOCATION: (11)..(11)
<223> OTHER INFORMATION: 5-methyl cytosine
<220> FEATURE:
<221> NAME/KEY: modified_base
<222> LOCATION: (12)..(12)
<223> OTHER INFORMATION: pseudoisocytidine
<220> FEATURE:
<221> NAME/KEY: modified_base
<222> LOCATION: (13)..(13)
<223> OTHER INFORMATION: 5-methyl cytosine
<220> FEATURE:
<221> NAME/KEY: modified_base
<222> LOCATION: (17)..(17)
<223> OTHER INFORMATION: 5-methyl cytosine

<400> SEQUENCE: 33
tcttttcttc ccctttcttt t                                              21

<210> SEQ ID NO 34
<211> LENGTH: 21
<212> TYPE: DNA
<213> ORGANISM: Artificial Sequence
<220> FEATURE:
<223> OTHER INFORMATION: Triple-forming oligonucleotide
<220> FEATURE:
<221> NAME/KEY: modified_base
<222> LOCATION: (2)..(2)
<223> OTHER INFORMATION: 5-methyl cytosine
<220> FEATURE:
<221> NAME/KEY: modified_base
<222> LOCATION: (7)..(7)
<223> OTHER INFORMATION: 5-methyl cytosine
<220> FEATURE:
<221> NAME/KEY: modified_base
<222> LOCATION: (10)..(13)
<223> OTHER INFORMATION: psedoisocytidine
<220> FEATURE:
<221> NAME/KEY: modified_base
<222> LOCATION: (17)..(17)
<223> OTHER INFORMATION: 5-methyl cytosine
<220> FEATURE:
<221> NAME/KEY: misc_feature
<222> LOCATION: (17)..(20)
<223> OTHER INFORMATION: 2-aminoethoxy sugar

<400> SEQUENCE: 34
tcttttcttc ccctttcttt t                                              21

<210> SEQ ID NO 35
<211> LENGTH: 21
<212> TYPE: DNA
<213> ORGANISM: Artificial Sequence
<220> FEATURE:
<223> OTHER INFORMATION: Triple-forming oligonucleotide
<220> FEATURE:
<221> NAME/KEY: modified_base
<222> LOCATION: (2)..(2)
<223> OTHER INFORMATION: 5-methyl cytosine
```

```
<220> FEATURE:
<221> NAME/KEY: modified_base
<222> LOCATION: (7)..(7)
<223> OTHER INFORMATION: 5-methyl cytosine
<220> FEATURE:
<221> NAME/KEY: modified_base
<222> LOCATION: (10)..(10)
<223> OTHER INFORMATION: 5-methyl cytosine
<220> FEATURE:
<221> NAME/KEY: modified_base
<222> LOCATION: (11)..(12)
<223> OTHER INFORMATION: pseudoisocytidine
<220> FEATURE:
<221> NAME/KEY: modified_base
<222> LOCATION: (13)..(13)
<223> OTHER INFORMATION: 5-methyl cytosine
<220> FEATURE:
<221> NAME/KEY: modified_base
<222> LOCATION: (17)..(17)
<223> OTHER INFORMATION: 5-methyl cytosine
<220> FEATURE:
<221> NAME/KEY: misc_feature
<222> LOCATION: (17)..(20)
<223> OTHER INFORMATION: 2-aminoehoxy sugar

<400> SEQUENCE: 35
tcttttcttc ccctttcttt t                                              21

<210> SEQ ID NO 36
<211> LENGTH: 21
<212> TYPE: DNA
<213> ORGANISM: Artificial Sequence
<220> FEATURE:
<223> OTHER INFORMATION: Triple-forming oligonucleotide
<220> FEATURE:
<221> NAME/KEY: modified_base
<222> LOCATION: (2)..(2)
<223> OTHER INFORMATION: 5-methyl cytosine
<220> FEATURE:
<221> NAME/KEY: modified_base
<222> LOCATION: (7)..(7)
<223> OTHER INFORMATION: 5-methyl cytosine
<220> FEATURE:
<221> NAME/KEY: modified_base
<222> LOCATION: (10)..(10)
<223> OTHER INFORMATION: pseudoisocytidine
<220> FEATURE:
<221> NAME/KEY: modified_base
<222> LOCATION: (11)..(11)
<223> OTHER INFORMATION: 5-methyl cytosine
<220> FEATURE:
<221> NAME/KEY: modified_base
<222> LOCATION: (12)..(12)
<223> OTHER INFORMATION: pseudoisocytidine
<220> FEATURE:
<221> NAME/KEY: modified_base
<222> LOCATION: (13)..(13)
<223> OTHER INFORMATION: 5-methyl cytosine
<220> FEATURE:
<221> NAME/KEY: modified_base
<222> LOCATION: (17)..(17)
<223> OTHER INFORMATION: 5-methyl cytosine
<220> FEATURE:
<221> NAME/KEY: misc_feature
<222> LOCATION: (17)..(20)
<223> OTHER INFORMATION: 2-aminoethoxy sugar

<400> SEQUENCE: 36
tcttttcttc ccctttcttt t                                              21

<210> SEQ ID NO 37
<211> LENGTH: 21
<212> TYPE: DNA
<213> ORGANISM: Artificial Sequence
<220> FEATURE:
<223> OTHER INFORMATION: Triple-forming oligonucleotide
```

```
<220> FEATURE:
<221> NAME/KEY: modified_base
<222> LOCATION: (2)..(2)
<223> OTHER INFORMATION: pseudoisocytidine
<220> FEATURE:
<221> NAME/KEY: modified_base
<222> LOCATION: (7)..(7)
<223> OTHER INFORMATION: pseudoisocytidine
<220> FEATURE:
<221> NAME/KEY: modified_base
<222> LOCATION: (10)..(13)
<223> OTHER INFORMATION: pseudoisocytidine
<220> FEATURE:
<221> NAME/KEY: modified_base
<222> LOCATION: (17)..(17)
<223> OTHER INFORMATION: 5-methyl cytosine
<220> FEATURE:
<221> NAME/KEY: misc_feature
<222> LOCATION: (17)..(20)
<223> OTHER INFORMATION: 2-aminoethoxy sugar

<400> SEQUENCE: 37
tcttttcttc ccctttcttt t                                      21

<210> SEQ ID NO 38
<211> LENGTH: 21
<212> TYPE: DNA
<213> ORGANISM: Artificial Sequence
<220> FEATURE:
<223> OTHER INFORMATION: Triple-forming oligonucleotide
<220> FEATURE:
<221> NAME/KEY: modified_base
<222> LOCATION: (2)..(2)
<223> OTHER INFORMATION: pseudoisocytidine
<220> FEATURE:
<221> NAME/KEY: modified_base
<222> LOCATION: (7)..(7)
<223> OTHER INFORMATION: 5-methyl cytosine
<220> FEATURE:
<221> NAME/KEY: modified_base
<222> LOCATION: (10)..(10)
<223> OTHER INFORMATION: pseudoisocytidine
<220> FEATURE:
<221> NAME/KEY: modified_base
<222> LOCATION: (11)..(11)
<223> OTHER INFORMATION: 5-methyl cytosine
<220> FEATURE:
<221> NAME/KEY: modified_base
<222> LOCATION: (12)..(12)
<223> OTHER INFORMATION: pseudoisocytidine
<220> FEATURE:
<221> NAME/KEY: modified_base
<222> LOCATION: (13)..(13)
<223> OTHER INFORMATION: 5-methyl cytosine
<220> FEATURE:
<221> NAME/KEY: modified_base
<222> LOCATION: (17)..(17)
<223> OTHER INFORMATION: 5-methyl cytosine
<220> FEATURE:
<221> NAME/KEY: misc_feature
<222> LOCATION: (17)..(20)
<223> OTHER INFORMATION: 2-aminoethoxy sugar

<400> SEQUENCE: 38
tcttttcttc ccctttcttt t                                      21

<210> SEQ ID NO 39
<211> LENGTH: 46
<212> TYPE: DNA
<213> ORGANISM: Artificial Sequence
<220> FEATURE:
<223> OTHER INFORMATION: oligonucleotide for generating synthetic duplex

<400> SEQUENCE: 39
gggacccttg atgttttctt tcccttctt ttctatggtt aagttc            46
```

```
<210> SEQ ID NO 40
<211> LENGTH: 46
<212> TYPE: DNA
<213> ORGANISM: Artificial Sequence
<220> FEATURE:
<223> OTHER INFORMATION: Oligonucleotide for generating synthetic duplex

<400> SEQUENCE: 40
gaacttaacc atagaaaaga agggggaaaga aaacatcaag ggtccc         46

<210> SEQ ID NO 41
<211> LENGTH: 32
<212> TYPE: DNA
<213> ORGANISM: Artificial sequence
<220> FEATURE:
<223> OTHER INFORMATION: Oligonucleotide for generating 2-24 bis PNA
      target site

<400> SEQUENCE: 41
gatcttttct ttccccttct tttctatggt ta                         32

<210> SEQ ID NO 42
<211> LENGTH: 32
<212> TYPE: DNA
<213> ORGANISM: Artificial Sequence
<220> FEATURE:
<223> OTHER INFORMATION: Oligonucleotide for generating target site for
      2-24 bis-PNAs

<400> SEQUENCE: 42
gatctaacca tagaaaagaa ggggaaagaa aa                         32

<210> SEQ ID NO 43
<211> LENGTH: 36
<212> TYPE: DNA
<213> ORGANISM: Artificial Sequence
<220> FEATURE:
<223> OTHER INFORMATION: Oligonucleotide for generating target site for
      2-215 bis PNAs

<400> SEQUENCE: 43
gatctttaaa aaatgctttc ttcttttaat atactt                     36

<210> SEQ ID NO 44
<211> LENGTH: 36
<212> TYPE: DNA
<213> ORGANISM: Artificial Sequence
<220> FEATURE:
<223> OTHER INFORMATION: Oligonucloetide for generating target site for
      2-512 bis PNAs

<400> SEQUENCE: 44
aattaagtat attaaaagaa gaaagcattt tttaaa                     36

<210> SEQ ID NO 45
<211> LENGTH: 34
<212> TYPE: DNA
<213> ORGANISM: Artificial Sequence
<220> FEATURE:
<223> OTHER INFORMATION: Oligonucleotide for generating target site for
      2-830 bis-PNAs

<400> SEQUENCE: 45
gatcatacct cttatcttcc tcccacagga ctgc                       34

<210> SEQ ID NO 46
```

-continued

```
<211> LENGTH: 34
<212> TYPE: DNA
<213> ORGANISM: Artificial Sequence
<220> FEATURE:
<223> OTHER INFORMATION: Oligonucleotide for generating 2-830 bis-PNAs

<400> SEQUENCE: 46
aattgcagtc ctgtgggagg aagataagag gtat                              34

<210> SEQ ID NO 47
<211> LENGTH: 20
<212> TYPE: DNA
<213> ORGANISM: Artificial Sequence
<220> FEATURE:
<223> OTHER INFORMATION: PNAa sequence
<220> FEATURE:
<221> NAME/KEY: modified_base
<222> LOCATION: (2)..(2)
<223> OTHER INFORMATION: pseudoisocytidine
<220> FEATURE:
<221> NAME/KEY: modified_base
<222> LOCATION: (7)..(7)
<223> OTHER INFORMATION: pseudoisocytidine
<220> FEATURE:
<221> NAME/KEY: misc_feature
<222> LOCATION: (10)..(11)
<223> OTHER INFORMATION: (8-amino-3,6-dioxaoctanoic acid)3  phosphate
      backbone modification
<220> FEATURE:
<221> NAME/KEY: misc_feature
<222> LOCATION: (10)..(11)
<223> OTHER INFORMATION: (8-amino-3,6-dioxaoctanoic acid)3  modification
<220> FEATURE:
<221> NAME/KEY: modified_base
<222> LOCATION: (10)..(10)
<223> OTHER INFORMATION: pseudoisocytidine
<220> FEATURE:
<221> NAME/KEY: misc_feature
<222> LOCATION: (20)..(20)
<223> OTHER INFORMATION: Lys-Lys-Lys modification

<400> SEQUENCE: 47
tcttttcttc cttcttttct                                              20

<210> SEQ ID NO 48
<211> LENGTH: 20
<212> TYPE: DNA
<213> ORGANISM: Artificial Sequence
<220> FEATURE:
<223> OTHER INFORMATION: PNAs sequence
<220> FEATURE:
<221> NAME/KEY: modified_base
<222> LOCATION: (3)..(3)
<223> OTHER INFORMATION: pseudoisocytidine
<220> FEATURE:
<221> NAME/KEY: modified_base
<222> LOCATION: (6)..(6)
<223> OTHER INFORMATION: pseudoisocytidine
<220> FEATURE:
<221> NAME/KEY: modified_base
<222> LOCATION: (10)..(10)
<223> OTHER INFORMATION: pseudoisocytidine
<220> FEATURE:
<221> NAME/KEY: misc_feature
<222> LOCATION: (10)..(11)
<223> OTHER INFORMATION: 8-amino-3,6-dioxaoctanoic
      acid-lysine(succinimidyl-4-(M-maleimidomethyl)cyclohexane-1-carbo
      xylate-8-amino-3,6-dioxaoctanoic acid modification
<220> FEATURE:
<221> NAME/KEY: misc_feature
<222> LOCATION: (10)..(11)
<223> OTHER INFORMATION: 8-amino-3,6-dioxaoctanoic
      acid-lysine-(succinimidyl-4-(N-maleimidomethyl)cyclohexane-1-carb
      oxylate)-8-amino-3,6-dioxaoctanoic acid modification

<400> SEQUENCE: 48
```
ttcttctttc ctttcttctt                                            20

<210> SEQ ID NO 49
<211> LENGTH: 20
<212> TYPE: DNA
<213> ORGANISM: Artificial Sequence
<220> FEATURE:
<223> OTHER INFORMATION: PNAs sequence
<220> FEATURE:
<221> NAME/KEY: modified_base
<222> LOCATION: (1)..(3)
<223> OTHER INFORMATION: pseudoisocytidine
<220> FEATURE:
<221> NAME/KEY: modified_base
<222> LOCATION: (5)..(6)
<223> OTHER INFORMATION: pseudoisocytidine
<220> FEATURE:
<221> NAME/KEY: modified_base
<222> LOCATION: (9)..(9)
<223> OTHER INFORMATION: pseudoisocytidine
<220> FEATURE:
<221> NAME/KEY: misc_feature
<222> LOCATION: (10)..(11)
<223> OTHER INFORMATION: 8-amino-3,6-dioxaoctanoic
      acid-lysine(succinimidyl-4-(M-maleimidomethyl)cyclohexane-1-carbo
      xylate-8-amino-3,6-dioxaoctanoic acid modification

<400> SEQUENCE: 49
ccctccttct tcttcctccc                                            20

<210> SEQ ID NO 50
<211> LENGTH: 51
<212> TYPE: DNA
<213> ORGANISM: Artificial Sequence
<220> FEATURE:
<223> OTHER INFORMATION: DonorGFP-IVS2-1 Sense Primer

<400> SEQUENCE: 50
gttcagcgtg tccggcgagg gcgaggtgag tctatgggac ccttgatgtt t          51

<210> SEQ ID NO 51
<211> LENGTH: 51
<212> TYPE: DNA
<213> ORGANISM: Artificial Sequence
<220> FEATURE:
<223> OTHER INFORMATION: DonorGFP-IVS2-1 antisense primer

<400> SEQUENCE: 51
aaacatcaag ggtcccatag actcacctcg ccctcgccgg acacgctgaa c          51

<210> SEQ ID NO 52
<211> LENGTH: 50
<212> TYPE: DNA
<213> ORGANISM: Artificial Sequence
<220> FEATURE:
<223> OTHER INFORMATION: Donor FLAS primer

<400> SEQUENCE: 52
cgggcctttc tttatgtttt tggcgtcttc catggtggct ttaccaagct            50

<210> SEQ ID NO 53
<211> LENGTH: 51
<212> TYPE: DNA
<213> ORGANISM: Artificial Sequence
<220> FEATURE:
<223> OTHER INFORMATION: Donor FLS primer

<400> SEQUENCE: 53
tggtaaagcc accatggaag acgccaaaaa cataaagaaa ggcccggcgc c          51

```
<210> SEQ ID NO 54
<211> LENGTH: 24
<212> TYPE: DNA
<213> ORGANISM: Artificial Sequence
<220> FEATURE:
<223> OTHER INFORMATION: pJK115 forward primer

<400> SEQUENCE: 54
agcaagggcg aggagctgtt cacc                                          24

<210> SEQ ID NO 55
<211> LENGTH: 23
<212> TYPE: DNA
<213> ORGANISM: Artificial Sequence
<220> FEATURE:
<223> OTHER INFORMATION: pJK118 reverse primer

<400> SEQUENCE: 55
cactgcacgc cgtaggtcag ggt                                           23

<210> SEQ ID NO 56
<211> LENGTH: 24
<212> TYPE: DNA
<213> ORGANISM: Artificial Sequence
<220> FEATURE:
<223> OTHER INFORMATION: pJK127 forward primer

<400> SEQUENCE: 56
ccagtacatg accttatggg actt                                          24

<210> SEQ ID NO 57
<211> LENGTH: 24
<212> TYPE: DNA
<213> ORGANISM: Artificial Sequence
<220> FEATURE:
<223> OTHER INFORMATION: pJK128 reverse primer

<400> SEQUENCE: 57
tattgctatt gccttaaccc agaa                                          24

<210> SEQ ID NO 58
<211> LENGTH: 18
<212> TYPE: DNA
<213> ORGANISM: Homo sapien

<400> SEQUENCE: 58
ttttctttcc ccttcttt                                                 18

<210> SEQ ID NO 59
<211> LENGTH: 850
<212> TYPE: DNA
<213> ORGANISM: Homo sapien

<400> SEQUENCE: 59
gtgagtctat gggacccttg atgttttctt tcccttcttt ttctatggtt aagttcatgt    60
cataggaagg ggagaagtaa cagggtacag tttagaatgg gaaacagacg aatgattgca   120
tcagtgtgga agtctcagga tcgttttagt ttcttttatt tgctgttcat aacaattgtt   180
ttcttttgtt taattcttgc tttcttttt tttcttctcc gcaatttta ctattatact     240 taatgcctta acattgtgta taacaaaagg aaatatctct gagatacatt aagtaactta   300
aaaaaaaact ttacacagtc tgcctagtac attactattt ggaatatatg tgtgcttatt   360
tgcatattca taatctccct actttatttt cttttatttt taattgatac ataatcatta   420
```

-continued

```
tacatattta tgggttaaag tgtaatgttt taatatgtgt acacatattg accaaatcag    480
ggtaattttg catttgtaat tttaaaaaat gctttcttct tttaatatac ttttttgttt    540
atcttatttc taatactttc cctaatctct ttctttcagg gcaataatga tacaatgtat    600
catgcctctt tgcaccattc taaagaataa cagtgataat ttctgggtta aggcaatagc    660
aatatttctg catataaata tttctgcata taaattgtaa ctgatgtaag aggtttcata    720
ttgctaatag cagctacaat ccagctacca ttctgctttt attttatggt tgggataagg    780
ctggattatt ctgagtccaa gctaggccct tttgctaatc atgttcatac ctcttatctt    840
cctcccacag                                                          850

<210> SEQ ID NO 60
<211> LENGTH: 850
<212> TYPE: DNA
<213> ORGANISM: Homo sapien

<400> SEQUENCE: 60
ctgtgggagg aagataagag gtatgaacat gattagcaaa agggcctagc ttggactcag     60
aataatccag ccttatccca accataaaat aaaagcagaa tggtagctgg attgtagctg    120
ctattagcaa tatgaaacct cttacatcag ttacaattta tatgcagaaa tatttatatg    180
cagaaatatt gctattgcct taacccagaa attatcactg ttattcttta gaatggtgca    240
aagaggcatg atacattgta tcattattgc cctgaaagaa agagattagg gaaagtatta    300
gaaataagat aaacaaaaaa gtatattaaa agaagaaagc attttttaaa attacaaatg    360
caaaattacc ctgatttggt caatatgtgt acacatatta aaacattaca ctttaaccca    420
taaatatgta taatgattat gtatcaatta aaaataaaag aaaataaagt agggagatta    480
tgaatatgca aataagcaca catatattcc aaatagtaat gtactaggca gactgtgtaa    540 agttttttt taagttactt aatgtatctc agagatattt cctttgtta tacacaatgt     600 taaggcatta agtataatag taaaaattgc ggagaagaaa aaaaagaaa gcaagaatta    660 aacaaaagaa aacaattgtt atgaacagca aataaaagaa actaaaacga tcctgagact    720
tccacactga tgcaatcatt cgtctgtttc ccattctaaa ctgtaccctg ttacttctcc    780
ccttcctatg acatgaactt aaccatagaa aagaagggga aagaaaacat caagggtccc    840
atagactcac                                                          850
```